(12) United States Patent
Pulé et al.

(10) Patent No.: US 10,286,092 B2
(45) Date of Patent: May 14, 2019

(54) DETECTING A THERAPEUTIC CELL

(71) Applicant: UCL Business PLC, London (GB)

(72) Inventors: Martin Pulé, London (GB); Adam Badar, London (GB); Louise Kiru, London (GB); Mark Lythgoe, London (GB); Adrien Peters, Brighton (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 14/835,301

(22) Filed: Aug. 25, 2015

(65) Prior Publication Data
US 2017/0056534 A1    Mar. 2, 2017

(51) Int. Cl.
| | | |
|---|---|---|
| A61K 38/17 | (2006.01) | |
| A61K 51/04 | (2006.01) | |
| C07K 14/47 | (2006.01) | |
| C07K 16/28 | (2006.01) | |
| A61K 39/395 | (2006.01) | |

(52) U.S. Cl.
CPC ...... *A61K 51/0455* (2013.01); *A61K 38/1709* (2013.01); *A61K 39/3955* (2013.01); *C07K 14/4702* (2013.01); *C07K 16/2809* (2013.01); *C07K 16/2818* (2013.01); *C07K 16/2896* (2013.01); *C07K 2317/622* (2013.01); *C07K 2319/02* (2013.01); *C07K 2319/74* (2013.01)

(58) Field of Classification Search
CPC combination set(s) only.
See application file for complete search history.

(56) References Cited

PUBLICATIONS

Politis et al., Movement Disorders, 26(11):1997-2003, Sep. 2011.*
Jørgensen et al., Exp Neurology, 198:427-437, 2006.*
Johnson et al., Sci Transl Med, 7(725), Feb. 2015.*
Gordon and Barnes TRENDS in Immunology, 24(8), Aug. 2003.*
Boronat-Ferrater et al, Clinical Nuclear Medicine, 34(9) p. 608, Sep. 2009.*
Pogarell et al., Eur j Nuclear Med and Mol Imaging, 33(4):407-411, Apr. 2006.*
Han et al. Translational Neurodegeneration (2015) 4:16.*
Ouchi et al. Ann Neurol, 57:168-175 (2005).*
Hayashi et al., J Clin. Investigation, 123(1):272-84 (2013).*
Andringa et al., Pinhole SPECT imaging of dopamine transporters correlates with dopamine transporter immunohistochemical analysis in the MPTP mouse model of Parkinson's disease, *NeuroImage*, 26:1150-8 (2005).
Badar et al., Fluorescence-guided development of a tricistronic vector encoding bimodal optical and nuclear genetic reporters for in vivo cellular imaging, *EJNMMI Res.*,5:18 (2015).
Bochkov et al., Translational efficiency of EMCV IRES in bicistronic vectors is dependent upon IRES sequence and gene location, *Biotechniques*, 41:283 (2006).
Bradbury et al., The CD19 signal transduction complex of B lymphocytes. Deletion of the CD19 cytoplasmic domain alters signal transduction but not complex formation with TAPA-1 and Leu 13, *J. Immunol.*, 151:2915-27 (1993).
Donnelly et al., The "cleavage" activities of foot-and-mouth disease virus 2A site-directed mutants and naturally occurring '2A-like', *J. Gen. Virol.*, 82:1027-41 (2001).
Hiasa et al., Long-term phenotypic, functional and genetic stability of cancer-specific T-cell receptor (TCR) alphabeta genes transduced to CD8+ T cells, *Gene Ther.*, 15:695-9 (2008).
Kim et al., Dopamine neurons derived from embryonic stem cells function in an animal model of Parkinson's disease, *Nature*, 418:50-6 (2002).
Laruelle et al., Graphical, kinetic, and equilibrium analyses of in vivo [123I] beta-CIT binding to dopamine transporters in healthy human subjects, *J. Cerebral Blood flow and Metabol.*, 14:982-94 (1994).
Latchney et al., Therapeutic application of neural stem cells and adult meurogenesis for neurogegenrative disorders: regeneration and beyond, *Eur. J. Neurodegen. Dis.*, 1(3):335-51 (2012).
Moosmann et al. Effective and long-term control of EBV PTLD after transfer of peptide-selected T cells, *Blood*,115:2960-70 (2010).
Philip et al., A highly compact epitope-based marker/suicide gene for easier and safer T-cell therapy, Blood, 124:1277-87 (2014).
Piccini et al., Dopamine transporter: Basic aspects and neuroimaging, *Movement Disorders*, 18(7):S3-8 (2003).
Riviere et al., Effects of retroviral vector design on expression of human adenosine deaminase in murine bone marrow transplant recipients engrafted with genetically modified cells, *Proc. Natl. Acad. Sci. USA*, 92:6733-7 (1995).
Shen et al., Recent Advances in Imaging of Dopaminergic Neurons for Evaluation of Neuropsychiatric Disorders, *J. Biomed. Biotechnol.*, Article ID 259349 (2012).
Van Dyck et al. Age-related decline in striatal dopamine transporter binding with iodine-123-beta-CITSPECT, *J. Nucl. Med.*, 36:1175-81 (1995).

\* cited by examiner

*Primary Examiner* — Kimberly Ballard
*Assistant Examiner* — Stacey N MacFarlane
(74) *Attorney, Agent, or Firm* — Marshall, Gerstein & Borun LLP

(57) ABSTRACT

The present invention relates to a method of detecting a therapeutic cell expressing a dopamine transporter (DAT) at a central nervous system (CNS) site in a subject, which comprises the administration of a DAT tracer to the subject, wherein the presence of a therapeutic cell which expresses the DAT is determined.

6 Claims, 18 Drawing Sheets
Specification includes a Sequence Listing.

hDAT cassette

[$^{123}$I]-FP-CIT/DaTSCAN

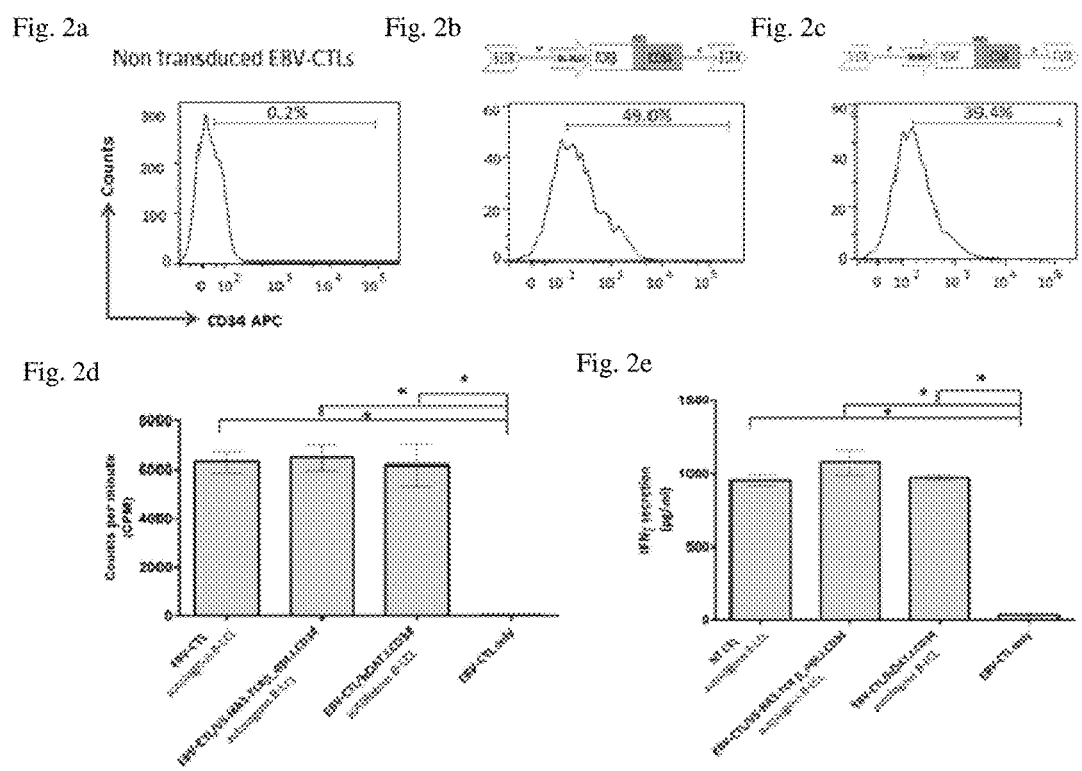

Last two transmembrane domains deleted from the carboxy terminal

Protein Sequence of hDAT tm11-12 (SEQ ID NO: 2)

MSKSKCSVGLMSSVVAPAKEPNAVGPKEVELILVKEQNGVQLTSSTLTNPRQSPVEAQDR
ETWGKKIDFLLSVIGFAVDLANVWRFPYLCYKNGGGAFLVPYLLFMVIAGMPLFYMELAL
GQFNREGAAGVWKICPILKGVGFTVILISLYVGFFYNVIIAWALHYLFSSFTTELPWIHC
NNSWNSPNCSDAHPGDSSGDSSGLNDTFGTTPAAEYFERGVLHLHQSHGIDDLGPPRWQL
TACLVLVIVLLYFSLWKGVKTSGKVVWITATMPYVVLTALLLRGVTLPGAIDGIRAYLSV
DFYRLCEASVWIDAATQVCFSLGVGFGVLIAFSSYNKFTNNCYRDAIVTTSINSLTSFSS
GFVVFSFLGYMAQKHSVPIGDVAKDGPGLIFIIYPEAIATLPLSSAWAVVFFIMLLTLGI
DSAMGGMESVITGLIDEFQLLHRHRELFTLFIVLATFLLSLFCVTNGGIYVFTLLDHFAA
GTSILFGVLIEAIGVAWFYGVGQFSDDIQQMTGQRPSLY

Nucleic acid sequence of hDAT tm11-12 (SEQ ID NO: 23)

GAGCAAGAGCAAGTGCAGCGTGGGCCTGATGAGCAGCGTGGTGGCCCCAGCCAAGGAGCC
CAACGCCGTGGGCCCTAAGGAGGTGGAGCTGATCCTGGTGAAGGAGCAGAACGGCGTGCA
GCTGACCAGCAGCACCCTGACCAACCCTAGACAGAGCCCCGTGGAGGCCCAGGACCGGGA
GACCTGGGGCAAGAAGATCGACTTCCTGCTGAGCGTGATCGGCTTCGCCGTGGACCTGGC
CAACGTGTGGCGGTTCCCCTACCTGTGCTACAAGAACGGCGGAGGCGCCTTCCTGGTGCC
CTACCTGCTGTTCATGGTGATCGCCGGCATGCCTCTGTTCTACATGGAGCTGGCCCTGGG
CCAGTTCAACCGGGAGGGCGCCGCCGGCGTGTGGAAAATCTGCCCTATCCTGAAGGGCGT
GGGCTTCACCGTGATCCTGATCAGCCTGTACGTGGGCTTCTTCTACAACGTGATCATCGC
CTGGGCCCTGCACTACCTGTTCAGCAGCTTCACCACCGAGCTGCCCTGGATTCACTGCAA
CAACAGCTGGAACAGCCCCAACTGCAGCGACGCCCACCCCGGCGACAGCAGCGGCGACAG
CAGCGGCCTGAACGACACCTTCGGCACCACCCCAGCCGCCGAGTACTTCGAGCGCGGCGT
GCTGCACCTGCACCAGAGCCACGGCATCGACGACCTGGGCCCACCTCGGTGGCAGCTGAC
CGCCTGCCTGGTGCTGGTGATCGTGCTGCTGTACTTCAGCCTGTGGAAGGGCGTGAAGAC
CAGCGGCAAGGTGGTGTGGATCACCGCCACCATGCCCTACGTGGTGCTGACCGCCCTGCT
GCTGCGCGGCGTGACCCTGCCCGGCGCCATCGACGGCATCCGGGCCTACCTGAGCGTGGA
CTTCTACCGGCTGTGCGAGGCCAGCGTGTGGATCGACGCCGCCACCCAGGTGTGCTTCAG
CCTGGGCGTGGGCTTCGGCGTGCTGATCGCCTTCAGCAGCTACAACAAGTTCACCAACAA
CTGCTACCGGGACGCCATCGTGACCACCAGCATCAACAGCCTGACCAGCTTCAGCAGCGG
CTTCGTGGTGTTCAGCTTCCTGGGCTACATGGCCCAGAAGCACAGCGTGCCCATCGGCGA
CGTGGCCAAGGACGGTCCCGGCCTGATCTTCATCATCTACCCCGAGGCCATCGCCACCCT
GCCCCTGAGCAGCGCCTGGGCCGTGGTGTTCTTCATCATGCTGCTGACCCTGGGCATCGA
CAGCGCTATGGGCGGCATGGAGAGCGTGATCACCGGCCTGATCGACGAGTTCCAGCTGCT
GCACCGGCACCGGGAGCTGTTCACCCTGTTCATCGTGCTGGCCACCTTCCTGCTGAGCCT
GTTCTGCGTGACCAACGGCGGCATCTACGTGTTCACCCTGCTGGACCACTTCGCCGCCGG
CACCAGCATCCTGTTCGGCGTGCTGATCGAGGCCATCGGCGTGGCCTGGTTCTACGGCGT
GGGTCAGTTCAGCGACGACATCCAGCAGATGACCGGCCAGCGGCCCAGCCTGTACTGA

FIGURE 9 – CONT.

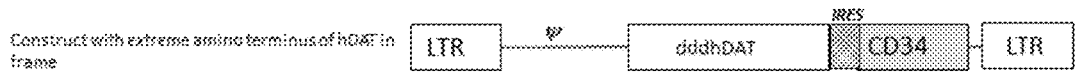

Construct with extreme amino terminus of hDAT in frame | LTR |—ψ—| dddhDAT | IRES CD34 | LTR |

Protein Sequence of dddhDAT (SEQ ID NO: 3)

MRQSPVEAQDRETWGKKIDFLLSVIGFAVDLANVWRFPYLCYKNGGGAFLVPYLLFMVIA
GMLVRRGARAGPRMPRGWTALCLLSLLPSGFMSLDNNGTATPELPTQGTFSNVSTNVSYQ
ETTTPSTLGSTSLHPVSQHGNEATTNITETTVKFTSTSVITSVYGNTNSSVQSQTSVIST
VFTTPANVSTPETTLKPSLSPGNVSDLSTTSTSLATSPTKPYTSSSPILSDIKAEIKCSG
IREVKLTQGICLEQNKTSSCAEFKKDRGEGLARVLCGEEQADADAGAQVCSLLLAQSEVR
PQCLLLVLANRTEISSKLQLMKKHQSDLKKLGILDFTEQDVASHQSYSQKTLIALVTSGA
LLAVLGITGYFLMNRRSWSPTGERLGEDPYYTENGG

Nucleic acid sequence of dddhDAT (SEQ ID NO: 24)

GAGACCTCTGGCGGCAGCCTACCAAGAACAACTGGAC
CGACCGGTGGTACCTCACCCTTACCGAGTCGGCGACACAGTGTGGGTCCGCCGACACCAG
ACTAAGAACCTAGAACCTCGCTGGAAAGGACCTTACACAGTCCTGCTGACCACCCCCACC
GCCCTCAAAGTAGACGGCATCGCAGCTTGGATACACGCCGCCCACGTGAAGGCTGCCGAC
CCCGGGGGTGGACCATCCTCTAGACTGTCGACGCCACCATGAGACAGAGCCCCGTGGAGG
CCCAGGACCGGGAGACCTGGGGCAAGAAGATCGACTTCCTGCTGAGCGTGATCGGCTTCG
CCGTGGACCTGGCCAACGTGTGGCGGTTCCCCTACCTGTGCTACAAGAACGGCGGAGGCG
CCTTCCTGGTGCCCTACCTGCTGTTCATGGTGATCGCCGGCATGCTGGTCCGCAGGGGCG
CGCGCGCAGGGCCCAGGATGCCGCGGGGCTGGACCGCGCTTTGCTTGCTGAGTTTGCTGC
CTTCTGGGTTCATGAGTCTTGACAACAACGGTACTGCTACCCCAGAGTTACCTACCCAGG
GAACATTTTCAAATGTTTCTACAAATGTATCCTACCAAGAAACTACAACACCTAGTACCC
TTGGAAGTACCAGCCTGCACCCTGTGTCTCAACATGGCAATGAGGCCACAACAAACATCA
CAGAAACGACAGTCAAATTCACATCTACCTCTGTGATAACCTCAGTTTATGGAAACACAA
ACTCTTCTGTCCAGTCACAGACCTCTGTAATCAGCACAGTGTTCACCACCCCAGCCAACG
TTTCAACTCCAGAGACAACCTTGAAGCCTAGCCTGTCACCTGGAAATGTTTCAGACCTTT
CAACCACTAGCACTAGCCTTGCAACATCTCCCACTAAACCCTATACATCATCTTCTCCTA
TCCTAAGTGACATCAAGGCAGAAATCAAATGTTCAGGCATCAGAGAAGTGAAATTGACTC
AGGGCATCTGCCTGGAGCAAAATAAGACCTCCAGCTGTGCGGAGTTTAAGAAGGACAGGG
GAGAGGGCCTGGCCCGAGTGCTGTGTGGGGAGGAGCAGGCTGATGCTGATGCTGGGGCCC
AGGTATGCTCCCTGCTCCTTGCCCAGTCTGAGGTGAGGCCTCAGTGTCTACTGCTGGTCT
TGGCCAACAGAACAGAAATTTCCAGCAAACTCCAACTTATGAAAAAGCACCAATCTGACC
TGAAAAAGCTGGGGATCCTAGATTTCACTGAGCAAGATGTTGCAAGCCACCAGAGCTATT
CCCAAAAGACCCTGATTGCACTGGTCACCTCGGGAGCCCTGCTGGCTGTCTTGGGCATCA
CTGGCTATTTCCTGATGAATCGCCGCAGCTGGAGCCCCACAGGAGAAAGGCTGGGCGAAG
ACCCTTATTACACGGAAAACGGTGGATAAGGCGCGTCATCATCGATCCGGATTAGTCCAA
TTTGTTAAAGACAGGATATCAGTGGTCCAGGCTCTAGTTTTGACTCAACAATATCACCAG
CTGAAGCCTATAGAGTACGAGCCATAGATAAAATAA

FIGURE 9 – CONT.

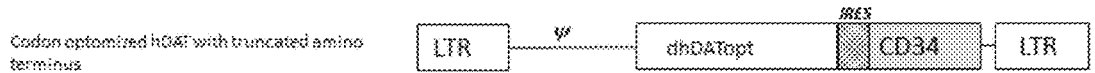

Codon optimized hDAT with truncated amino terminus

Protein Sequence of dhDAT (SEQ ID NO: 4)

MRQSPVEAQDRETWGKKIDFLLSVIGFAVDLANVWRFPYLCYKNGGGAFLVPYLLFMVIA
GMPLFYMELALGQFNREGAAGVWKICPILKGVGFTVILISLYVGFFYNVIIAWALHYLFS
SFTTELPWIHCNNSWNSPNCSDAHPGDSSGDSSGLNDTFGTTPAAEYFERGVLHLHQSHG
IDDLGPPRWQLTACLVLVIVLLYFSLWKGVKTSGKVVWITATMPYVVLTALLLRGVTLPG
AIDGIRAYLSVDFYRLCEASVWIDAATQVCFSLGVGFGVLIAFSSYNKFTNNCYRDAIVT
TSINSLTSFSSGFVVFSFLGYMAQKHSVPIGDVAKDGPGLIFIIYPEAIATLPLSSAWAV
VFFIMLLTLGIDSAMGGMESVITGLIDEFQLLHRHRELFTLFIVLATFLLSLFCVTNGGI
YVFTLLDHFAAGTSILFGVLIEAIGVAWFYGVGQFSDDIQQMTGQRPSLYWRLCWKLVSP
CFLLFVVVSIVTFRPPHYGAYIFPDWANALGWVIATSSMAMVPIYAAYKFCSLPGSFRE
KLAYAIAPEKDRELVDRGEVRQFTLRHWLKV

Nucleic acid sequence of dhDAT (SEQ ID NO: 25)

GAGACAGAGCCCCGTGGAGGCCCAGGACCGGGAGACCTGGGGCAAGAAGA
TCGACTTCCTGCTGAGCGTGATCGGCTTCGCCGTGGACCTGGCCAACGTGTGGCGGTTCC
CCTACCTGTGCTACAAGAACGGCGGAGGCGCCTTCCTGGTGCCCTACCTGCTGTTCATGG
TGATCGCCGGCATGCCTCTGTTCTACATGGAGCTGGCCCTGGGCCAGTTCAACCGGGAGG
GCGCCGCCGGCGTGTGGAAAATCTGCCCTATCCTGAAGGGCGTGGGCTTCACCGTGATCC
TGATCAGCCTGTACGTGGGCTTCTTCTACAACGTGATCATCGCCTGGGCCCTGCACTACC
TGTTCAGCAGCTTCACCACCGAGCTGCCCTGGATTCACTGCAACAACAGCTGGAACAGCC
CCAACTGCAGCGACGCCCACCCCGGCGACAGCAGCGGCGACAGCAGCGGCCTGAACGACA
CCTTCGGCACCACCCCAGCCGCCGAGTACTTCGAGCGCGGCGTGCTGCACCTGCACCAGA
GCCACGGCATCGACGACCTGGGCCCCACCTCGGTGGCAGCTGACCGCCTGCTGGTGCTGG
TGATCGTGCTGCTGTACTTCAGCCTGTGGAAGGGCGTGAAGACCAGCGGCAAGGTGGTGT
GGATCACCGCCACCATGCCCTACGTGGTGCTGACCGCCCTGCTGCTGCGCGGCGTGACCC
TGCCCGGCGCCATCGACGGCATCCGGGCCTACCTGAGCGTGGACTTCTACCGGCTGTGCG
AGGCCAGCGTGTGGATCGACGCCGCCACCCAGGTGTGCTTCAGCCTGGGCGTGGGCTTCG
GCGTGCTGATCGCCTTCAGCAGCTACAACAAGTTCACCAACAACTGCTACCGGGACGCCA
TCGTGACCACCAGCATCAACAGCCTGACCAGCTTCAGCAGCGGCTTCGTGGTGTTCAGCT
TCCTGGGCTACATGGCCCAGAAGCACAGCGTGCCCATCGGCGACGTGGCCAAGGACGGTC
CCGGCCTGATCTTCATCATCTACCCCGAGGCCATCGCCACCCTGCCCCTGAGCAGCGCCT
GGGCCGTGGTGTTCTTCATCATGCTGCTGACCCTGGGCATCGACAGCGCTATGGGCGGCA
TGGAGAGCGTGATCACCGGCCTGATCGACGAGTTCCAGCTGCTGCACCGGCACCGGGAGC
TGTTCACCCTGTTCATCGTGCTGGCCACCTTCCTGCTGAGCCTGTTCTGCGTGACCAACG
GCGGCATCTACGTGTTCACCCTGCTGGACCACTTCGCCGCCGGCACCAGCATCCTGTTCG
GCGTGCTGATCGAGGCCATCGGCGTGGCCTGGTTCTACGGCGTGGGTCAGTTCAGCGACG
ACATCCAGCAGATGACCGGCCAGCGGCCCAGCCTGTACTGGCGGCTGTGCTGGAAGCTGG
TGAGCCCTTGCTTCCTGCTGTTCGTGGTGGTGGTGAGCATCGTGACCTTCCGGCCACCTC
ACTACGGCGCCTACATCTTCCCCGACTGGGCCAACGCCCTGGGCTGGGTGATCGCCACCA
GCAGCATGGCTATGGTGCCCATCTACGCCGCCTACAAGTTCTGCAGCCTGCCCGGCAGCT
TCCGCGAGAAGCTGGCCTACGCCATCGCCCCAGAGAAGGACCGGGAGCTGGTGGACCGCG
GCGAGGTGCGGCAGTTCACCCTGCGGCACTGGCTGAAGGTGTGA

FIGURE 9 – CONT.

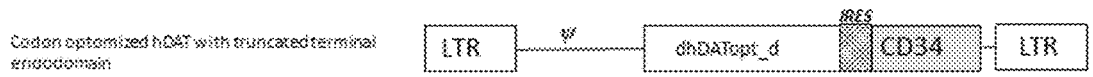

Codon optimized hDAT with truncated terminal endodomain

Protein Sequence of dhDATopt_d (SEQ ID NO: 5)

MSKSKCSVGLMSSVVAPAKEPNAVGPKEVELILVKEQNGVQLTSSTLTNPRQSPVEAQDR
ETWGKKIDFLLSVIGFAVDLANVWRFPYLCYKNGGGAFLVPYLLFMVIAGMPLFYMELAL
GQFNREGAAGVWKICPILKGVGFTVILISLYVGFFYNVIIAWALHYLFSSFTTELPWIHC
NNSWNSPNCSDAHPGDSSGDSSGLNDTFGTTPAAEYFERGVLHLHQSHGIDDLGPPRWQL
TACLVLVIVLLYFSLWKGVKTSGKVVWITATMPYVVLTALLLRGVTLPGAIDGIRAYLSV
DFYRLCEASVWIDAATQVCFSLGVGFGVLIAFSSYNKFTNNCYRDAIVTTSINSLTSFSS
GFVVFSFLGYMAQKHSVPIGDVAKDGPGLIFIIYPEAIATLPLSSAWAVVFFIMLLTLGI
DSAMGGMESVITGLIDEFQLLHRHRELFTLFIVLATFLLSLFCVTNGGIYVFTLLDHFAA
GTSILFGVLIEAIGVAWFYGVGQFSDDIQQMTGQRPSLYWRLCWKLVSPCFLLFVVVVSI
VTFRPPHYGAYIFPDWANALGWVIATSSMAMVPIYAAYKFCSLPGSFREKLAYAIAPEKDRE

Nucleic acid sequence of dhDATopt_d (SEQ ID NO: 26)

GAGCAAGAGCAAGTGCAGCGTGGGCCTGATGAGCAGCGTGGTGGCCCCAG
CCAAGGAGCCCAACGCCGTGGGCCCTAAGGAGGTGGAGCTGATCCTGGTGAAGGAGCAGA
ACGGCGTGCAGCTGACCAGCAGCACCCTGACCAACCCTAGACAGAGCCCCGTGGAGGCCC
AGGACCGGGAGACCTGGGGCAAGAAGATCGACTTCCTGCTGAGCGTGATCGGCTTCGCCG
TGGACCTGGCCAACGTGTGGCGGTTCCCCTACCTGTGCTACAAGAACGGCGGAGGCGCCT
TCCTGGTGCCCTACCTGCTGTTCATGGTGATCGCCGGCATGCCTCTGTTCTACATGGAGC
TGGCCCTGGGCCAGTTCAACCGGGAGGGCGCCGCCGGCGTGTGGAAAATCTGCCCTATCC
TGAAGGGCGTGGGCTTCACCGTGATCCTGATCAGCCTGTACGTGGGCTTCTTCTACAACG
TGATCATCGCCTGGGCCCTGCACTACCTGTTCAGCAGCTTCACCACCGAGCTGCCCTGGA
TTCACTGCAACAACAGCTGGAACAGCCCCAACTGCAGCGACGCCCACCCCGGCGACAGCA
GCGGCGACAGCAGCGGCCTGAACGACACCTTCGGCACCACCCCAGCCGCCGAGTACTTCG
AGCGCGGCGTGCTGCACCTGCACCAGAGCCACGGCATCGACGACCTGGGCCCACCTCGGT
GGCAGCTGACCGCCTGCCTGGTGCTGGTGATCGTGCTGCTGTACTTCAGCCTGTGGAAGG
GCGTGAAGACCAGCGGCAAGGTGGTGTGGATCACCGCCACCATGCCCTACGTGGTGCTGA
CCGCCCTGCTGCTGCGCGGCGTGACCCTGCCCGGCGCCATCGACGGCATCCGGGCCTACC
TGAGCGTGGACTTCTACCGGCTGTGCGAGGCCAGCGTGTGGATCGACGCCGCCACCCAGG
TGTGCTTCAGCCTGGGCGTGGGCTTCGGCGTGCTGATCGCCTTCAGCAGCTACAACAAGT
TCACCAACAACTGCTACCGGGACGCCATCGTGACCACCAGCATCAACAGCCTGACCAGCT
TCAGCAGCGGCTTCGTGGTGTTCAGCTTCCTGGGCTACATGGCCCAGAAGCACAGCGTGC
CCATCGGCGACGTGGCCAAGGACGGTCCCGGCCTGATCTTCATCATCTACCCCGAGGCCA
TCGCCACCCTGCCCCTGAGCAGCGCCTGGGCCGTGGTGTTCTTCATCATGCTGCTGACCC
TGGGCATCGACAGCGCTATGGGCGGCATGGAGAGCGTGATCACCGGCCTGATCGACGAGT
TCCAGCTGCTGCACCGGCACCGGGAGCTGTTCACCCTGTTCATCGTGCTGGCCACCTTCC
TGCTGAGCCTGTTCTGCGTGACCAACGGCGGCATCTACGTGTTCACCCTGCTGGACCACT
TCGCCGCCGGCACCAGCATCCTGTTCGGCGTGCTGATCGAGGCCATCGGCGTGGCCTGGT
TCTACGGCGTGGGTCAGTTCAGCGACGACATCCAGCAGATGACCGGCCAGCGGCCCAGCC
TGTACTGGCGGCTGTGCTGGAAGCTGGTGAGCCCTTGCTTCCTGCTGTTCGTGGTGGTGG
TGAGCATCGTGACCTTCCGGCCACCTCACTACGGCGCCTACATCTTCCCCGACTGGGCCA
ACGCCCTGGGCTGGGTGATCGCCACCAGCAGCATGGCTATGGTGCCCATCTACGCCGCCT
ACAAGTTCTGCAGCCTGCCCGGCAGCTTCCGCGAGAAGCTGGCCTACGCCATCGCCCAG
AGAAGGACCGGGAGTGA

FIGURE 9 – CONT.

Wild type hDAT

Protein Sequence of hDAT (SEQ ID NO: 6)

MSKSKCSVGLMSSVVAPAKEPNAVGPKEVELILVKEQNGVQLTSSTLTNPRQSPVEAQDR
ETWGKKIDFLLSVIGFAVDLANVWRFPYLCYKNGGGAFLVPYLLFMVIAGMPLFYMELAL
GQFNREGAAGVWKICPILKGVGFTVILISLYVGFFYNVIIAWALHYLFSSFTTELPWIHC
NNSWNSPNCSDAHPGDSSGDSSGLNDTFGTTPAAEYFERGVLHLQSHGIDDLGPPRWQL
TACLVLVIVLLYFSLWKGVKTSGKVVWITATMPYVVLTALLLRGVTLPGAIDGIRAYLSV
DFYRLCEASVWIDAATQVCFSLGVGFGVLIAFSSYNKFTNNCYRDAIVTTSINSLTSFSS
GFVVFSFLGYMAQKHSVPIGDVAKDGPGLIFIIYPEAIATLPLSSAWAVVFFIMLLTLGI
DSAMGGMESVITGLIDEFQLLHRHRELFTLFIVLATFLLSLFCVTNGGIYVFTLLDHFAA
GTSILFGVLIEAIGVAWFYGVGQFSDDIQQMTGQRPSLYWRLCWKLVSPCFLLFVVVVSI
VTFRPPHYGAYIFPDWANALGWVIATSSMAMVPIYAAYKFCSLPGSFREKLAYAIAPEKD
RELVDRGEVRQFTLRHWLKV

Nucleic acid sequence of hDAT (SEQ ID NO: 27)

GAGCAAGTCCAAATGCAGCGTGGGACTGATGTCCAGCGTGGTTGCCCCCGCTAAGG
AGCCCAACGCCGTGGGCCCCAAGGAGGTGGAACTGATTCTCGTGAAGGAGCAGAACGGCG
TGCAGCTCACCTCCAGCACACTGACCAACCCTAGGCAGAGCCCCGTGGAGGCCCAGGACC
GGGAGACCTGGGGCAAGAAAATCGACTTCCTGCTCAGCGTGATCGGCTTCGCCGTCGACC
TGGCTAACGTTTGGCGGTTCCCCTACCTGTGCTACAAGAACGGCGGAGGCGCTTTCCTGG
TGCCCTACCTCCTCTTTATGGTGATCGCTGGCATGCCCCTGTTCTACATGGAGCTGGCCC
TCGGCCAGTTTAACCGGGAGGGAGCCGCAGGTGTGTGGAAGATTTGCCCCATCCTCAAAG
GCGTGGGATTCACCGTGATCCTGATCAGCCTGTACGTAGGCTTCTTTTACAACGTCATCA
TTGCCTGGGCTCTCCACTACCTGTTCTCGAGCTTCACCACAGAGCTGCCCTGGATCCACT
GCAACAATAGCTGGAACAGCCCCAACTGCAGCGATGCGCACCCCGGCGACAGCTCCGGAG
ACAGCTCAGGCCTGAACGACACCTTCGGAACCACACCCGCCGCTGAATACTTCGAACGGG
GCGTGCTGCACCTCCATCAGAGCCACGGCATCGATGACCTTGGTCCTCCCAGGTGGCAGC
TGACCGCCTGTCTGGTGCTCGTCATCGTGCTGCTCTACTTCAGCCTGTGGAAGGGCGTGA
AGACAAGCGGCAAGGTGGTCTGGATCACCGCCACAATGCCATATGTGGTCCTGACCGCCC
TGCTCCTGCGGGGGGTGACCCTGCCTGGGGCCATCGACGGCATTCGGGCCTACCTGAGCG
TGGACTTCTACCGGCTGTGCGAGGCTAGCGTGTGGATCGACGCTGCCACTCAAGTGTGCT
TCAGCCTGGGCGTGGGATTCGGGGTCCTGATCGCCTTCAGCTCCTACAACAAGTTCACCA
ACAATTGCTACCGCGACGCCATCGTCACCACAAGCATCAACTCCCTGACTAGTTTTTCGA
GCGGCTTTGTCGTGTTCAGCTTTCTGGGATACATGGCCCAGAAGCACAGCGTGCCCATCG
GTGACGTCGCCAAGGACGGCCCCGGGCTGATCTTCATTATCTACCCTGAGGCCATCGCTA
CCCTGCCCCTGAGCTCCGCCTGGGCTGTCGTGTTCTTTATCATGCTGCTCACCCTCGGCA
TCGACAGCGCTATGGGAGGCATGGAGAGCGTCATCACCGGCCTGATCGACGAATTCCAGC
TCCTGCACCGGCATCGCGAGCTGTTCACCCTGTTCATCGTGCTGGCCACCTTCCTTCTGA
GCCTGTTCTGCGTGACCAACGGCGGAATCTACGTGTTCACCCTCCTGGACCACTTCGCTG
CCGGCACCTCAATATTGTTCGGCGTGCTGATCGAGGCGATCGGCGTGGCCTGGTTCTACG
GAGTGGGCCAGTTCAGCGACGATATCCAGCAGATGACCGGTCAGCGGCCCAGCCTGTACT
GGCGGCTGTGCTGGAAGCTCGTCTCCCCCTGCTTCCTCCTGTTCGTGGTCGTTGTGTCAA
TTGTGACCTTCCGGCCTCCCCACTACGGCGCCTACATCTTCCCCGACTGGGCCAATGCAT
TGGGCTGGGTGATCGCAACCAGCTCCATGGCTATGGTGCCCATCTACGCTGCCTACAAGT
TCTGTAGCCTGCCCGGAAGCTTCCGGGAGAAGCTGGCGTACGCTATCGCCCCCGAGAAGG
ACCGGGAGCTGGTGGACCGCGGCGAGGTGCGGCAGTTCACCCTGCGGCACTGGCTGAAGG
TGTGA

FIGURE 9 – CONT.

Fusion of RQR8 with codon optimized hDAT

Protein Sequence of RQR8hDAT (SEQ ID NO: 7)

SLLCWMALCLLGADHADACPYSNPSLCSGGGGSELPTQGTFSNVSTNVSPAKPTTTACPY
SNPSLCSGGGGSPAPRPPTPAPTIASQPLSLRPEACRPAAGGAVHTRGLDFACDIYIWAP
LAGTCGVLLLSLVITLYCNHRNRRRVCKCPRPVVSSTLTNPRQSPVEAQDRETWGKKIDF
LLSVIGFAVDLANVWRFPYLCYKNGGGAFLVPYLLFMVIAGMPLFYMELALGQFNREGAA
GVWKICPILKGVGFTVILISLYVGFFYNVIIAWALHYLFSSFTTELPWIHCNNSWNSPNC
SDAHPGDSSGDSSGLNDTFGTTPAAEYFERGVLHLHQSHGIDDLGPPRWQLTACLVLVIV
LLYFSLWKGVKTSGKVVWITATMPYVVLTALLLRGVTLPGAIDGIRAYLSVDFYRLCEAS
VWIDAATQVCFSLGVGFGVLIAFSSYNKFTNNCYRDAIVTTSINSLTSFSSGFVVFSFLG
YMAQKHSVPIGDVAKDGPGLIFIIYPEAIATLPLSSAWAVVFFIMLLTLGIDSAMGGMES
VITGLIDEFQLLHRHRELFTLFIVLATFLLSLFCVTNGGIYVFTLLDHFAAGTSILFGVL
IEAIGVAWFYGVGQFSDDIQQMTGQRPSLYWRLCWKLVSPCFLLFVVVVSIVTFRPPHYG
AYIFPDWANALGWVIATSSMAMVPIYAAYKFCSLPGSFREKLAYAIAPEKDRELVDRGEV
RQFTLRHWLKV

FIGURE 9 – CONT.

Nucleic acid sequence of hDAT (SEQ ID NO: 28)

```
TGGGCACCAGCCTGCTGTGCTGGATGGCCCTGTGCCTGCTGGGCGCCGACCACGCC
GATGCCTGCCCCTACAGCAACCCCAGCCTGTGCAGCGGAGGCGGCGGCAGCGAGCTGCCC
ACCCAGGGCACCTTCTCCAACGTGTCCACCAACGTGAGCCCAGCCAAGCCCACCACCACC
GCCTGTCCTTATTCCAATCCTTCCCTGTGTAGCGGAGGGGGAGGCAGCCCAGCCCCCAGA
CCTCCCACCCCAGCCCCCACCATCGCCAGCCAGCCTCTGAGCCTGAGACCCGAGGCCTGC
CGCCCAGCCGCCGGCGGCGCCGTGCACACCAGAGGCCTGGATTTCGCCTGCGATATCTAC
ATCTGGGCCCCACTGGCCGGCACCTGTGGCGTGCTGCTGCTGAGCCTGGTGATCACCCTG
TACTGCAACCACCGCAACCGCAGGCGCGTGTGCAAGTGCCCCAGGCCCGTGGTGAGCAGC
ACCCTGACCAACCCTAGACAGAGCCCCGTGGAGGCCCAGGACCGGGAGACCTGGGGCAAG
AAGATCGACTTCCTGCTGAGCGTGATCGGCTTCGCCGTGGACCTGGCCAACGTGTGGCGG
TTCCCCTACCTGTGCTACAAGAACGGCGGAGGCGCCTTCCTGGTGCCCTACCTGCTGTTC
ATGGTGATCGCCGGCATGCCTCTGTTCTACATGGAGCTGGCCCTGGGCCAGTTCAACCGG
GAGGGCGCCGCCGGCGTGTGGAAAATCTGCCCTATCCTGAAGGGCGTGGGCTTCACCGTG
ATCCTGATCAGCCTGTACGTGGGCTTCTTCTACAACGTGATCATCGCCTGGGCCCTGCAC
TACCTGTTCAGCAGCTTCACCACCGAGCTGCCCTGGATTCACTGCAACAACAGCTGGAAC
AGCCCCAACTGCAGCGACGCCCACCCCGGCGACAGCAGCGGCGACAGCAGCGGCCTGAAC
GACACCTTCGGCACCACCCCAGCCGCCGAGTACTTCGAGCGCGGCGTGCTGCACCTGCAC
CAGAGCCACGGCATCGACGACCTGGGCCCACCTCGGTGGCAGCTGACCGCCTGCCTGGTG
CTGGTGATCGTGCTGCTGTACTTCAGCCTGTGGAAGGGCGTGAAGACCAGCGGCAAGGTG
GTGTGGATCACCGCCACCATGCCCTACGTGGTGCTGACCGCCCTGCTGCTGCGCGGCGTG
ACCCTGCCCGGCGCCATCGACGGCATCCGGGCCTACCTGAGCGTGGACTTCTACCGGCTG
TGCGAGGCCAGCGTGTGGATCGACGCCGCCACCCAGGTGTGCTTCAGCCTGGGCGTGGGC
TTCGGCGTGCTGATCGCCTTCAGCAGCTACAACAAGTTCACCAACAACTGCTACCGGGAC
GCCATCGTGACCACCAGCATCAACAGCCTGACCAGCTTCAGCAGCGGCTTCGTGGTGTTC
AGCTTCCTGGGCTACATGGCCCAGAAGCACAGCGTGCCCATCGGCGACGTGGCCAAGGAC
GGTCCCGGCCTGATCTTCATCATCTACCCCGAGGCCATCGCCACCCTGCCCCTGAGCAGC
GCCTGGGCCGTGGTGTTCTTCATCATGCTGCTGACCCTGGGCATCGACAGCGCTATGGGC
GGCATGGAGAGCGTGATCACCGGCCTGATCGACGAGTTCCAGCTGCTGCACCGGCACCGG
GAGCTGTTCACCCTGTTCATCGTGCTGGCCACCTTCCTGCTGAGCCTGTTCTGCGTGACC
AACGGCGGCATCTACGTGTTCACCCTGCTGGACCACTTCGCCGCCGGCACCAGCATCCTG
TTCGGCGTGCTGATCGAGGCCATCGGCGTGGCCTGGTTCTACGGCGTGGGTCAGTTCAGC
GACGACATCCAGCAGATGACCGGCCAGCGGCCCAGCCTGTACTGGCGGCTGTGCTGGAAG
CTGGTGAGCCCTTGCTTCCTGCTGTTCGTGGTGGTGGTGAGCATCGTGACCTTCCGGCCA
CCTCACTACGGCGCCTACATCTTCCCCGACTGGGCCAACGCCCTGGGCTGGGTGATCGCC
ACCAGCAGCATGGCTATGGTGCCCATCTACGCCGCCTACAAGTTCTGCAGCCTGCCCGGC
AGCTTCCGCGAGAAGCTGGCCTACGCCATCGCCCCAGAGAAGGACCGGGAGCTGGTGGAC
CGCGGCGAGGTGCGGCAGTTCACCCTGCGGCACTGGCTGAAGGTGTGA
```

FIGURE 9 – CONT.

Codon optimized hDAT with D313N mutation 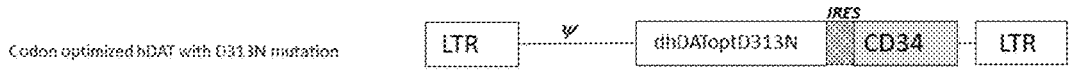

Protein Sequence of dhDATopt313N (SEQ ID NO: 8)

MSKSKCSVGLMSSVVAPAKEPNAVGPKEVELILVKEQNGVQLTSSTLTNPRQSPVEAQDR
ETWGKKIDFLLSVIGFAVDLANVWRFPYLCYKNGGGAFLVPYLLFMVIAGMPLFYMELAL
GQFNREGAAGVWKICPILKGVGFTVILISLYVGFFYNVIIAWALHYLFSSFTTELPWIHC
NNSWNSPNCSDAHPGDSSGDSSGLNDTFGTTPAAEYFERGVLHLHQSHGIDDLGPPRWQL
TACLVLVIVLLYFSLWKGVKTSGKVVWITATMPYVVLTALLLRGVTLPGAIDGIRAYLSV
DFYRLCEASVWINAATQVCFSLGVGFGVLIAFSSYNKFTNNCYRDAIVTTSINSLTSFSS
GFVVFSFLGYMAQKHSVPIGDVAKDGPGLIFIIYPEAIATLPLSSAWAVVFFIMLLTLGI
DSAMGGMESVITGLIDEFQLLHRHRELFTLFIVLATFLLSLFCVTNGGIYVFTLLDHFAA
GTSILFGVLIEAIGVAWFYGVGQFSDDIQQMTGQRPSLYWRLCWKLVSPCFLLFVVVSI
VTFRPPHYGAYIFPDWANALGWVIATSSMAMVPIYAAYKFCSLPGSFREKLAYAIAPEKD
RELVDRGEVRQFTLRHWLKV

Nucleic acid sequence of dhDATopt313N (SEQ ID NO: 29)

GAGCAAGAGCAAGTGCAGCGTGGGCCTGATGAGCAGCGTGGTGGCCCCAG
CCAAGGAGCCCAACGCCGTGGGCCCTAAGGAGGTGGAGCTGATCCTGGTGAAGGAGCAGA
ACGGCGTGCAGCTGACCAGCAGCACCCTGACCAACCCTAGACAGAGCCCCGTGGAGGCCC
AGGACCGGAGACCTGGGGCAAGAAGATCGACTTCCTGCTGAGCGTGATCGGCTTCGCCG
TGGACCTGGCCAACGTGTGGCGGTTCCCCTACCTGTGCTACAAGAACGGCGGAGGCGCCT
TCCTGGTGCCCTACCTGCTGTTCATGGTGATCGCCGGCATGCCTCTGTTCTACATGGAGC
TGGCCCTGGGCCAGTTCAACCGGGAGGGCGCCGCCGGCGTGTGGAAAATCTGCCCTATCC
TGAAGGGCGTGGGCTTCACCGTGATCCTGATCAGCCTGTACGTGGGCTTCTTCTACAACG
TGATCATCGCCTGGGCCCTGCACTACCTGTTCAGCAGCTTCACCACCGAGCTGCCCTGGA
TTCACTGCAACAACAGCTGGAACAGCCCCAACTGCAGCGACGCCCACCCCGGCGACAGCA
GCGGCGACAGCAGCGGCCTGAACGACACCTTCGGCACCACCCCAGCCGCCGAGTACTTCG
AGCGCGGCGTGCTGCACCTGCACCAGAGCCACGGCATCGACGACCTGGGCCCACCTCGGT
GGCAGCTGACCGCCTGCCTGGTGCTGGTGATCGTGCTGCTGTACTTCAGCCTGTGGAAGG
GCGTGAAGACCAGCGGCAAGGTGGTGTGGATCACCGCCACCATGCCCTACGTGGTGCTGA
CCGCCCTGCTGCTGCGCGGCGTGACCCTGCCCGGCGCCATCGACGGCATCCGGGCCTACC
TGAGCGTGGACTTCTACCGGCTGTGCGAGGCCAGCGTGTGGATCAACGCCGCCACCCAGG
TGTGCTTCAGCCTGGGCGTGGGCTTCGGCGTGCTGATCGCCTTCAGCAGCTACAACAAGT
TCACCAACAACTGCTACCGGGACGCCATCGTGACCACCAGCATCAACAGCCTGACCAGCT
TCAGCAGCGGCTTCGTGGTGTTCAGCTTCCTGGGCTACATGGCCCAGAAGCACAGCGTGC
CCATCGGCGATGGCCAAGGACGGTCCCGGCCTGATCTTCATCATCTACCCCGAGGCCA
TCGCCACCCTGCCCCTGAGCAGCGCCTGGGCCGTGGTGTTCTTCATCATGCTGCTGACCC
TGGGCATCGACAGCGCTATGGGCGGCATGGAGAGCGTGATCACCGGCCTGATCGACGAGT
TCCAGCTGCTGCACCGGCACCGGGAGCTGTTCACCCTGTTCATCGTGCTGGCCACCTTCC
TGCTGAGCCTGTTCTGCGTGACCAACGGCGGCATCTACGTGTTCACCCTGCTGGACCACT
TCGCCGCCGGCACCAGCATCCTGTTCGGCGTGCTGATCGAGGCCATCGGCGTGGCCTGGT
TCTACGGCGTGGGTCAGTTCAGCGACGACATCCAGCAGATGACCGGCCAGCGGCCCAGCC
TGTACTGGCGGCTGTGCTGGAAGCTGGTGAGCCCTTGCTTCCTGCTGTTCGTGGTGGTGG
TGAGCATCGTGACCTTCCGGCCACCTCACTACGGCGCCTACATCTTCCCCGACTGGGCCA
ACGCCCTGGGCTGGGTGATCGCCACCAGCAGCATGGCTATGGTGCCCATCTACGCCGCCT
ACAAGTTCTGCAGCCTGCCCGGCAGCTTCCGCGAGAAGCTGGCCTACGCCATCGCCCAG
AGAAGGACCGGGAGCTGGTGGACCGCGGCGAGGTGCGGCAGTTCACCCTGCGGCACTGGC
TGAAGGTGTGA d2 post aCD19 CAR T-cells d4 post T cell aCD19 CAR T-cells d7 post T cell aCD19 CAR T-cells

DETECTING A THERAPEUTIC CELL

FIELD OF THE INVENTION

The present invention relates to methods and reagents which can be used to enable the detection of a therapeutic cell in the central nervous system of a subject.

BACKGROUND TO THE INVENTION

Malignant brain tumours are rapidly progressive and resistant to most treatments. In the last eighty years, long-term survival has improved from just six to eighteen months even with state-of-the-art standard of care (surgery, chemotherapy, and radiotherapy). Neurodegenerative disease such as Parkinson's Disease and Alzheimer's Disease also represent unmet clinical needs.

With the promise of new cell based therapies, there is an urgent need for non-invasive, readily available and translatable methods of detecting and quantifying cells in vivo. The development of this imaging technology will enable visualization of biological processes where the fate, localization and long term viability of therapeutic cells can be monitored, which will greatly increase the value of clinical exploration in this area.

By way of example, T-cell therapy, particularly chimeric antigen receptor (CAR) therapy, is an extremely promising cellular therapy that has demonstrated remarkable efficacy in oncological research and clinical practice. Nevertheless, the fate of the therapeutic T cells in clinical studies remains unclear, particularly in central nervous system (CNS) where the engraftment of the T-cells is appreciably more challenging to measure. Despite the continued advancements in monitoring reporter gene expressing T-cells in the peripheral nervous system there is no translatable or clinical standard for tracking cells in the CNS, in particular in the brain.

When assessing CAR T-cell targeting B-cell malignancies, it is possible to sample sites of CAR T-cell activity: i.e. peripheral blood, marrow and even lymph-nodes. This is clearly not possible with CNS disease and information regarding the biodistribution of the therapeutic cells is not provided. In human subjects, MRI and nuclear imaging approaches have been developed to track cellular therapies. These methods typically rely on transient (direct) labelling, for instance, tagging cells with paramagnetic iron oxide particles (for MRI), or with radiotracers (SPECT/PET). However, these transient labelling approaches are not well suited to CAR T-cell tracking as dilution of contrast agent during cell division and/or its radioactive decay confines imaging to a short window after administration, and as such, limits visualisation of the long-term viability of therapeutic cells.

There is thus a need for improved methods of detecting therapeutic cells, for example CAR-expressing cells, in the CNS of a subject.

SUMMARY OF ASPECTS OF THE INVENTION

The present inventors have surprisingly found that it is possible to detect a therapeutic cell in the central nervous system (CNS) of a subject by engineering the cell to express dopamine transporter (DAT) and detecting the presence of the engineered therapeutic cell using a DAT tracer.

Accordingly, in a first aspect the present invention relates to a method of detecting a therapeutic cell expressing a DAT at a CNS site in a subject, which comprises the administration of a DAT tracer to the subject, wherein the presence of a therapeutic cell which express the DAT is determined.

The method may comprise the steps of: i) administering a therapeutic cell expressing a DAT or a therapeutic vector encoding a DAT to the subject; ii) administering a DAT tracer to the subject; and iii) determining the presence of a therapeutic cell expressing the DAT in the CNS of the subject.

The DAT tracer may be [$^{123}$I]-FP-CIT (Ioflupane; [I-$^{123}$] N-ω-fluoropropyl-2β-carbomethoxy-3β-(4-iodophenyl) nortropane) or [$^{18}$F]-FP-CIT ([$^{18}$F] fluoropropyl-carbomethoxy-iodophenyl-nortropane).

The presence of a therapeutic cell expressing DAT may be determined by single-photon emission computed tomography (SPECT) or positron emission tomography (PET).

The DAT may comprise the sequence shown as SEQ ID NO: 1, 4, 5, 6, 7 or 8 or a variant thereof with at least 80% sequence identity.

The CNS site may be in the brain of the subject.

The presence of a therapeutic cell expressing DAT may be determined at least 72 hours after the therapeutic cell or therapeutic vector has been administered to the subject.

The therapeutic cell may be an immune effector cell. The immune effector cell may express a chimeric antigen receptor (CAR).

In another aspect the present invention relates to the use of a DAT tracer to detect a therapeutic cell expressing a DAT at a CNS site in a subject. The use may comprise performing a method as defined in the first aspect of the invention.

In a further aspect the present invention provides a DAT which consists of the sequence shown as SEQ ID NO: 4 or 5 or a variant thereof with at least 80% sequence identity or comprises the sequence shown as SEQ ID NO: 7 or a variant thereof with at least 80% sequence identity.

In a further aspect the present invention provides a nucleic acid sequence encoding a DAT, said DAT consisting of the sequence shown as SEQ ID NO: 4 or 5 or a variant thereof with at least 80% sequence identity or comprising the sequence shown as SEQ ID NO: 7 or a variant thereof with at least 80% sequence identity.

In a further aspect the present invention provides a nucleic acid sequence encoding a DAT and a CAR. Here, the nucleic acid sequence may encode a DAT which comprises the sequence shown as SEQ ID NO: 1, 4, 5, 6, 7 or 8 or a variant thereof with at least 80% sequence identity.

The nucleic acid sequence may have the following structure:

DAT'-coexpr-CAR' or CAR'-coexpr-DAT' in which DAT' is a nucleic acid sequence encoding the DAT; CAR' is a nucleic acid sequence encoding the CAR; and coexpr is a nucleic acid sequence enabling the co-expression of both the DAT and the CAR.

The coexpr nucleic acid sequence may encode a sequence comprising a self-cleaving peptide or an internal ribosome entry site (IRES).

The nucleic acid sequence may further comprise a nucleic acid sequence encoding a suicide gene.

In a further aspect the present invention provides a therapeutic vector comprising a nucleic acid sequence encoding a DAT, said DAT comprising the sequence shown as SEQ ID NO: 1, 4, 5, 6, 7 or 8 or a variant thereof with at least 80% sequence identity and a therapeutic nucleic acid sequence.

In another aspect the present invention provides a vector comprising a nucleic acid sequence encoding a DAT, said DAT consisting of the sequence shown as SEQ ID NO: 4 or 5 or a variant thereof with at least 80% sequence identity or comprising the sequence shown as SEQ ID NO: 7 or a variant thereof with at least 80% sequence identity.

The vectors of the present invention may be a retroviral vector, a lentiviral vector, a plasmid or a transposon.

In a further aspect the present invention provides a therapeutic cell expressing a DAT. The DAT may comprise the sequence shown as SEQ ID NO: 1, 4, 5, 6, 7 or 8 or a variant thereof with at least 80% sequence identity.

The therapeutic cell may be an immune effector cell. The immune effector cell may further express a CAR.

In a further aspect the present invention provides a therapeutic cell comprising a nucleic acid sequence or a vector provided by the present invention.

In another aspect the present invention relates to a method of making a therapeutic cell of the present invention, which comprises the step of introducing a nucleic acid sequence or a vector as described herein into a therapeutic cell.

The cell may be isolated from a subject.

In a further aspect the present invention relates to the use of a nucleic acid, a vector or a therapeutic cell according to present invention in a method as defined by the first aspect of the invention.

In a further aspect the present invention relates to the use of a nucleic acid or a vector according to the present invention for the preparation of a therapeutic cell.

In another aspect the present invention relates to a nucleic acid or a vector according to the present invention for use in the preparation of a therapeutic cell.

In another aspect the present invention relates to the use of a therapeutic cell according to the present invention in combination with a DAT tracer for determining the presence of said therapeutic cell at a site in the CNS.

In a further aspect the present invention provides a combination of a therapeutic cell according to the present invention and a DAT tracer for use in determining the presence of said therapeutic cell at a site in the CNS.

In a further aspect the present invention relates to the use of a therapeutic vector according to the present invention in combination with a DAT tracer for determining the presence of a therapeutic cell expressing DAT at a site in the CNS.

In another aspect the present invention provides a therapeutic vector according to the present invention in combination with a DAT tracer for use in determining the presence of a therapeutic cell expressing DAT at a site in the CNS.

In another aspect the present invention provides a pharmaceutical composition comprising a therapeutic cell or a therapeutic vector according to the present invention and a pharmaceutically acceptable excipient or carrier.

In another aspect the present invention relates to a pharmaceutical composition according to the present invention for use in treating and/or preventing a disease.

In another aspect the present invention provides the use of a therapeutic cell or a therapeutic vector according to the present invention in the manufacture of a medicament for treating and/or preventing a disease.

In a further aspect the present invention relates to a method of treating and/or preventing a disease which comprises the step of administering a therapeutic cell or therapeutic vector according to the present invention to a subject in need thereof.

The present invention therefore enables therapeutic cells in the CNS to be detected and/or quantified. Examples of such therapeutic cells include therapeutic cells which are administered to a subject as a medicament, and host cells in the subject which have been subjected to gene therapy in order to express a therapeutic nucleic acid sequence. The present invention thus enables the fate and longevity of therapeutic cells in the CNS to be determined.

DESCRIPTION OF THE FIGURES

FIG. 4—Time activity profile—hDAT-positive xenograft bearing NSG mice (n=4) were intravenously injected with 16.76±1.45 MBq (250 ul) of [$^{123}$I]-FP-CIT.

DETAILED DESCRIPTION

Therapeutic Cell

Figure 1A:
FIG. 1—Engineering of hDAT expressing T cells and [$^{123}$I]-FP-CIT radiotracer binding—(FIG. 1a) Schematic structure of the bicistronic retroviral vector encoding hDAT and CD34 genes linked by an IRES sequence. Reporter gene expression is driven by the Moloney murine leukemia virus (Mo-MuLV) long terminal repeat (LTR) promoter.
(FIG. 1b) FACS analysis of sorted SupT1/SFG.hDAT.I.CD34 cells co-transduced with FLuc.
(FIG. 1c) The structure of [$^{123}$I]-FP-CIT/DaTSCAN (FIG. 1d) % [$^{123}$I]-FP-CIT binding was 27 fold greater in SupT1/SFG.hDAT.I.CD34 cells (n=11) compared to control cells (n=8). [$^{123}$I]-FP-CIT binding was completely abolished in hDAT positive T-cells (n=12) following co-incubation with the cold compound ([I]-FP-CIT; 50 μm). Cells were incubated with 7.4 kBq of [$^{123}$I]-FP-CIT at 37° C. for 30 min. Experiments were repeated ≥twice, *p<0.001 and values are means±SD.
(FIG. 1e) Comparison of % [$^{123}$I]-FP-CIT binding 10 minutes and 1 hour after co-incubation FIG. 2—hDAT expressing primary T cells retain their function—(FIG. 2a-FIG. 2c) The transduction efficiencies of EBV-CTL/SFG.hDAT.I.CD34, EBV-CTL/SFG.V5-HA1-TCRβ_opt.I.CD34 compared to non-transduced cells (NT/EBV-CTL). EBV-CTLs were stimulated with autologous, irradiated B-LCLs for 4 days and proliferation was tested by H$^3$-thymidine uptake for 21 h. IFN-γ secretion was assessed by ELISA 24 h post stimulation. EBV-CTL/SFG.hDAT.I.OD34 cells were able to proliferate (FIG. 2d) and secrete IFN-γ (FIG. 2e) in the presence of autologous LCLs at comparable levels to NT/EBV-CTLs and EBV-CTL/SFG.V5-HA1-TCRβ_opt.I.CD34. Data is obtained from 3 donors, *p<0.001 and values are means±SD (n=3).

In a first aspect the present invention relates to a method of detecting therapeutic cells expressing DAT at a CNS site in a subject.

The term 'detect', as used herein, is synonymous with terms such as identify, observe and visualise. Thus the method of the present invention determines the presence of therapeutic cells expressing DAT based on the binding of a DAT tracer to those cells.

The term 'detect' may also encompass a method of quantifying therapeutic cells. Quantifying refers to a method which enables the 'level' or 'amount' of therapeutic cells to be determined.

A therapeutic cell refers to a cell which provides a beneficial effect to a subject suffering from a disease, for example a cell which lessens, reduces or improves at least one symptom associated with the disease and/or slows down, reduces or blocks the progression of the disease.

The therapeutic cell may be a cell which is administered to the subject in the form of a medicament or a host cell of the subject which has been treated in vivo with a therapeutic vector in order to express a therapeutic nucleic acid sequence.

Accordingly, the therapeutic cell may be a cell which is administered to a subject in the form of a medicament, for example in the form of a pharmaceutical composition of the present invention. Such therapeutic cells are administered to a subject in order to lessen, reduce or improve at least one symptom associated with a disease and/or to slow down, reduce or block the progression of a disease.

The therapeutic cell may be an immune effector cell or a therapeutic stem cell.

In one embodiment the administration or use of a therapeutic cell refers to an immune effector cell or a therapeutic stem cell.

The therapeutic cell may be an immune effector cell.

As used herein, an 'immune effector cell' refers to an immune cell which is capable of providing an immunological function. For example, the immune effector cell may be capable of providing an cytotoxic function.

The immune effector cell may be a T cell or a natural killer (NK cell).

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. The T cell or NK cell may be a cell as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytotoxic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The T cell of the invention may be any of the T cell types mentioned above, in particular a CTL.

Natural killer (NK) cells are a type of cytolytic cell which forms part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The therapeutic cell may be a therapeutic stem cell. The therapeutic stem cell may be a pluripotent stem cell.

The therapeutic stem cell may be a multipotent stem cell. For example, the stem cell may be a neural stem/precursor cell (NSPC). NSPCs are self-renewing, multipotent cells that generate the main phenotype of the nervous system. The use of NSPCs for the treatment of neurodegenerative disorders is described, for example, by Latchney et al. (Eur J Neurodegener Dis. 2012; 1(3): 335-351; incorporated herein by reference).

The therapeutic cell may be a CNS cell of the subject which has been treated with a therapeutic vector such that it expresses a therapeutic nucleic acid. Accordingly, the therapeutic vector comprises a nucleic acid sequence encoding a DAT protein as described herein and a therapeutic nucleic acid sequence.

The therapeutic nucleic acid sequence is not limited and may be, for example, a protein encoding nucleic acid sequence, a miRNA sequence or a long non-coding RNA.

The use of a therapeutic vector according to the present invention allows cells which have taken up the therapeutic vector, and are therefore expressing the therapeutic nucleic acid, to be detected and quantified using the method as defined in the first aspect of the present invention. This enables the effectiveness of a gene therapy method to be assessed.

Dopamine Transporter (DAT)

The dopamine transporter (also dopamine active transporter, DAT, SLC6A3) is a membrane-spanning protein that actively transports the neurotransmitter dopamine out of the synapse into cytosol. Dopamine reuptake via DAT provides the primary mechanism through which dopamine is cleared from synapses, although there may be an exception in the prefrontal cortex, where evidence points to a possible larger role of the norepinephrine transporter.

The initial determination of the membrane topology of DAT was based upon hydrophobic sequence analysis and sequence similarities with the GABA transporter. These methods predicted twelve transmembrane domains (TMD) with a large extracellular loop between the third and fourth TMDs. Further characterization of this protein used proteases, which digest proteins into smaller fragments, and glycosylation, which occurs only on extracellular loops, and largely verified the initial predictions of membrane topology. The exact structure of the transporter was elucidated in 2013 by X-ray crystallography.

The human DAT is expressed exclusively in the pre-synaptic membrane of dopaminergic neurons (see Kim et al; 2002; Nature; 418: 50-56). It is highly expressed in the substantia nigra.

As such, the therapeutic cells as described herein may naturally express DAT. Preferably, the therapeutic cells as described herein may be engineered to express a DAT protein.

An example human DAT protein (hDAT) is the human DAT protein having the UniProtKB accession number Q01959-1. This exemplified sequence is 620 amino acids in length and is shown as SEQ ID NO: 1.

```
                                                SEQ ID NO: 1
MSKSKCSVGLMSSVVAPAKEPNAVGPKEVELILVKEQNGVQLTSSTL

TNPRQSPVEAQDRETWGKKIDFLLSVIGFAVDLANVWRFPYLCYKNG

GGAFLVPYLLFMVIAGMPLFYMELALGQFNREGAAGVWKICPILKGV

GFTVILISLYVGFFYNVIIAWALHYLFSSFTTELPWIHCNNSWNSPN

CSDAHPGDSSGDSSGLNDTFGTTPAAEYFERGVLHLHQSHGIDDLGP

PRWQLTACLVLVIVLLYFSLWKGVKTSGKVVWITATMPYVVLTALLL

RGVTLPGAIDGIRAYLSVDFYRLCEASVWIDAATQVCFSLGVGFGVL

-continued
IAFSSYNKFTNNCYRDAIVTTSINSLTSFSSGFVVFSFLGYMAQKHS

VPIGDVAKDGPGLIFIIYPEAIATLPLSSAWAVVFFIMLLTLGIDSA

MGGMESVITGLIDEFQLLHRHRELFTLFIVLATFLLSLFCVTNGGIY

VFTLLDHFAAGTSILFGVLIEAIGVAWFYGVGQFSDDIQQMTGQRPS

LYWRLCWKLVSPCFLLFVVVVSIVTFRPPHYGAYIFPDWANALGWVI

ATSSMAMVPIYAAYKFCSLPGSFREKLAYAIAPEKDRELVDRGEVRQ

FTLRHWLKV
```

An alternative human DAT protein is shown as SEQ ID NO: 6 (see FIG. 9). This sequence lacks the N-terminal 'M' and 'S' residues in comparison to SEQ ID NO: 1.

In one embodiment, the DAT protein may be a variant DAT protein. A variant DAT protein may be any DAT protein which is capable of binding a DAT tracer which binds to SEQ ID NO: 1 or 6.

The DAT variant protein may be capable of binding a DAT tracer at the same or an increased level compared to the DAT protein shown as SEQ ID NO: 1 or 6.

The variant protein may comprise mutations, deletions or additional amino acids compared to SEQ ID NO: 1 or 6 providing that the variant is capable of binding a DAT tracer which binds to SEQ ID NO: 1 or 6.

The DAT protein as described herein may comprise the sequence shown as SEQ ID NO: 1 or 6 or a variant thereof having at least 80% sequence identity which is capable of binding a DAT tracer which binds to SEQ ID NO: 1 or 6.

The variant may have at least 80, 85, 90, 95 or 99% sequence identity to SEQ ID NO: 1 or 6 and be capable of binding a DAT tracer which binds to SEQ ID NO: 1 or 6.

The present inventors have determined DAT truncation mutants which are capable of functional binding of DAT tracers.

Accordingly, the DAT protein may be a truncated DAT protein.

The truncated DAT may be a DAT which has a number of amino acids removed from either the N or C terminus in comparison to SEQ ID NO: 1.

The number of amino acids removed from the N-terminus may be less than 5, less than 10, less than 20, less than 30, less than 40 or less than 50 amino acids.

The DAT protein may lack the first 50 amino acids from the N-terminus with reference to the DAT sequence shown as SEQ ID NO: 1 or a variant thereof having at least 80% sequence identity.

An example of such a DAT protein is shown as SEQ ID NO: 4 (see FIG. 9).

The DAT protein described herein may have a sequence as shown in SEQ ID NO: 4 or a variant thereof having at least 80% sequence identity and retaining the ability to bind a DAT tracer which binds to the wild type DAT protein.

The variant may have at least 80, 85, 90, 95 or 99% sequence identity to SEQ ID NO: 4.

The number of amino acids removed from the C-terminus may be less than 5, less than 7, less than 10, less than 14 or less than 19 amino acids.

The DAT protein may lack the final 19 amino acids from the C-terminus with reference to the DAT sequence shown as SEQ ID NO: 1 or a variant thereof having at least 80% sequence identity.

An example of such a DAT protein is shown as SEQ ID NO: 5 (see FIG. 9).

The DAT protein described herein may have a sequence as shown in SEQ ID NO: 5 or a variant thereof having at least 80% sequence identity and retaining the ability to bind a DAT tracer which binds to the wild type DAT protein.

The variant may have at least 80, 85, 90, 95 or 99% sequence identity to SEQ ID NO: 5.

The truncated DAT may be a DAT which has a number of amino acids removed from the N and C terminus in comparison to SEQ ID NO: 1.

The number of amino acids removed from the N-terminus may be less than 5, less than 10, less than 20, less than 30, less than 40 or less than 50 amino acids.

The number of amino acids removed from the C-terminus may be less than 5, less than 7, less than 10, less than 14 or less than 19 amino acids.

The truncated DAT may lack the first 50 amino acids from the N terminus in comparison to SEQ ID NO: 1 and the final 19amino acids from the C terminus in comparison to SEQ ID NO: 1.

A number of DAT mutations which increase the relative binding of dopamine to DAT have been described.

The DAT protein described herein may therefore include a mutation which maintains or increases the binding of dopamine or a DAT tracer to DAT compared to SEQ ID NO: 1 or 6. By way of example, the DAT protein may comprise a D313N and/or W84L mutation with reference to the DAT sequence shown as SEQ ID NO: 1 or a variant thereof having at least 80% sequence identity.

An example of such a DAT protein is shown as SEQ ID NO: 8 (see FIG. 9). This DAT protein comprises a D313N mutation with reference to the DAT sequence shown as SEQ ID NO: 1

The DAT protein may comprise a D313N mutation with reference to the DAT sequence shown as SEQ ID NO: 1 or a variant thereof having at least 80% sequence identity. The variant may have at least 80, 85, 90, 95 or 99% sequence identity to SEQ ID NO: 1.

For example the DAT protein may comprise the sequence shown as any of SEQ ID NO: 1, 4, 5, 6, 7 or 8 and further include a D313N and/or W84L mutation with reference to the DAT sequence shown as SEQ ID NO: 1 or a variant thereof having at least 80% sequence identity.

The DAT protein may comprise the sequence shown as any of SEQ ID NO: 1, 4, 5, 6 or 7 and further include a D313N mutation with reference to the DAT sequence shown as SEQ ID NO: 1 or a variant thereof having at least 80% sequence identity.

The DAT protein may comprise the sequence shown as any of SEQ ID NO: 1, 4, 5, 6, 7 or 8 and further include a D313N mutation with reference to the DAT sequence shown as SEQ ID NO: 1 or a variant thereof having at least 80% sequence identity.

The variant may have at least 80, 85, 90, 95 or 99% sequence identity to SEQ ID NO: 1 and further include a D313N and/or W84L mutation with reference to the DAT sequence shown as SEQ ID NO: 1.

The variant may have at least 80, 85, 90, 95 or 99% sequence identity to SEQ ID NO: 4 and further include a D313N and/or W84L mutation with reference to the DAT sequence shown as SEQ ID NO: 1.

The variant may have at least 80, 85, 90, 95 or 99% sequence identity to SEQ ID NO: 5 and further include a D313N and/or W84L mutation with reference to the DAT sequence shown as SEQ ID NO: 1.

The variant may have at least 80, 85, 90, 95 or 99% sequence identity to SEQ ID NO: 6 and further include a D313N and/or W84L mutation with reference to the DAT sequence shown as SEQ ID NO: 1.

The variant may have at least 80, 85, 90, 95 or 99% sequence identity to SEQ ID NO: 7 and further include a D313N and/or W84L mutation with reference to the DAT sequence shown as SEQ ID NO: 1.

The variant may have at least 80, 85, 90, 95 or 99% sequence identity to SEQ ID NO: 8 and further include W84L mutation with reference to the DAT sequence shown as SEQ ID NO: 1.

In one embodiment, the DAT protein does not include a deletion from amino acids 519 to 620 with reference to the DAT sequence shown as SEQ ID NO: 1.

The DAT protein or nucleic acid sequence encoding the DAT protein may comprise, consist essentially of or consist of a DAT protein or nucleic acid sequence as described herein.

DAT Tracer

As used herein a DAT tracer refers to an entity which binds DAT and can be detected using, for example, an imaging technique.

Such tracers are typically radiotracers. Suitable DAT tracers are known in the art. By way of example, we refer to Piccini (Movement Disorders; 2003; vol 18:7; pp S3-8) and Shen et al. (Journal of Biomedicine and Biotechnology; 2012; Article ID 259349)—both of which are incorporated herein by reference.

Known DAT radiotracers include, but are not limited to, $^{11}$C-CFT, $^{18}$F-CFT, $^{11}$C-PE2I, $^{123}$I-β-CIT, [$^{123}$I]-FP-CIT (Ioflupane; [I-123] N-ω-fluoropropyl-2β-carbomethoxy-3β-(4-iodophenyl) nortropane) and [$^{18}$F]-FP-CIT ([$^{18}$F] fluoropropyl-carbomethoxy-iodophenyl-nortropane).

Ioflupane is also known as DaTSCAN™.

Radiotracers may be detected using imaging techniques which are known in the art, for example single-photon emission computed tomography (SPECT) or positron emission tomography (PET).

The method according to the first aspect of the present invention may comprise the steps of;
 i) administering a therapeutic vector encoding a DAT or a therapeutic cell expressing a DAT to the subject;
 ii) administering a DAT tracer to the subject; and
 iii) determining the presence of a therapeutic cell expressing the DAT in the CNS of the subject.

A therapeutic cell or a therapeutic vector may be administered to the subject in the form of a pharmaceutically acceptable composition, for example a pharmaceutical composition as described herein.

The therapeutic cell or therapeutic vector may be administered by any suitable route of administration.

By way of example, a therapeutic cell or therapeutic vector may be administered by intravenous administration or by Ommaya reservoir catheterisation.

A DAT tracer may be administered by methods which are known in the art. For example, the tracer may be administered by oral (e.g. to be swallowed or inhaled as a gas) or by intravenous administration. Typically, when used for imaging in the CNS, the tracer will be administered intravenously.

Determining the presence of a therapeutic cell expressing the DAT may be performed using techniques and methods which are known in the art. Imaging techniques which are suitable for detecting a therapeutic cell expressing DAT in the CNS of a subject include, but are not limited to, single-photon emission computed tomography (SPECT) or positron emission tomography (PET).

By way of example, the DAT radiotracer [$^{123}$I]-FP-CIT may be detected using SPECT and the DAT radiotracer [$^{18}$F]-FP-CIT may be detected using PET.

Central Nervous System (CNS)

As used herein, CNS refers to the part of the nervous system consisting of the brain and spinal cord.

The CNS site may be in the brain of the subject. In one embodiment, the CNS site is not in the striatum of the brain.

Subject

The subject may be a human or animal subject. The subject may be a mammalian subject.

The subject may have or be at risk of a disease as described herein.

Time Period

The method of the present invention may be used to determine the longevity of a therapeutic cell at a site in the CNS.

Accordingly, the presence of therapeutic cells expressing DAT may be determined following administration of a therapeutic cell expressing DAT or a therapeutic vector encoding DAT to a subject.

The presence of therapeutic cells expressing DAT may be determined from 4 hours after the therapeutic vector or therapeutic cell has been administered to the subject. The presence of therapeutic cells expressing DAT may be determined from 4 hours to at least 120 days after the therapeutic vector or therapeutic cell has been administered to the subject.

The presence of therapeutic cells expressing DAT may be determined at least 72 hours, at least 96 hours or at least 120 hours after the therapeutic vector or therapeutic cell has been administered to the subject.

The presence of therapeutic cells expressing DAT may be determined at least 7, 10, 15, 20, 25, 50, 100, or 150 days after the therapeutic vector or therapeutic cells have been administered to the subject.

Chimeric Antigen Receptor (CAR)

An immune effector cell may express a chimeric antigen receptor (CAR) in addition to the DAT.

CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to cells (such a T cells) using, for example, retroviral or lentiviral vectors. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

Transmembrane Domain

The CAR may comprise a transmembrane domain which spans the membrane. It may comprise a hydrophobic alpha helix. The transmembrane domain may be derived from CD8, CD28 or human IgG.

The transmembrane domain may be derived from any type I transmembrane protein. The transmembrane domain may be a synthetic sequence predicted to form a hydrophobic helix.

The transmembrane domain may comprise the sequence shown as SEQ ID NO: 9.

```
(CD28 transmembrane domain)
                                  SEQ ID NO: 9
FWVLVVVGGVLACYSLLVTVAFIIFWV
```

Intracellular Signalling Domain (Endodomain)

The endodomain is the signal-transmission portion of a CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of a CAR may comprise the CD28 endodomain and OX40 and CD3-Zeta endodomain.

The transmembrane and intracellular T-cell signalling domain (endodomain) of the may comprise the sequence shown as SEQ ID NO: 10 to 14.

```
(CD28 endodomain)
                                  SEQ ID NO: 10
RSKRSRLLHSDYMNMTPRRPGPTRKHYQPYAPPRDFAAY (OX40 endodomain)
                                  SEQ ID NO: 11
RSRDQRLPPDAHKPPGGGSFRTPIQEEQADAHSTLAKI (CD3 zeta endodomain)
                                  SEQ ID NO: 12
RSRVKFSRSADAPAYQQGQNQLYNELNLGRREEYDVLDKRRGRDPEM

GGKPRRKNPQEGLYNELQKDKMAEAYSEIGMKGERRRGKGHDGLYQG

LSTATKDTYDALHMQALPPR (CD28Z)
                                  SEQ ID NO: 13
RSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKN
```

```
-continued
PQEGLYNELQKDKMAEAYSEIGMKGERRRGKGHDGLYQGLSTATKDT

YDALHMQALPPR (CD28OXZ)
                                         SEQ ID NO: 14
RSKRSRLLHSDYMNMTPRRPGPTRKHYQPYAPPRDFAAYRSRDQRLP

PDAHKPPGGGSFRTPIQEEQADAHSTLAKIRVKFSRSADAPAYQQGQ

NQLYNELNLGRREEYDVLDKRRGRDPEMGGKPRRKNPQEGLYNELQK

DKMAEAYSEIGMKGERRRGKGHDGLYQGLSTATKDTYDALHMQALPP

R
```

Spacer

The CAR may comprise a spacer sequence to connect the antigen-binding domain with the transmembrane domain and spatially separate the antigen-binding domain from the endodomain. A flexible spacer allows the antigen-binding domain to orient in different directions to enable antigen binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

```
(hinge-CH2CH3 of human IgG1)
                                         SEQ ID NO: 15
AEPKSPDKTHTCPPCPAPPVAGPSVFLFPPKPKDTLMIARTPEVTCV

VVDVSHEDPEVKFNWYVDGVEVHNAKTKPREEQYNSTYRVVSVLTVL

HQDWLNGKEYKCKVSNKALPAPIEKTISKAKGQPREPQVYTLPPSRD

ELTKNQVSLTCLVKGFYPSDIAVEWESNGQPENNYKTTPPVLDSDGS

FFLYSKLTVDKSRWQQGNVFSCSVMHEALHNHYTQKSLSLSPGKKD

SEQ ID NO: 16 (human CD8 stalk):
TTTPAPRPPTPAPTIASQPLSLRPEACRPAAGGAVHTRGLDFACDI

SEQ ID NO: 17 (human IgG1 hinge):
AEPKSPDKTHTCPPCPKDPK (IgG1 Hinge-Fc)
                                         SEQ ID NO: 18
AEPKSPDKTHTCPPCPAPELLGGPSVFLFPPKPKDTLMISRTPEVTC

VVVDVSHEDPEVKFNWYVDGVEVHNAKTKPREEQYNSTYRVVSVLTV

LHQDWLNGKEYKCKVSNKALPAPIEKTISKAKGQPREPQVYTLPPSR

DELTKNQVSLTCLVKGFYPSDIAVEWESNGQPENNYKTTPPVLDSDG

SFFLYSKLTVDKSRWQQGNVFSCSVMHEALHNHYTQKSLSLSPGKKD

PK (IgG1 Hinge-Fc modified to remove Fc receptor
recognition motifs)
                                         SEQ ID NO: 19
AEPKSPDKTHTCPPCPAPPVA*GPSVFLFPPKPKDTLMIARTPEVTC

VVVDVSHEDPEVKFNWYVDGVEVHNAKTKPREEQYNSTYRVVSVLTV

LHQDWLNGKEYKCKVSNKALPAPIEKTISKAKGQPREPQVYTLPPSR

DELTKNQVSLTCLVKGFYPSDIAVEWESNGQPENNYKTTPPVLDSDG

SFFLYSKLTVDKSRWQQGNVFSCSVMHEALHNHYTQKSLSLSPGKKD

PK
```

Modified residues are underlined; * denotes a deletion.

Nucleic Acid Sequence

Nucleic acid sequences which encode a DAT protein are described herein.

Examples of nucleic acid sequences encoding a DAT protein as described herein as shown as SEQ ID NO: 23 to 29.

Any nucleic acid sequence as described herein may be in the form of a nucleic acid construct. In other words, the nucleic acid sequence may be an artificially constructed segment of nucleic acid.

The nucleic acid sequence encoding a DAT and a CAR may have the following structure:

DAT'-coexpr-CAR' or CAR'-coexpr-DAT';

in which DAT' is a nucleic acid sequence encoding the DAT; CAR' is a nucleic acid sequence encoding the CAR; and coexpr is a nucleic acid sequence enabling the co-expression of both the DAT and the CAR.

In other words, the nucleic acid sequence may comprise a first nucleic acid sequence encoding a DAT and a second nucleic acid sequence encoding a CAR, in which the first and second nucleic acid sequences are separated by a third nucleic acid sequence enabling the co-expression of both the DAT and the CAR.

The structure of the nucleic acid may be such that either the DAT or the CAR encoding nucleic acid sequence is located at the 5' or 3' position of the coexpr nucleic acid sequence.

Co-Expression Site

The nucleic acid may produce a polypeptide which comprises a DAT and a CAR joined by a cleavage site. The cleavage site may be self-cleaving, such that when the polypeptide is produced, it is immediately cleaved into the DAT and the CAR without the need for any external cleavage activity.

Various self-cleaving sites are known, including the Foot-and-Mouth disease virus (FMDV) 2A peptide and similar sequence (Donnelly et al, Journal of General Virology (2001), 82, 1027-1041), for instance like the 2A-like sequence from Thosea asigna virus which has the sequence shown as SEQ ID NO: 20: RAEGRGSLLTCGDVEENPGP The co-expressing sequence may be an internal ribosome entry sequence (IRES). The co-expressing sequence may be an internal promoter Suicide Gene Since therapeutic cells engraft and are autonomous, a means of selectively deleting the cells in recipients is desirable. This is particularly the case for immune effector cells expressing a CAR.

Suicide genes are genetically encodable mechanisms which result in selective destruction of infused cells in the face of unacceptable toxicity. The earliest clinical experience with suicide genes is with the Herpes Virus Thymidine Kinase (HSV-TK) which renders cells susceptible to Ganciclovir. HSV-TK is a highly effective suicide gene. However, pre-formed immune responses may restrict its use to clinical settings of considerable immunosuppression such as haploidentical stem cell transplantation. Inducible Caspase 9 (iCasp9) is a suicide gene constructed by replacing the activating domain of Caspase 9 with a modified FKBP12.

iCasp9 is activated by an otherwise inert small molecular chemical inducer of dimerization (CID). iCasp9 has been recently tested in the setting of haploidentical HSCT and can abort GvHD. The biggest limitation of iCasp9 is dependence on availability of clinical grade proprietary CID. Both iCasp9 and HSV-TK are intracellular proteins, so when used as the sole transgene, they have been co-expressed with a marker gene to allow selection of transduced cells.

The therapeutic cell or therapeutic vector may comprise a suicide gene, for example an iCasp9 or RQR8 molecule.

An iCasp9 may comprise the sequence shown as SEQ ID NO: 21 or a variant thereof having at least 80, 90, 95 or 98% sequence identity.

```
                                              SEQ ID NO: 21
MLEGVQVETISPGDGRTFPKRGQTCVVHYTGMLEDGKKVDSSRDRNK

PFKFMLGKQEVIRGWEEGVAQMSVGQRAKLTISPDYAYGATGHPGII

PPHATLVFDVELLKLESGGGSGVDGFGDVGALESLRGNADLAYILSM

EPCGHCLIINNVNFCRESGLRTRTGSNIDCEKLRRRFSSLHFMVEVK

GDLTAKKMVLALLELAQQDHGALDCCVVVILSHGCQASHLQFPGAVY

GTDGCPVSVEKIVNIFNGTSCPSLGGKPKLFFIQACGGEQKDHGFEV

ASTSPEDESPGSNPEPDATPFQEGLRTFDQLDAISSLPTPSDIFVSY

STFPGFVSWRDPKSGSWYVETLDDIFEQWAHSEDLQSLLLRVANAVS

VKGIYKQMPGCFNFLRKKLFFKTSAS
```

A recently described marker/suicide gene is RQR8 which can be detected with the antibody QBEnd10 and expressing cells lysed with the therapeutic antibody Rituximab.

An RQR8 may comprise the sequence shown as SEQ ID NO: 22 or a variant thereof having at least 80, 90, 95 or 98% sequence identity.

```
                                              SEQ ID NO: 22
MGTSLLCWMALCLLGADHADACPYSNPSLCSGGGGSELPTQGTFSNV

STNVSPAKPTTTACPYSNPSLCSGGGGSPAPRPPTPAPTIASQPLSL

RPEACRPAAGGAVHTRGLDFACDIYIWAPLAGTCGVLLLSLVITLYC

NHRNRRRVCKCPRPVV
```

The marker/suicide gene may be expressed as a single polypeptide with a CAR or DAT as described herein, for example by using a self-cleaving peptide between the two sequences.

The marker/suicide gene may be expressed as a dipeptide with the DAT. By way of example, the DAT may comprise the sequence shown as SEQ ID NO: 7 (see FIG. 9).

The DAT protein described herein may have a sequence as shown in SEQ ID NO: 7 or a variant thereof having at least 80% sequence identity and retaining the ability to bind a DAT tracer which binds to the wild type DAT protein.

The variant may have at least 80, 85, 90, 95 or 99% sequence identity to SEQ ID NO: 7.

Vector

The present invention also provides a vector which comprises a nucleic acid sequence as described herein. Such a vector may be used to introduce the nucleic acid sequence into a cell so that it expresses and produces a DAT and/or CAR as described herein.

The present invention also provides a therapeutic vector comprising a nucleic acid sequence encoding a DAT comprising the sequence shown as SEQ ID NO: 1, 4, 5, 6, 7 or 8 or a variant thereof with at least 80% sequence identity and a therapeutic nucleic acid sequence.

The therapeutic nucleic acid sequence is not limited and may be, for example, a protein encoding nucleic acid sequence, a miRNA sequence or a long non-coding RNA.

The vector may, for example, be a plasmid or a viral vector, such as a retroviral vector or a lentiviral vector or an adenoviral vector.

The vector may be capable of transfecting or transducing a T cell. The vector may be capable of transfecting or transducing a cell of the CNS, such as a neuron or a glial cell.

The vector may also comprise a nucleic acid sequence encoding a suicide gene, such as iCasp9 or RQR8.

Method

DAT-expressing cells may be generated by introducing DNA or RNA coding for DAT by one of many means including transduction with a viral vector, transfection with DNA or RNA.

The present invention also provide a cell composition comprising DAT-expressing therapeutic cells, such as CAR-expressing immune effector cells, according to the present invention. The cell composition may be made by transducing a sample ex vivo with a nucleic acid construct or vector as described herein.

Alternatively, DAT-expressing cells may be derived from ex vivo differentiation of inducible progenitor cells or embryonic progenitor cells to the relevant cell type, such as T cells.

Alternatively, an immortalized cell line such as a T-cell line which retains its lytic function and could act as a therapeutic may be used.

A therapeutic cell of the invention may therefore be made by:
(i) isolation of a cell-containing sample from a subject or other sources described above; and
(ii) transduction or transfection of the cells with a nucleic acid or vector as described.

Immune effector cells of the present invention may either be created ex vivo either from a subject's own peripheral blood (1st party), or in the setting of a haematopoietic stem cell transplant from donor peripheral blood (2nd party), or peripheral blood from an unconnected donor (3rd party).

A DAT-expressing immune effector cell of the invention may be an ex vivo T cell from a subject. The T cell may be from a peripheral blood mononuclear cell (PBMC) sample. T cells may be activated and/or expanded prior to being transduced with a nucleic acid or vector as described herein, for example by treatment with an anti-CD3 monoclonal antibody.

An immune effector cell of the invention may be made by:
(i) isolation of an immune effector cell-containing sample from a subject or other sources described above; and
(ii) transduction or transfection of the cells with a nucleic acid or vector as described herein.

The therapeutic cells, for example the immune effector cells, may then be purified, for example, by selection on the basis of expression of DAT or the co-expression of DAT and a CAR.

Pharmaceutical Composition

The present invention also relates to a pharmaceutical composition containing a therapeutic cell or a therapeutic vector according to the present invention. The pharmaceutical composition comprises a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion or Ommaya reservoir catheterisation.

In one embodiment the pharmaceutical composition comprises an immune effector cell or a therapeutic stem cell.

Use

The present invention also relates to the use of a nucleic acid or a vector of the present invention for the preparation of a therapeutic cell. The present invention also provides a nucleic acid or a vector of the present invention for use in the preparation of a therapeutic cell.

The preparation of a therapeutic cell refers to the generation of a therapeutic cell which expresses DAT. By way of example, such a therapeutic cell may be generated by the methods as described herein.

The present invention further provides a pharmaceutical composition of the present invention for use in treating and/or preventing a disease. In a further aspect the present invention relates to the use of a therapeutic cell or a therapeutic vector of the present invention in the manufacture of a medicament for treating and/or preventing a disease.

The invention further provides a method of treating and/or preventing a disease which comprises the step of administering a pharmaceutical composition of the present invention to a subject in need thereof.

To "treat" means to administer the pharmaceutical composition to a subject having an existing disease in order to lessen, reduce or improve at least one symptom associated with the disease and/or to slow down, reduce or block the progression of the disease.

To "prevent" means to administer the pharmaceutical composition to a subject who has not yet contracted the disease and/or who is not showing any symptoms of the disease to prevent or impair the cause of the disease (e.g. infection) or to reduce or prevent development of at least one symptom associated with the disease.

The above methods and uses involve the administration of an effective amount of the pharmaceutical composition to the subject. An effective amount refers to an amount which is capable of, for example, lessening, reducing or improving at least one symptom associated with the disease and/or slowing down, reducing or blocking the progression of the disease.

The disease may be any disease of the CNS.

The disease may be a cancer of the CNS. For example the disease may be a tumour of the brain, meninges or spinal cord.

Such diseases include gliomas, lymphomas of the CNS and medulloblastomas.

Treatment of gliomas using, for example, an immune effector cell of the present invention, may involve targeting tumour-associated antigens such as epidermal growth factor receptor (EGFR), the variant 3 of EGFR (EGFRvIII), Vimentin, Tenascin, MRP3 or IL13Ralpha.

Treatment of lymphomas of the CNS using, for example, an immune effector cell of the present invention, may involve targeting tumour-associated antigens such as CD19, CD20 and CD22.

Treatment of medullobastomas using, for example, an immune effector cell of the present invention, may involve targeting tumour-associated antigens such as diasialoganglioside or HER2.

The disease may be stroke or a neurodegenerative disorder. Examples of neurodegenerative disorders include, but are not limited to, Amyotrophic lateral sclerosis (ALS), Parkinson's, Alzheimer's, and Huntington's.

The invention will now be further described by way of Examples, which are meant to serve to assist one of ordinary skill in the art in carrying out the invention and are not intended in any way to limit the scope of the invention.

EXAMPLES

Figure 1C:
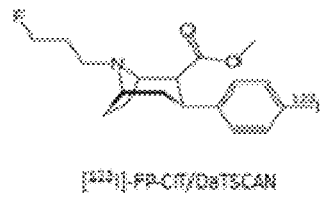
Figure 1B:
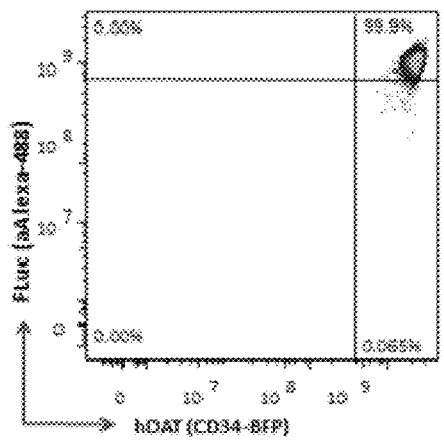

Example 1—Functional Expression and Binding of Dopamine Active Transporter (DAT) in T-Cells To determine the potential for utilising a human DAT (hDAT) reporter to image T-cells using $[^{123}I]$-FP-CIT, a retroviral vector (SFG.hDAT.I.CD34) encoding both hDAT and CD34 genes was constructed (FIG. 1a) and used to transduce SupT1 cell line. The SupT1 cell line is a CD4+ human T-cell line with tumorigenic properties and stable transduction has been previously demonstrated with no significant reduction in the expression of introduced genes[8]. Flow analysis of the SupT1/SFG.hDAT.I.CD34 cells indicated a transduction efficiency of 20-25% and cells were subsequently selected by CD34 expression to 99% purity using FACS (FIG. 1b).

Figure 1D:
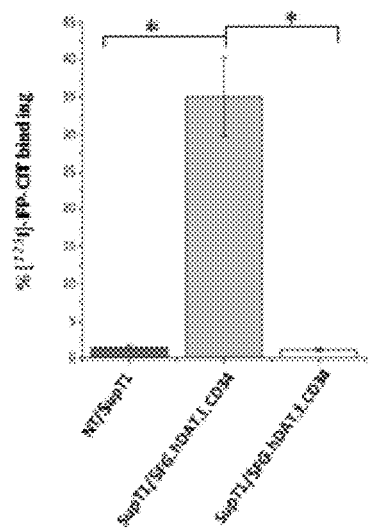
Figure 1E:
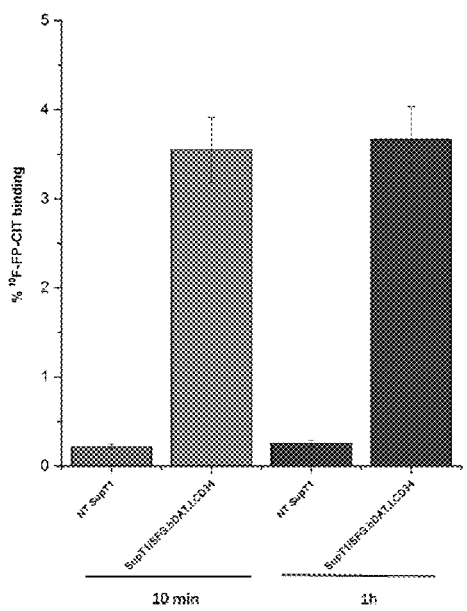

Binding of $[^{123}I]$-FP-CIT (FIG. 1c) to hDAT reporter cells was demonstrated by co-incubation of tracer with SupT1/SFG.hDAT.I.CD34 cells and compared against control non-transduced (NT) SupT1 cells. The percentage $[^{123}I]$-FP-CIT binding was 25 fold greater (FIG. 1d) in SupT1/SFG.hDAT.I.CD34 (35.10±5.24%) compared to control cells (1.41±0.40%). To demonstrate specific binding of $[^{123}I]$-FP-CIT, cells were co-incubated with 'cold' compound ([I]-FP-CIT). $[^{123}I]$-FP-CIT binding to SupT1/SFG.hDAT.I.CD34 cells was significantly (p<0.001) reduced by 32-fold (1.10±0.22%) in the presence of [I]-FP-CIT. There was no significant difference (p=1.00) in % $[^{123}I]$-FP-CIT binding between NT control cells and SupT1/SFG.hDAT.I.CD34 cells co-incubated with [I]-FP-CIT suggesting complete binding inhibition.

Example 2—T Cells Expressing hDAT Retain Proliferative and IFN-γ Release Ability Primary T cells, EBV-specific CTLs were engineered with hDAT to study any effect the reporter may have on the proliferation and cytokine release. EBV-CTLs were transduced with hDAT (EBV-CTL/SFG.hDAT.I.CD34) or a control vector encoding a HA1 T cell receptor (EBV-CTL/SFG.V5-HA1-TCRβ_opt.I.CD34) and the proliferative and IFN-γ release ability was compared to non-transduced EBV-CTLs (NT/EBV CTLs). The transduction efficiency was 39.4% in EBV-CTL/SFG.hDAT.I.CD34 (FIG. 2b), 49.0% in EBV-CTL/SFG.V5-HA1-TCRβ_opt.I.CD34 (FIG. 2c) in comparison to NT/EBV CTLs (FIG. 2a). There was no significant (p>0.05) difference in the functional capabilities between NT/EBV CTLs, EBV-CTL/SFG.hDAT.I.CD34 and EBV-CTL/SFG.V5-HA1-TCRβ_opt.I.CD34 cells upon stimulation with B-LCLs indicating EBV-CTL/SFG.hDAT.I.CD34 cells were able to retain their proliferative and IFN-γ release ability at levels comparable to control cells.

Example 3—In Vivo Evaluation of the hDAT/$[^{123}I]$-FP-CIT Reporter System

Figure 3A:
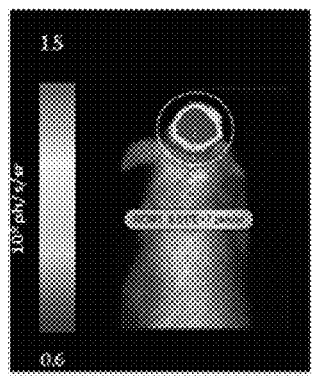
FIG. 3—Multimodality imaging of SupT1/SFG.hDAT-.I.CD34 cells—(FIG. 3a) Bioluminescence imaging confirming viability of SupT1/SFG.hDAT.I.CD34 cells co-transduced with FLuc at three weeks post intracranial injection.
(FIG. 3b) Representative small SPECT/CT, MR/CT and SPECT/MR/CT images demonstrated good correlation of the xenograft site (22.86±4.96 mm$^3$) and [$^{123}$I]-FP-CIT binding to SupT1/SFG.hDAT.I.CD34 in vivo. SPECT/CT images were acquired 2 h post intravenous injection of 16.76±1.45 MBq (250 ul) of [$^{123}$I]-FP-CIT. CT colour scheme has been adjusted in the co-registered image to clearly distinguish between the three modalities.
(FIG. 3c) Whole brain slices (2 μm) were stained with H&E.
(FIG. 3d/FIG. 3e) Magnified images (×20) demonstrated the presence of CD34-positive cells at the xenograft site.

Immunocompromised mice (n=4) were stereotactically injected with SupT1/SFG.hDAT.I.CD34 cells co-transduced with FLuc above the right basal ganglia. Sequential bioluminescence, MRI and SPECT images were acquired at day 25 post cell inoculation. Bioluminescence and MR images were acquired prior to [$^{123}$I]-FP-CIT imaging. Cell viability was confirmed using bioluminescence (FIG. 3a) and xenograft volumes (22.86±4.96 mm$^3$) were measured by manual drawing of ROIs on T$_2$-weighted MR images (FIG. 3b).

Figure 3B:
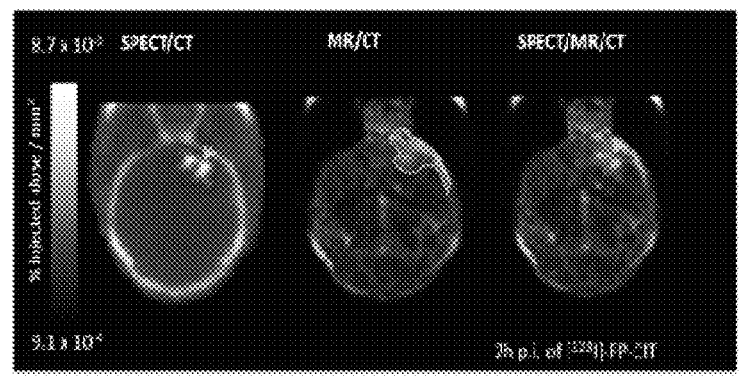
Figure 3C:
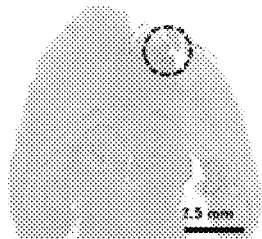
Figure 3D:
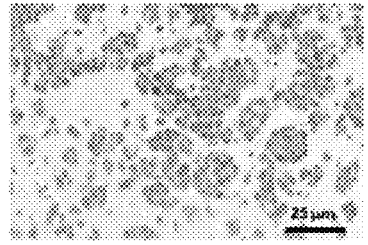
Figure 3E:
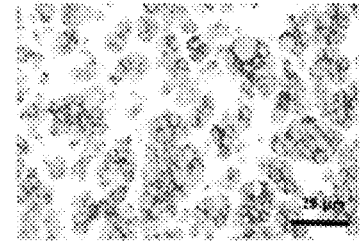
Figure 4A:
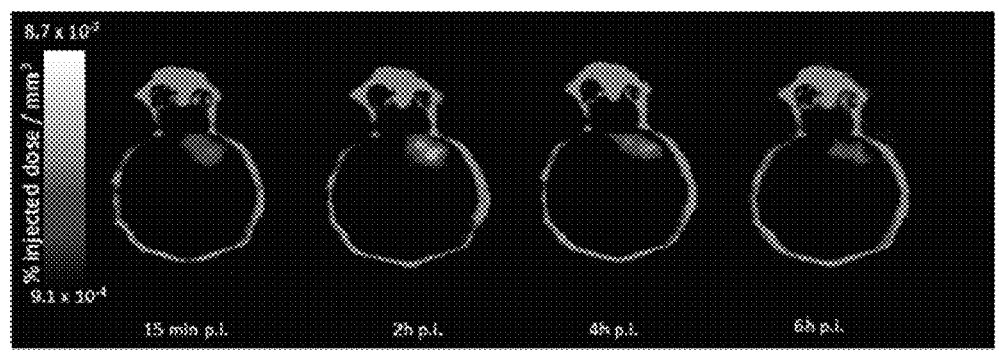
(FIG. 4a) Representative dynamic small animal SPECT/CT images acquired at 15 min, 2 h, 4 h and 6 h post injection. SPECT signal was detected as early as 15 min and up to 6 hr post radiotracer injection in hDAT-positive xenografts.

The co-registered SPECT-MR-CT images displayed good co-localisation of the MR contrast and SPECT signal at the site of injection (FIG. 3b). Dynamic brain SPECT images were acquired at 15 min, 2 h, 4 h and 6 h post radiotracer injection. hDAT-positive xenografts were visualised as early as 15 mins and up to 6 h post [$^{123}$I]-FP-CIT injection (FIG. 4a). A SPECT signal was non-detectable in control animals intracranially injected with non-transduced SupT1 cells.

Figure 4B:
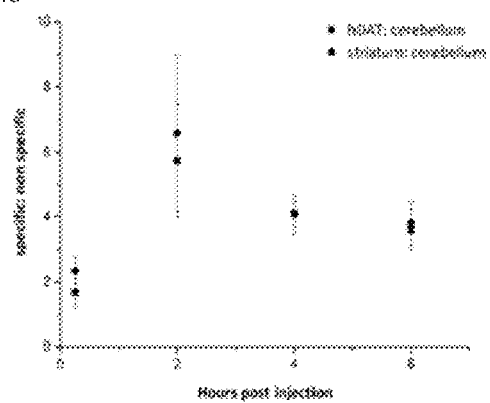
(FIG. 4b) Specific to non-specific biding ratios (hDAT-xenograft: cerebellum and striatum: cerebellum) were calculated using the mean counts extracted from the image guided ROIs. The optimum imaging window for SupT1/SFG.hDAT.I.CD34 cells was 2 h post [$^{123}$I]-FP-CIT injection.
Figure 5:
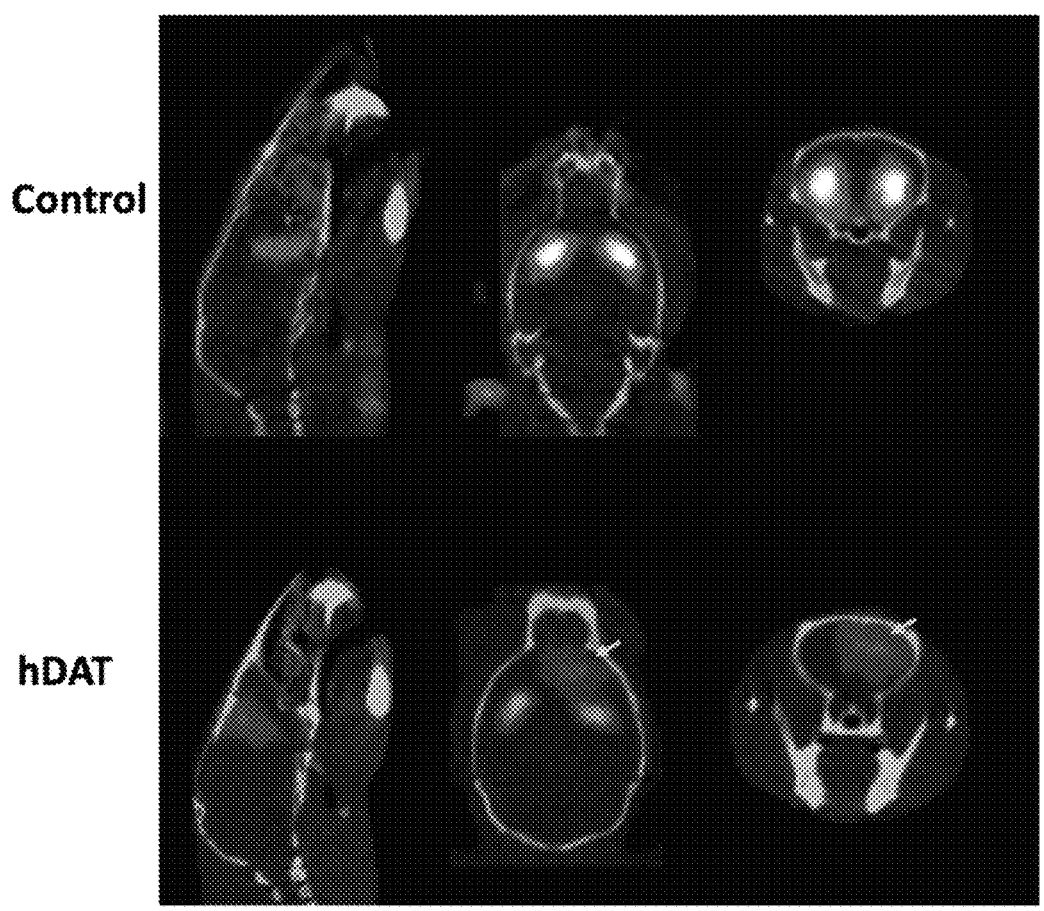
FIG. 5—PET/CT image acquisition and processing showing that hDAT positive cells could also be detected using $^{18}$F-FP-CIT i.v. and PET/CT image acquisition FIG. 6—Diagram of hDAT construct and hDAT variant proteins generated FIG. 7—Binding of $^{123}$I-FP-CIT by hDAT variants expressed from different constructs FIG. 8—Functional co-expression of a CD19 CAR and a DAT protein from the same construct—FIG. 8A) Diagram of the tricistronic construct.
Figure 6:
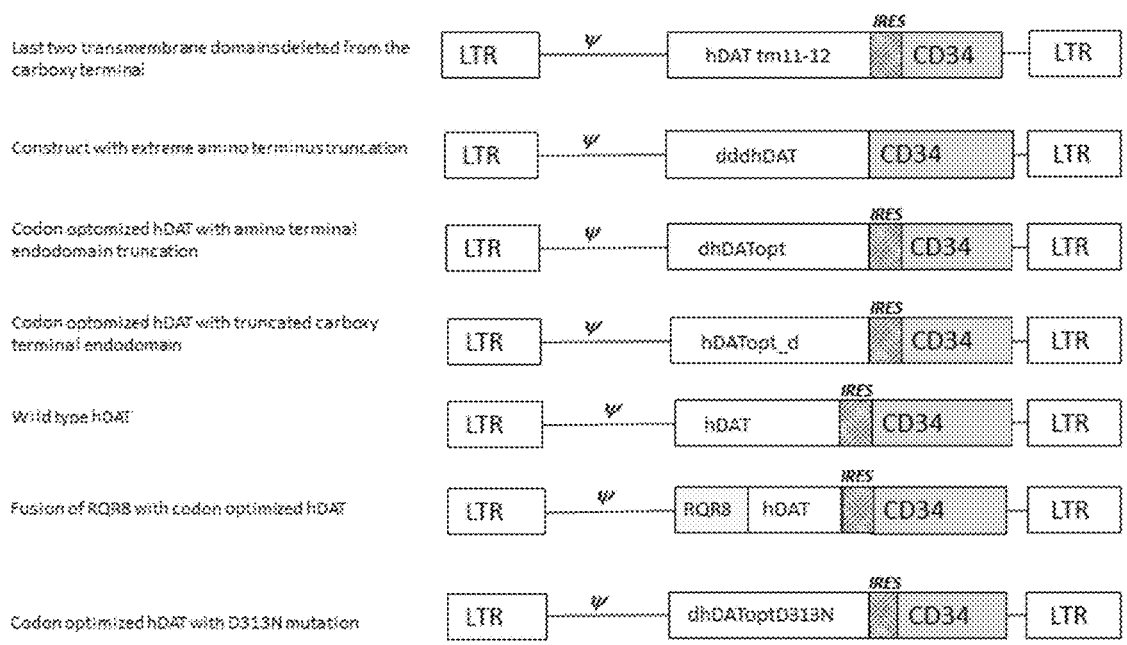

Image guided [$^{123}$I]-FP-CIT time-activity curves were generated by automatic segmentation of ROIs using an inviCRO mouse brain atlas for the striatum and cerebellum (FIG. 4b) and manually delineating ROIs on co-registered SPECT-MR-CT kinetic datasets for the xenograft. ROIs were drawn around three regions; the hDAT-positive xenograft, the striatum (region with high endogenous expression of DAT), and the cerebellum (non-specific binding). Over the course of 6 hours, the hDAT-positive xenograft and striatum had a similar activity profile whilst activity remained constant in the cerebellum after 2 h post injection (FIG. 4c). The specific (DAT) to non-specific (cerebellum) binding ratio were also similar in the hDAT-positive xenograft and striatum. The ratios gradually increased and peaked at 2 h (hDAT: cerebellum, 5.73±1.75) and striatum: cerebellum, 6.56±2.40) became constant after 4 h (hDAT: cerebellum, 4.09±0.38 and striatum: cerebellum, 4.08±0.60) indicating 2 h post injection as the optimum imaging time to visualise hDAT-positive xenografts which resulted in a better signal-to-background image. Histopathological analysis further resolved the xenograft at the site of injection (FIG. 4d) and confirmed the presence of SupT1/SFG.hDAT-.I.CD34 cells (FIGS. 4e and 4f) in the mouse brain.

hDAT positive cells could also be detected using $^{18}$F-FP-CIT i.v. and PET/CT image acquisition (see FIG. 5).

Example 4—Generation of Variant hDATs

The inventors generated a range of constructs expressing hDAT and hDAT variant proteins. Assessment of the binding capabilities of the hDAT and variant hDAT proteins demonstrated that a hDAT protein in which the last two transmembrane domains had been deleted was unable to bind [123I]-FP-CIT (FIG. 7).

Figure 7:
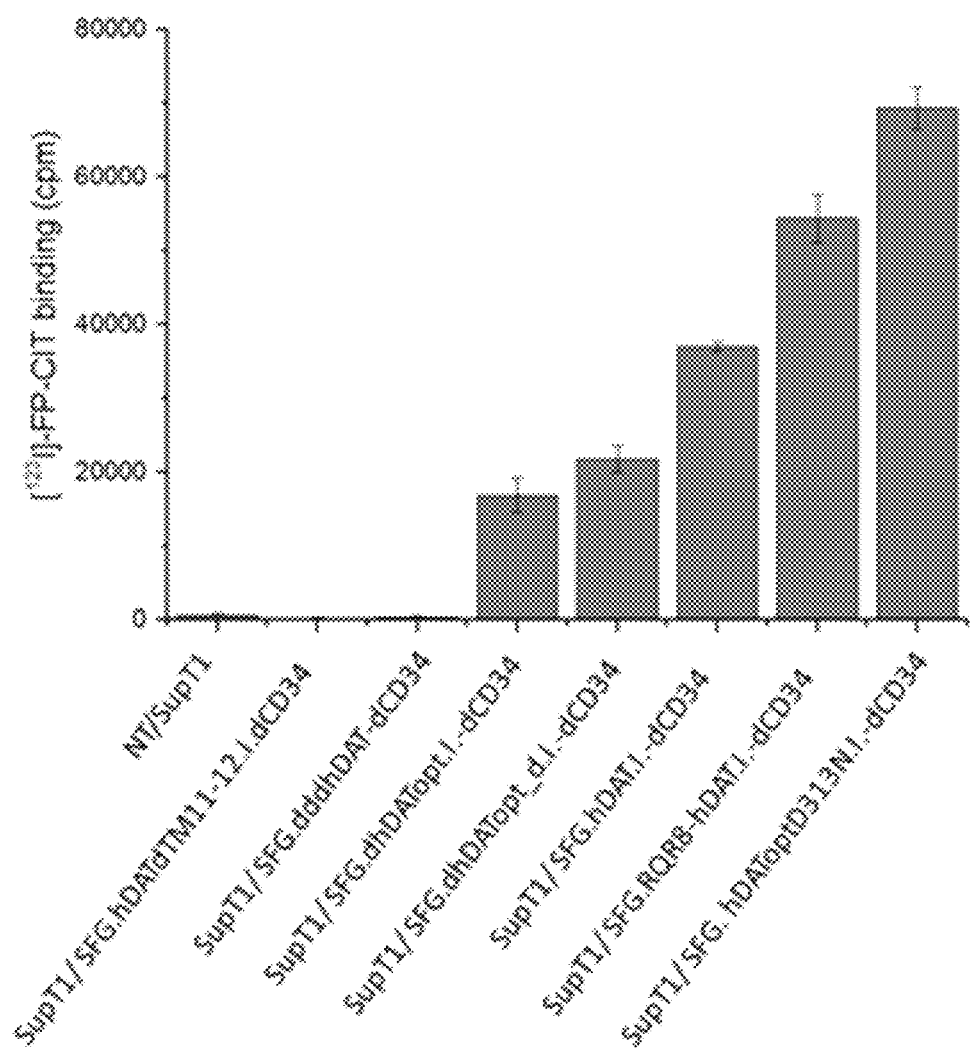

In contrast truncated hDAT proteins lacking either the 49 N-terminal amino acids or the 18 C-terminal amino acids compared to wild-type hDAT were able to bind [$^{123}$I]-FP-CIT (FIG. 7—dhDATopt and dhDATopt-d 1).

In addition hDAT tagged with RQR8 and hDAT including a D313N mutation were able to bind increased levels of [$^{123}$I]-FP-CIT compare to wild-type hDAT (FIG. 7—RQR8-hDAT and hDAToptD313N).

Example 5—Functional Co-Expression of a CD19 CAR-hDAT Construct

Figure 8A:
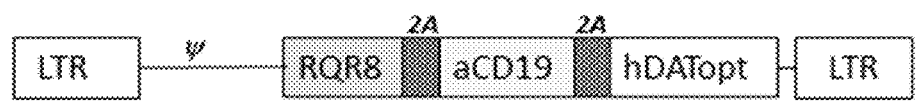
FIG. 8B) Functional binding of the CD19 CAR to CD19.
FIG. 8C) Functional binding of the DAT protein to $^{123}$I-FP-CIT FIG. 9—Variant DAT proteins FIG. 10—Homing of systemically administered T cells to the brain.

The inventors generated a construct which co-expressed a CD19 CAR and hDAT (see FIG. 8A).

Figure 8B:
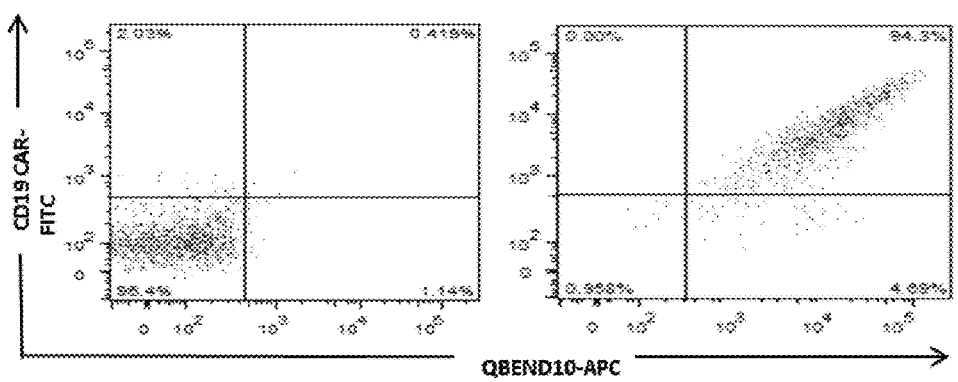
Figure 8C:
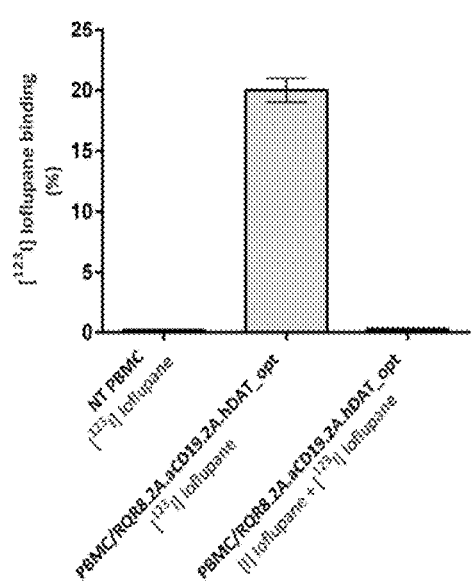

These analyses demonstrated that it was possible to provide functional co-expression of a CAR and a DAT protein from the same construct. In particular, the CD19 CAR expressed from the construct was able to able to bind to CD19 (see FIG. 8B) and hDAT expressed from the construct was able to bind [$^{123}$I]-FP-CIT (see. FIG. 8C)

Example 6—Bioluminescence Imaging Demonstrates that Systemically Administered T Cells Track to the Brain Homing of anti-CD19 CAR T cells to CNS lymphoma post systemic administration was demonstrated by bioluminescence imaging and histology (see FIG. 10).
Materials and Methods
Molecular Cloning Bene-synthesis using PCR assembly of overlapping oligos generated all constructs unless otherwise specified. Oligonucleotides obtained from IDTDNA, quick ligase, phusion polymerase and NEB5α (New England Biolabs) were used for molecular cloning. The splicing oncoretroviral SFG vector[1] and an ECMV IRES[2] sequence fused expression vector encoding the hDAT reporter gene and CD34 (SFG.hDAT.I.CD34) was used.

To generate the CD19/hDAT co-expression construct an in-house algorithm was used for codon optimization of hDAT. Cryptic splicing, hairpins, cis-acting sequences and literal repeats were eliminated with GC content was maintained at 70%. The tricistronic construct (RQR8.2A.aCD19.2A.hDAT_opt) consisted of a 2A peptide linkage of the RQR8 cell marker gene, anti-CD19 CAR fused with the codon optimised hDAT (huDATopt).
Generation of hDAT Expressing T-Lymphocyte Cell Lines All cell culture medium and supplements were obtained from Lonza BioWhittaker unless otherwise stated. RD114 pseudotyped supernatant generated from transfection of HEK-293T cells with the expression plasmids supplying Gagpol, RD114 envelope PeqPam-env and hDAT. SupT1 cells obtained from the American Type Culture Collection (ATCC) were transduced and cultured in RPMI media supplemented with 10% fetal bovine serum (FBS) and GlutaMAX (Gibco), 10 mM HEPES, 0.1 μM 2-mercaptoethanol. Cell lines were maintained at 37° C. in a humidified 5% CO$_2$ atmosphere. SupT1 cell lines were engineered with SFG.hDAT.I.CD34 (SupT1/hDAT.I.CD34). SupT1/hDAT.I.CD34 cells were cotransduced with red shifted codon optimized Firefly Luciferase (FLuc; SFG.FLuc_tisix5_2A_Gluc_exo_mycx5) for bioluminescence (BLI) imaging.
hDAT Expressing EBV Specific CTLs PBMCs isolated from three donors were stimulated as previously described[3] with EBV pepmix at 1 μg/mL in X-Vivo15+2% human AB serum. EBV-CTL cell were transduced with the hDAT vector (EBV-CTL/hDAT.I.CD34) or the control vector (EBV-CTL/V5-HA1-TCRβ_opt.I.CD34). Cell lines were expanded in culture for two weeks and stimulated with autologous, irradiated B-LCLs for 4 days. Proliferation was tested by H$^3$-thymidine uptake for 21 h and IFN-γ secretion was assessed by ELISA 24 h after stimulation.
Flow Cytometry and Cell Sorting The hDAT vector expression was determined by αCD34-eBFP staining for the SupT1/hDAT.I.CD34 cells and αCD34-APC staining for transduced EBV-CTLs. The brightest 5% of SupT1/hDAT.I.CD34 cells were isolated by fluorescence activated cell sorting (FACs). Beckman-Coulter Cyan BD LSRII Fortessa instrument was used for flow cytometry and the Beckman-Coulter MoFlo-XDP sorter for flow sorting.

To determine functional CD19 binding by the CD19 CAR co-expressed with hDAT, transduction efficiency was determined by QBEND10 staining for the PBMC's/RQR8.2A.aCD19.2A.hDAT_opt cells and aCD19 CAR expression in PBMC's/RQR8.2A.aCD19.2A.hDAT_opt cells was assessed using a method previously described[9] with the following modifications; A K562 cell line which secretes a truncated version of CD19[10] fused to the rabbit Ig constant domain was generated. Target cells were stained using a crude cellular supernatant (CD19-rFc) followed by an anti-rabbit Fc antibody (FITC) to confirm the presence of the CAR mediated binding. Fluoresence activated cell sorting was used to isolate the brightest 5% of SupT1/hDAT.I.CD34 cells. Beckman-Coulter Cyan BD LSRII Fortessa instrument was used for flow cytometry and the Beckman-Coulter MoFlo-XDP sorter for flow sorting.

In Vitro Radiosubstrate Binding Assays

Reporter protein binding capabilities was assessed in a method previously described. Briefly, $1 \times 10^6$ all hDAT expressing T-cells and the non-transduced control cells were incubated at 37° C. with 7.4 kBq $^{123}$I-FP-CIT (GE, Healthcare) for 30 mins. At each time point, cells were rapidly washed twice with 500 μL ice-cold PBS and the supernatant collected. Cell pellets were re-suspended in 1 mL PBS. $^{123}$I-FP-CIT binding in cells and medium was measured using a gamma counter (WIZARD$^2$, PerkinElmer, UK). To determine the non-specific binding of the $^{123}$I-FP-CIT in hDAT (+) cells, transduced cells and non-transduced cells were incubated with 50 μM of β-CIT-FP (ABX) for 5 min. $^{123}$I-FP-CIT cells were subsequently prepared for gamma counting as mentioned above. All experiments were performed in triplicates and repeated ≥twice. All results are given as mean±standard deviation of the mean (SD). The data was analysed using one way analysis of variance (ANOVA) followed by the Tukey's HSD test with the IBM SPSS software.

Mouse Brain Xenograft Models

All animal procedures were carried out in accordance with the UK Animals (Scientific Procedures) 1986 Act and institutional ethics regulation. NSG mice were bred in-house and kept according to institutional guidelines. Male mice 6-10 weeks old were injected with 2 mg/kg body weight of 5% carprofen (Norbrook) and anaesthetised with 3-5% Isoflurane (ABBOTT, UK) in an induction chamber. Animals were placed in a stereotactic frame (David Kopf Instruments) with an anaesthesia head holder to deliver 3% isoflurane. A sagittal incision over the parieto-occipital bone using a sterile scalpel (Swann Morton Ltd) was made and a blunt ended Hamilton (75N, 26s/2"/2'5 ul) syringe with SupT1/hDAT.I.CD34 was placed 1.5 mm lateral and 1 mm anterior of bregma. The needle was lowered 4 mm in the brain through a burr hole and retracted 1 mm to create a small reservoir where the cells ($1 \times 10^4$ in a 3 μl volume) were injected.

In Vivo Bioluminescence and MR Imaging

Bioluminescence imaging was performed every 7 days following inoculation. Images were acquired 15 min. post intraperitoneal (i.p.) administration of 200 μL of D-Luciferin (10 mg/mL) and 1 min acquisition time. Images were acquired using a Biospace photon imager Optima system and analysed using the Biospace M3 Vision software.

Magnetic resonance images were acquired on the same day as the SPECT/CT images for accurate coregistration of the MRI and SPECT data[5]. Images were acquired on a small animal 1T ICON MRI (Bruker, Rimpar, Germany) scanner with a 26 mm diameter mouse head coil. Images were acquired using a $T_2$—weighted sequence (TR=3201.5 ms, TE=85 ms, flip angle=90°, 20×20 mm$^2$ field of view=2 cm, 96×96 matrix, slice thickness=0.5 mm, 30 averages were acquired with an acquisition time of 13 min). Mice bearing SupT1/hDAT.I.CD34 cells were imaged at three weeks post cell inoculation.

SPECT/CT Image Acquisition and Processing

Animals were administered with 1.5 mmol/kg of the thyroid blocking agent potassium perchlorate (Sigma Aldrich, USA) intraperitoneally one hour prior to imaging. Animals were imaged with a NanoSPECT/CT small animal in vivo scanner (Mediso, Hungary) consisting of a rotating double headed camera (company, country). 1.2 mm pinhole mouse apertures were used. Imaging was performed under isoflurane (1.5-2%) and the body temperature was maintained at 37° C. using a heated animal bed (Minerve, France). For the kinetic study, animals were administered with an average of 17.25±1.22 MBq of $^{123}$I-FP-CIT i.v. and 15 min. brain scans were acquired day 25 post tumour inoculation at 15 min. 2 h, 4 h, 6 h and 8 h. Images were reconstructed using HiSPECT software (InviCRO, USA) and image processing analysis was performed (VivoQuant Software; InviCRO, USA).

Kinetic Study Data Analysis

Time activity profiles were generated evaluate the hDAT reporter system in vivo. Regions of interest (ROIs) for the hDAT expressing xenografts, cerebellum (chose background region) and striatum were drawn on the SPECT/MR/CT coregistered data. The percentage in injected dose per mm$^3$ (% ID/mm$^3$) was calculated by; injected dose (MBq)/counts in the whole body (MBq)/volume of the ROI (mm$^3$) to determine the peak uptake time and the optimum imaging window. A method based on the striatal binding ratio was utilised to determine specific-to-nondisplaceable binding ratios previously described as indicative of the binding potential at the time of binding equilibrium[6,7]. The binding ratios were calculated by determining the mean counts per pixel in the specific region (hDAT expressing xenograft for the hDAT: cerebellum and hDAT: striatum ratios) divided by the mean counts per pixel in the nonspecific region.

Histopathology

Brain slices were stained with hematoxylin and eosin (H&E) and immunohistochemistry against CD34 was performed on alternate slices. Paraffin-embedded 2 μm brain slices were dewaxed and rehydrated. Endogenous $H_2O_2$ blocking was performed with a protease-blocking reagent (DakoCytomation, Denmark). Slides were incubated at room temperature for 30 min. with the following anti-human mouse monoclonal antibodies: CD34 (Leica Microsystems, UK) for the T-cells. Images were obtained using a Nano-Zoomer Digital Pathology System (Hamamatsu, Japan).

PET/CT Image Acquisition and Processing

Animals were administered with 1.5 mmol/kg of the thyroid blocking agent potassium perchlorate (Sigma Aldrich, USA) intraperitoneally one hour prior to imaging. Animals were imaged with a PET/CT small animal in vivo scanner (Mediso, Hungary). Imaging was performed under isoflurane (1.5-2%) and the body temperature was maintained at 37° C. using a heated animal bed (Minerve, France). Four weeks post tumour inoculation, animals were administered with 5 MBq of $^{18}$F-FP-CIT i.v. and brain scans were acquired 30 min post injection. A high-resolution CT was acquired immediately following SPECT imaging. Images were reconstructed using HiSPECT software (Invi-CRO, USA) and image processing analysis was performed (VivoQuant Software; InviCRO, USA).

In Vivo Bioluminescence Imaging

Bioluminescence imaging was performed every 7 days following inoculation. Images were acquired 15 min. post intraperitoneal (i.p.) administration of 200 μL of D-Luciferin (10 mg/mL) and 1 min acquisition time. Images were acquired using a Biospace photon imager Optima system and analysed using the Biospace M3 Vision software. Animals underwent further MRI, SPECT/CT imaging depending on the photon counts.

In Vivo MRI

Magnetic resonance images were acquired on the same day as the SPECT/CT images for accurate coregistration of the MRI and SPECT data. Images were acquired on a small animal 1T ICON MRI (Bruker, Rimpar, Germany) scanner with a 26 mm diameter mouse head coil. Images were acquired using a $T_2$—weighted sequence (TR=3201.5 ms, TE=85 ms, flip angle=90°, 20×20 mm² field of view=2 cm, 96×96 matrix, slice thickness=0.5 mm, 30 averages were acquired with an acquisition time of 13 min). For the CAR-T cells trafficking study, animals bearing Raji tumours were imaged at pre CAR T cell injection (day 11 post Raji tumour) to determine the tumour size prior to anti and day 7 post intravenous administration of 1×10⁷ aCD19 CAR T cells.

CNS Lymphoma Model

Figure 10A:
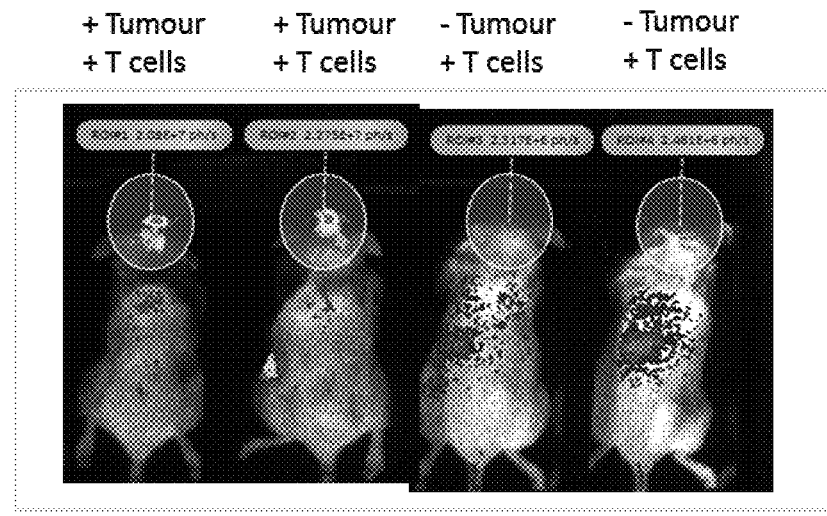
FIG. 10a, day 2 post administration of CAR T cells.
Figure 10B:
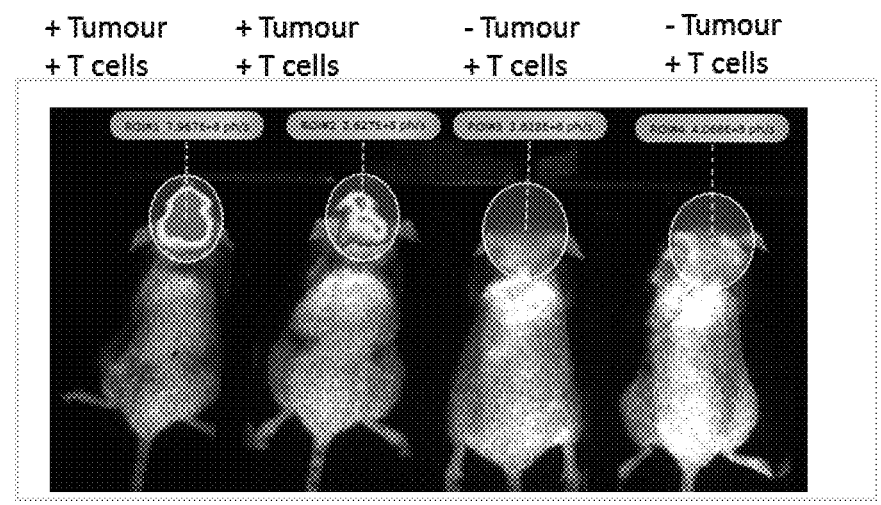
FIG. 10b, day 4 post administration of CAR T cells.
Figure 10C:
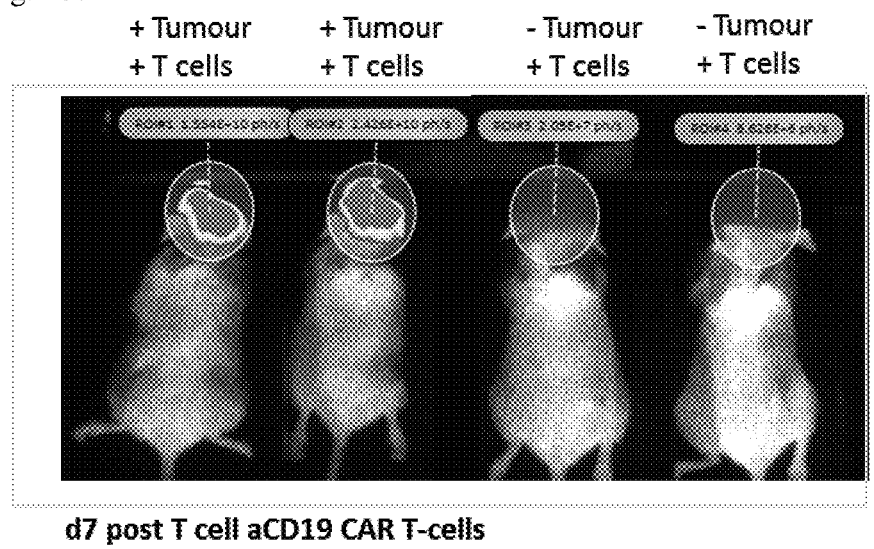
FIG. 10c, day 7 post administration of CAR T cells.

PBMCs co-transduced with anti-CD19 CAR and FLuc were injected via tail vein at two weeks post intracranial injection of lymphoma. Tumour progression was assessed by MRI and T cell distribution visualised by bioluminescence imaging (FIGS. 10A-10C).

REFERENCES

1. Riviere I, Brose K, Mulligan R C. Effects of retroviral vector design on expression of human adenosine deaminase in murine bone marrow transplant recipients engrafted with genetically modified cells. Proc Natl Acad Sci USA 1995; 92:6733-7.
2. Bochkov Y A, Palmenberg A C. Translational efficiency of EMCV IRES in bicistronic vectors is dependent upon IRES sequence and gene location. Biotechniques 2006; 41:283-+.
3. Moosmann A, Bigalke I, Tischer J, et al. Effective and long-term control of EBV PTLD after transfer of peptide-selected T cells. Blood 2010; 115:2960-70.
4. Badar A, Kiru L, Kalber T L, et al. Fluorescence-guided development of a tricistronic vector encoding bimodal optical and nuclear genetic reporters for in vivo cellular imaging. EJNMMI Res 2015; 5:18.
5. Andringa G, Drukarch B, Bol J G, et al. Pinhole SPECT imaging of dopamine transporters correlates with dopamine transporter immunohistochemical analysis in the MPTP mouse model of Parkinson's disease. NeuroImage 2005; 26:1150-8.
6. Laruelle M, Wallace E, Seibyl J P, et al. Graphical, kinetic, and equilibrium analyses of in vivo [123I] beta-CIT binding to dopamine transporters in healthy human subjects. Journal of cerebral blood flow and metabolism: official journal of the International Society of Cerebral Blood Flow and Metabolism 1994; 14:982-94.
7. van Dyck C H, Seibyl J P, Malison R T, et al. Age-related decline in striatal dopamine transporter binding with iodine-123-beta-CITSPECT. J Nucl Med 1995; 36:1175-81.
8. Hiasa A, Hirayama M, Nishikawa H, et al. Long-term phenotypic, functional and genetic stability of cancer-specific T-cell receptor (TCR) alphabeta genes transduced to CD8+ T cells. Gene Ther 2008; 15:695-9.
9. Philip B, Kokalaki E, Mekkaoui L, et al. A highly compact epitope-based marker/suicide gene for easier and safer T-cell therapy. Blood 2014; 124:1277-87.
10. Bradbury L E, Goldmacher V S, Tedder T F. The CD19 signal transduction complex of B lymphocytes. Deletion of the CD19 cytoplasmic domain alters signal transduction but not complex formation with TAPA-1 and Leu 13. J Immunol 1993; 151:2915-27.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A method of detecting a therapeutic cell expressing a dopamine transporter (DAT) at a central nervous system (CNS) site in a subject comprising the therapeutic cell, which method comprises the administration of a DAT tracer to the subject, wherein the presence of a therapeutic cell which expresses the DAT is determined by binding of the DAT tracer to the DAT on the therapeutic cell, and wherein the therapeutic cell is an immune effector cell engineered to express a DAT protein prior to administration of said cell to the subject.

2. The method according to claim 1 which comprises the steps of;
    i) administering the therapeutic cell engineered to express a DAT protein to the subject;
    ii) administering a DAT tracer to the subject; and
    iii) determining the presence of the therapeutic cell expressing the DAT at a site in the CNS of the subject by single-photon emission computed tomography (SPECT) or positron emission tomography (PET).

3. The method according to claim 1 wherein the DAT tracer is [$^{123}$I]-FP-CIT (Ioflupane; [I-123] N-ω-fluoropropyl-2β-carbomethoxy-3β-(4-iodophenyl) nortropane) or [$^{18}$F]-FP-CIT ([$^{18}$F] fluoropropyl-carbomethoxy-iodophenyl-nortropane).

4. The method according to claim 1 wherein the DAT comprises the sequence shown as SEQ ID NO: 1, 4, 5, 6, 7 or 8 or a variant thereof with at least 80% sequence identity.

5. The method according to claim 1 wherein the CNS site is in the brain of the subject.

6. The method according to claim 1 wherein the immune effector cell expresses a chimeric antigen receptor (CAR).

* * * * *

SEQUENCE LISTING

```
<160> NUMBER OF SEQ ID NOS: 29

<210> SEQ ID NO 1
<211> LENGTH: 620
<212> TYPE: PRT
<213> ORGANISM: Homo sapiens

<400> SEQUENCE: 1

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95
```

```
Ala Phe Leu Val Pro Tyr Leu Phe Met Val Ile Ala Gly Met Pro
            100                 105                 110
Leu Phe Tyr Met Glu Leu Ala Leu Gly Gln Phe Asn Arg Glu Gly Ala
            115                 120                 125
Ala Gly Val Trp Lys Ile Cys Pro Ile Leu Lys Gly Val Gly Phe Thr
        130                 135                 140
Val Ile Leu Ile Ser Leu Tyr Val Gly Phe Phe Tyr Asn Val Ile Ile
145                 150                 155                 160
Ala Trp Ala Leu His Tyr Leu Phe Ser Ser Phe Thr Thr Glu Leu Pro
                165                 170                 175
Trp Ile His Cys Asn Asn Ser Trp Asn Ser Pro Asn Cys Ser Asp Ala
                180                 185                 190
His Pro Gly Asp Ser Ser Gly Asp Ser Ser Gly Leu Asn Asp Thr Phe
            195                 200                 205
Gly Thr Thr Pro Ala Ala Glu Tyr Phe Glu Arg Gly Val Leu His Leu
        210                 215                 220
His Gln Ser His Gly Ile Asp Asp Leu Gly Pro Pro Arg Trp Gln Leu
225                 230                 235                 240
Thr Ala Cys Leu Val Leu Val Ile Val Leu Leu Tyr Phe Ser Leu Trp
                245                 250                 255
Lys Gly Val Lys Thr Ser Gly Lys Val Val Trp Ile Thr Ala Thr Met
                260                 265                 270
Pro Tyr Val Val Leu Thr Ala Leu Leu Leu Arg Gly Val Thr Leu Pro
            275                 280                 285
Gly Ala Ile Asp Gly Ile Arg Ala Tyr Leu Ser Val Asp Phe Tyr Arg
        290                 295                 300
Leu Cys Glu Ala Ser Val Trp Ile Asp Ala Ala Thr Gln Val Cys Phe
305                 310                 315                 320
Ser Leu Gly Val Gly Phe Gly Val Leu Ile Ala Phe Ser Ser Tyr Asn
                325                 330                 335
Lys Phe Thr Asn Asn Cys Tyr Arg Asp Ala Ile Val Thr Thr Ser Ile
                340                 345                 350
Asn Ser Leu Thr Ser Phe Ser Ser Gly Phe Val Val Phe Ser Phe Leu
            355                 360                 365
Gly Tyr Met Ala Gln Lys His Ser Val Pro Ile Gly Asp Val Ala Lys
        370                 375                 380
Asp Gly Pro Gly Leu Ile Phe Ile Ile Tyr Pro Glu Ala Ile Ala Thr
385                 390                 395                 400
Leu Pro Leu Ser Ser Ala Trp Ala Val Val Phe Phe Ile Met Leu Leu
                405                 410                 415
Thr Leu Gly Ile Asp Ser Ala Met Gly Gly Met Glu Ser Val Ile Thr
                420                 425                 430
Gly Leu Ile Asp Glu Phe Gln Leu Leu His Arg His Arg Glu Leu Phe
            435                 440                 445
Thr Leu Phe Ile Val Leu Ala Thr Phe Leu Leu Ser Leu Phe Cys Val
        450                 455                 460
Thr Asn Gly Gly Ile Tyr Val Phe Thr Leu Leu Asp His Phe Ala Ala
465                 470                 475                 480
Gly Thr Ser Ile Leu Phe Gly Val Leu Ile Glu Ala Ile Gly Val Ala
                485                 490                 495
Trp Phe Tyr Gly Val Gly Gln Phe Ser Asp Asp Ile Gln Gln Met Thr
            500                 505                 510
```

```
Gly Gln Arg Pro Ser Leu Tyr Trp Arg Leu Cys Trp Lys Leu Val Ser
            515                 520                 525

Pro Cys Phe Leu Leu Phe Val Val Val Ser Ile Val Thr Phe Arg
        530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
            595                 600                 605

Val Arg Gln Phe Thr Leu Arg His Trp Leu Lys Val
    610                 615                 620
```

<210> SEQ ID NO 2
<211> LENGTH: 519
<212> TYPE: PRT
<213> ORGANISM: Artificial Sequence
<220> FEATURE:
<223> OTHER INFORMATION: hDAT tm11-12 protein sequence

<400> SEQUENCE: 2

```
Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
        115                 120                 125

Ala Gly Val Trp Lys Ile Cys Pro Ile Leu Lys Gly Val Gly Phe Thr
130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
            180                 185                 190

His Pro Gly Asp Ser Ser Gly Asp Ser Ser Gly Leu Asn Asp Thr Phe
        195                 200                 205

Gly Thr Thr Pro Ala Ala Glu Tyr Phe Glu Arg Gly Val Leu His Leu
210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255
```

```
Lys Gly Val Lys Thr Ser Gly Lys Val Val Trp Ile Thr Ala Thr Met
                260                 265                 270

Pro Tyr Val Val Leu Thr Ala Leu Leu Arg Gly Val Thr Leu Pro
            275                 280                 285

Gly Ala Ile Asp Gly Ile Arg Ala Tyr Leu Ser Val Asp Phe Tyr Arg
            290                 295                 300

Leu Cys Glu Ala Ser Val Trp Ile Asp Ala Thr Gln Val Cys Phe
305                 310                 315                 320

Ser Leu Gly Val Gly Phe Gly Val Leu Ile Ala Phe Ser Tyr Asn
                325                 330                 335

Lys Phe Thr Asn Asn Cys Tyr Arg Asp Ala Ile Val Thr Thr Ser Ile
            340                 345                 350

Asn Ser Leu Thr Ser Phe Ser Ser Gly Phe Val Val Phe Ser Phe Leu
            355                 360                 365

Gly Tyr Met Ala Gln Lys His Ser Val Pro Ile Gly Asp Val Ala Lys
            370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
            420                 425                 430

Gly Leu Ile Asp Glu Phe Gln Leu Leu His Arg His Arg Glu Leu Phe
            435                 440                 445

Thr Leu Phe Ile Val Leu Ala Thr Phe Leu Leu Ser Leu Phe Cys Val
    450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
            485                 490                 495

Trp Phe Tyr Gly Val Gly Gln Phe Ser Asp Asp Ile Gln Gln Met Thr
            500                 505                 510

Gly Gln Arg Pro Ser Leu Tyr
            515
```

<210> SEQ ID NO 3
<211> LENGTH: 396
<212> TYPE: PRT
<213> ORGANISM: Artificial Sequence
<220> FEATURE:
<223> OTHER INFORMATION: dddhDAT protein sequence

<400> SEQUENCE: 3

```
Met Arg Gln Ser Pro Val Glu Ala Gln Asp Arg Glu Thr Trp Gly Lys
1               5                   10                  15

Lys Ile Asp Phe Leu Leu Ser Val Ile Gly Phe Ala Val Asp Leu Ala
            20                  25                  30

Asn Val Trp Arg Phe Pro Tyr Leu Cys Tyr Lys Asn Gly Gly Gly Ala
            35                  40                  45

Phe Leu Val Pro Tyr Leu Leu Phe Met Val Ile Ala Gly Met Leu Val
        50                  55                  60

Arg Arg Gly Ala Arg Ala Gly Pro Arg Met Pro Arg Gly Trp Thr Ala
65                  70                  75                  80

Leu Cys Leu Leu Ser Leu Pro Ser Gly Phe Met Ser Leu Asp Asn
                85                  90                  95
```

-continued

Asn Gly Thr Ala Thr Pro Glu Leu Pro Thr Gln Gly Thr Phe Ser Asn
                100                 105                 110

Val Ser Thr Asn Val Ser Tyr Gln Thr Thr Thr Pro Ser Thr Leu
        115                 120                 125

Gly Ser Thr Ser Leu His Pro Val Ser Gln His Gly Asn Glu Ala Thr
        130                 135                 140

Thr Asn Ile Thr Glu Thr Thr Val Lys Phe Thr Ser Thr Ser Val Ile
145                 150                 155                 160

Thr Ser Val Tyr Gly Asn Thr Asn Ser Ser Val Gln Ser Gln Thr Ser
                165                 170                 175

Val Ile Ser Thr Val Phe Thr Thr Pro Ala Asn Val Ser Thr Pro Glu
        180                 185                 190

Thr Thr Leu Lys Pro Ser Leu Ser Pro Gly Asn Val Ser Asp Leu Ser
        195                 200                 205

Thr Thr Ser Thr Ser Leu Ala Thr Ser Pro Thr Lys Pro Tyr Thr Ser
210                 215                 220

Ser Ser Pro Ile Leu Ser Asp Ile Lys Ala Glu Ile Lys Cys Ser Gly
225                 230                 235                 240

Ile Arg Glu Val Lys Leu Thr Gln Gly Ile Cys Leu Glu Gln Asn Lys
                245                 250                 255

Thr Ser Ser Cys Ala Glu Phe Lys Lys Asp Arg Gly Glu Gly Leu Ala
        260                 265                 270

Arg Val Leu Cys Gly Glu Glu Gln Ala Asp Ala Asp Gly Ala Gln
        275                 280                 285

Val Cys Ser Leu Leu Leu Ala Gln Ser Glu Val Arg Pro Gln Cys Leu
        290                 295                 300

Leu Leu Val Leu Ala Asn Arg Thr Glu Ile Ser Ser Lys Leu Gln Leu
305                 310                 315                 320

Met Lys Lys His Gln Ser Asp Leu Lys Lys Leu Gly Ile Leu Asp Phe
                325                 330                 335

Thr Glu Gln Asp Val Ala Ser His Gln Ser Tyr Ser Lys Thr Leu
        340                 345                 350

Ile Ala Leu Val Thr Ser Gly Ala Leu Leu Ala Val Leu Gly Ile Thr
        355                 360                 365

Gly Tyr Phe Leu Met Asn Arg Arg Ser Trp Ser Pro Thr Gly Glu Arg
        370                 375                 380

Leu Gly Glu Asp Pro Tyr Tyr Thr Glu Asn Gly Gly
385                 390                 395

<210> SEQ ID NO 4
<211> LENGTH: 571
<212> TYPE: PRT
<213> ORGANISM: Artificial Sequence
<220> FEATURE:
<223> OTHER INFORMATION: dhDAT protein sequence

<400> SEQUENCE: 4

Met Arg Gln Ser Pro Val Glu Ala Gln Asp Arg Glu Thr Trp Gly Lys
1               5                   10                  15

Lys Ile Asp Phe Leu Leu Ser Val Ile Gly Phe Ala Val Asp Leu Ala
                20                  25                  30

Asn Val Trp Arg Phe Pro Tyr Leu Cys Tyr Lys Asn Gly Gly Gly Ala
        35                  40                  45

Phe Leu Val Pro Tyr Leu Leu Phe Met Val Ile Ala Gly Met Pro Leu
    50                  55                  60

```
Phe Tyr Met Glu Leu Ala Leu Gly Gln Phe Asn Arg Glu Gly Ala Ala
 65                  70                  75                  80

Gly Val Trp Lys Ile Cys Pro Ile Leu Lys Gly Val Gly Phe Thr Val
                 85                  90                  95

Ile Leu Ile Ser Leu Tyr Val Gly Phe Phe Tyr Asn Val Ile Ile Ala
            100                 105                 110

Trp Ala Leu His Tyr Leu Phe Ser Ser Phe Thr Thr Glu Leu Pro Trp
        115                 120                 125

Ile His Cys Asn Asn Ser Trp Asn Ser Pro Asn Cys Ser Asp Ala His
    130                 135                 140

Pro Gly Asp Ser Ser Gly Asp Ser Ser Gly Leu Asn Asp Thr Phe Gly
145                 150                 155                 160

Thr Thr Pro Ala Ala Glu Tyr Phe Glu Arg Gly Val Leu His Leu His
                165                 170                 175

Gln Ser His Gly Ile Asp Asp Leu Gly Pro Pro Arg Trp Gln Leu Thr
            180                 185                 190

Ala Cys Leu Val Leu Val Ile Val Leu Leu Tyr Phe Ser Leu Trp Lys
        195                 200                 205

Gly Val Lys Thr Ser Gly Lys Val Val Trp Ile Thr Ala Thr Met Pro
    210                 215                 220

Tyr Val Val Leu Thr Ala Leu Leu Leu Arg Gly Val Thr Leu Pro Gly
225                 230                 235                 240

Ala Ile Asp Gly Ile Arg Ala Tyr Leu Ser Val Asp Phe Tyr Arg Leu
                245                 250                 255

Cys Glu Ala Ser Val Trp Ile Asp Ala Ala Thr Gln Val Cys Phe Ser
            260                 265                 270

Leu Gly Val Gly Phe Gly Val Leu Ile Ala Phe Ser Ser Tyr Asn Lys
        275                 280                 285

Phe Thr Asn Asn Cys Tyr Arg Asp Ala Ile Val Thr Thr Ser Ile Asn
    290                 295                 300

Ser Leu Thr Ser Phe Ser Ser Gly Phe Val Val Phe Ser Phe Leu Gly
305                 310                 315                 320

Tyr Met Ala Gln Lys His Ser Val Pro Ile Gly Asp Val Ala Lys Asp
                325                 330                 335

Gly Pro Gly Leu Ile Phe Ile Ile Tyr Pro Glu Ala Ile Ala Thr Leu
            340                 345                 350

Pro Leu Ser Ser Ala Trp Ala Val Val Phe Phe Ile Met Leu Leu Thr
        355                 360                 365

Leu Gly Ile Asp Ser Ala Met Gly Gly Met Glu Ser Val Ile Thr Gly
    370                 375                 380

Leu Ile Asp Glu Phe Gln Leu Leu His Arg His Arg Glu Leu Phe Thr
385                 390                 395                 400

Leu Phe Ile Val Leu Ala Thr Phe Leu Leu Ser Leu Phe Cys Val Thr
                405                 410                 415

Asn Gly Gly Ile Tyr Val Phe Thr Leu Leu Asp His Phe Ala Ala Gly
            420                 425                 430

Thr Ser Ile Leu Phe Gly Val Leu Ile Glu Ala Ile Gly Val Ala Trp
        435                 440                 445

Phe Tyr Gly Val Gly Gln Phe Ser Asp Asp Ile Gln Gln Met Thr Gly
    450                 455                 460

Gln Arg Pro Ser Leu Tyr Trp Arg Leu Cys Trp Lys Leu Val Ser Pro
465                 470                 475                 480

Cys Phe Leu Leu Phe Val Val Val Ser Ile Val Thr Phe Arg Pro
```

```
                    485                 490                 495
Pro His Tyr Gly Ala Tyr Ile Phe Pro Asp Trp Ala Asn Ala Leu Gly
                500                 505                 510

Trp Val Ile Ala Thr Ser Ser Met Ala Met Val Pro Ile Tyr Ala Ala
                515                 520                 525

Tyr Lys Phe Cys Ser Leu Pro Gly Ser Phe Arg Glu Lys Leu Ala Tyr
                530                 535                 540

Ala Ile Ala Pro Glu Lys Asp Arg Glu Leu Val Asp Arg Gly Glu Val
545                 550                 555                 560

Arg Gln Phe Thr Leu Arg His Trp Leu Lys Val
                565                 570

<210> SEQ ID NO 5
<211> LENGTH: 602
<212> TYPE: PRT
<213> ORGANISM: Artificial Sequence
<220> FEATURE:
<223> OTHER INFORMATION: dhDATopt_d protein sequence

<400> SEQUENCE: 5

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
                20                  25                  30

Leu Val Lys Glu Gln Asn Gly Val Gln Leu Thr Ser Ser Thr Leu Thr
            35                  40                  45

Asn Pro Arg Gln Ser Pro Val Glu Ala Gln Asp Arg Glu Thr Trp Gly
        50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
                100                 105                 110

Leu Phe Tyr Met Glu Leu Ala Leu Gly Gln Phe Asn Arg Glu Gly Ala
            115                 120                 125

Ala Gly Val Trp Lys Ile Cys Pro Ile Leu Lys Gly Val Gly Phe Thr
        130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
                180                 185                 190

His Pro Gly Asp Ser Ser Gly Asp Ser Ser Gly Leu Asn Asp Thr Phe
            195                 200                 205

Gly Thr Thr Pro Ala Ala Glu Tyr Phe Glu Arg Gly Val Leu His Leu
        210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255

Lys Gly Val Lys Thr Ser Gly Lys Val Val Trp Ile Thr Ala Thr Met
                260                 265                 270

Pro Tyr Val Val Leu Thr Ala Leu Leu Leu Arg Gly Val Thr Leu Pro
```

```
            275                 280                 285
Gly Ala Ile Asp Gly Ile Arg Ala Tyr Leu Ser Val Asp Phe Tyr Arg
    290                 295                 300

Leu Cys Glu Ala Ser Val Trp Ile Asp Ala Thr Gln Val Cys Phe
305                 310                 315                 320

Ser Leu Gly Val Gly Phe Gly Val Leu Ile Ala Phe Ser Ser Tyr Asn
                325                 330                 335

Lys Phe Thr Asn Asn Cys Tyr Arg Asp Ala Ile Val Thr Thr Ser Ile
                340                 345                 350

Asn Ser Leu Thr Ser Phe Ser Ser Gly Phe Val Val Phe Ser Phe Leu
                355                 360                 365

Gly Tyr Met Ala Gln Lys His Ser Val Pro Ile Gly Asp Val Ala Lys
                370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
                420                 425                 430

Gly Leu Ile Asp Glu Phe Gln Leu Leu His Arg His Arg Glu Leu Phe
                435                 440                 445

Thr Leu Phe Ile Val Leu Ala Thr Phe Leu Leu Ser Leu Phe Cys Val
    450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
                485                 490                 495

Trp Phe Tyr Gly Val Gly Gln Phe Ser Asp Asp Ile Gln Gln Met Thr
                500                 505                 510

Gly Gln Arg Pro Ser Leu Tyr Trp Arg Leu Cys Trp Lys Leu Val Ser
                515                 520                 525

Pro Cys Phe Leu Leu Phe Val Val Val Ser Ile Val Thr Phe Arg
530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
                580                 585                 590

Tyr Ala Ile Ala Pro Glu Lys Asp Arg Glu
    595                 600

<210> SEQ ID NO 6
<211> LENGTH: 620
<212> TYPE: PRT
<213> ORGANISM: Artificial Sequence
<220> FEATURE:
<223> OTHER INFORMATION: hDAT protein sequence

<400> SEQUENCE: 6

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
                20                  25                  30

Leu Val Lys Glu Gln Asn Gly Val Gln Leu Thr Ser Ser Thr Leu Thr
```

```
            35                  40                  45
Asn Pro Arg Gln Ser Pro Val Glu Ala Gln Asp Arg Glu Thr Trp Gly
 50                  55                  60
Lys Lys Ile Asp Phe Leu Leu Ser Val Ile Gly Phe Ala Val Asp Leu
 65                  70                  75                  80
Ala Asn Val Trp Arg Phe Pro Tyr Leu Cys Tyr Lys Asn Gly Gly Gly
                     85                  90                  95
Ala Phe Leu Val Pro Tyr Leu Leu Phe Met Val Ile Ala Gly Met Pro
                    100                 105                 110
Leu Phe Tyr Met Glu Leu Ala Leu Gly Gln Phe Asn Arg Glu Gly Ala
                115                 120                 125
Ala Gly Val Trp Lys Ile Cys Pro Ile Leu Lys Gly Val Gly Phe Thr
            130                 135                 140
Val Ile Leu Ile Ser Leu Tyr Val Gly Phe Phe Tyr Asn Val Ile Ile
145                 150                 155                 160
Ala Trp Ala Leu His Tyr Leu Phe Ser Ser Phe Thr Thr Glu Leu Pro
                    165                 170                 175
Trp Ile His Cys Asn Asn Ser Trp Asn Ser Pro Asn Cys Ser Asp Ala
                180                 185                 190
His Pro Gly Asp Ser Ser Gly Asp Ser Ser Gly Leu Asn Asp Thr Phe
            195                 200                 205
Gly Thr Thr Pro Ala Ala Glu Tyr Phe Glu Arg Gly Val Leu His Leu
210                 215                 220
His Gln Ser His Gly Ile Asp Asp Leu Gly Pro Pro Arg Trp Gln Leu
225                 230                 235                 240
Thr Ala Cys Leu Val Leu Val Ile Val Leu Leu Tyr Phe Ser Leu Trp
                    245                 250                 255
Lys Gly Val Lys Thr Ser Gly Lys Val Val Trp Ile Thr Ala Thr Met
                260                 265                 270
Pro Tyr Val Val Leu Thr Ala Leu Leu Leu Arg Gly Val Thr Leu Pro
            275                 280                 285
Gly Ala Ile Asp Gly Ile Arg Ala Tyr Leu Ser Val Asp Phe Tyr Arg
290                 295                 300
Leu Cys Glu Ala Ser Val Trp Ile Asp Ala Ala Thr Gln Val Cys Phe
305                 310                 315                 320
Ser Leu Gly Val Gly Phe Gly Val Leu Ile Ala Phe Ser Ser Tyr Asn
                    325                 330                 335
Lys Phe Thr Asn Asn Cys Tyr Arg Asp Ala Ile Val Thr Thr Ser Ile
                340                 345                 350
Asn Ser Leu Thr Ser Phe Ser Ser Gly Phe Val Val Phe Ser Phe Leu
            355                 360                 365
Gly Tyr Met Ala Gln Lys His Ser Val Pro Ile Gly Asp Val Ala Lys
370                 375                 380
Asp Gly Pro Gly Leu Ile Phe Ile Ile Tyr Pro Glu Ala Ile Ala Thr
385                 390                 395                 400
Leu Pro Leu Ser Ser Ala Trp Ala Val Val Phe Phe Ile Met Leu Leu
                    405                 410                 415
Thr Leu Gly Ile Asp Ser Ala Met Gly Gly Met Glu Ser Val Ile Thr
                420                 425                 430
Gly Leu Ile Asp Glu Phe Gln Leu Leu His Arg His Arg Glu Leu Phe
            435                 440                 445
Thr Leu Phe Ile Val Leu Ala Thr Phe Leu Leu Ser Leu Phe Cys Val
450                 455                 460
```

```
Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
            485                 490                 495

Trp Phe Tyr Gly Val Gly Gln Phe Ser Asp Asp Ile Gln Gln Met Thr
                500                 505                 510

Gly Gln Arg Pro Ser Leu Tyr Trp Arg Leu Cys Trp Lys Leu Val Ser
            515                 520                 525

Pro Cys Phe Leu Leu Phe Val Val Val Ser Ile Val Thr Phe Arg
        530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
            595                 600                 605

Val Arg Gln Phe Thr Leu Arg His Trp Leu Lys Val
610                 615                 620

<210> SEQ ID NO 7
<211> LENGTH: 731
<212> TYPE: PRT
<213> ORGANISM: Artificial Sequence
<220> FEATURE:
<223> OTHER INFORMATION: RQR8hDAT protein sequence

<400> SEQUENCE: 7

Ser Leu Leu Cys Trp Met Ala Leu Cys Leu Leu Gly Ala Asp His Ala
1               5                   10                  15

Asp Ala Cys Pro Tyr Ser Asn Pro Ser Leu Cys Ser Gly Gly Gly Gly
                20                  25                  30

Ser Glu Leu Pro Thr Gln Gly Thr Phe Ser Asn Val Ser Thr Asn Val
            35                  40                  45

Ser Pro Ala Lys Pro Thr Thr Thr Ala Cys Pro Tyr Ser Asn Pro Ser
50                  55                  60

Leu Cys Ser Gly Gly Gly Ser Pro Ala Pro Arg Pro Pro Thr Pro
65                  70                  75                  80

Ala Pro Thr Ile Ala Ser Gln Pro Leu Ser Leu Arg Pro Glu Ala Cys
                85                  90                  95

Arg Pro Ala Ala Gly Gly Ala Val His Thr Arg Gly Leu Asp Phe Ala
            100                 105                 110

Cys Asp Ile Tyr Ile Trp Ala Pro Leu Ala Gly Thr Cys Gly Val Leu
            115                 120                 125

Leu Leu Ser Leu Val Ile Thr Leu Tyr Cys Asn His Arg Asn Arg Arg
130                 135                 140

Arg Val Cys Lys Cys Pro Arg Pro Val Val Ser Ser Thr Leu Thr Asn
145                 150                 155                 160

Pro Arg Gln Ser Pro Val Glu Ala Gln Asp Arg Glu Thr Trp Gly Lys
                165                 170                 175

Lys Ile Asp Phe Leu Leu Ser Val Ile Gly Phe Ala Val Asp Leu Ala
            180                 185                 190

Asn Val Trp Arg Phe Pro Tyr Leu Cys Tyr Lys Asn Gly Gly Gly Ala
            195                 200                 205
```

```
Phe Leu Val Pro Tyr Leu Leu Phe Met Val Ile Ala Gly Met Pro Leu
            210                 215                 220
Phe Tyr Met Glu Leu Ala Leu Gly Gln Phe Asn Arg Glu Gly Ala Ala
225                 230                 235                 240
Gly Val Trp Lys Ile Cys Pro Ile Leu Lys Gly Val Gly Phe Thr Val
                245                 250                 255
Ile Leu Ile Ser Leu Tyr Val Gly Phe Phe Tyr Asn Val Ile Ile Ala
                260                 265                 270
Trp Ala Leu His Tyr Leu Phe Ser Ser Phe Thr Thr Glu Leu Pro Trp
            275                 280                 285
Ile His Cys Asn Asn Ser Trp Asn Ser Pro Asn Cys Ser Asp Ala His
        290                 295                 300
Pro Gly Asp Ser Ser Gly Asp Ser Ser Gly Leu Asn Asp Thr Phe Gly
305                 310                 315                 320
Thr Thr Pro Ala Ala Glu Tyr Phe Glu Arg Gly Val Leu His Leu His
                325                 330                 335
Gln Ser His Gly Ile Asp Asp Leu Gly Pro Pro Arg Trp Gln Leu Thr
            340                 345                 350
Ala Cys Leu Val Leu Val Ile Val Leu Leu Tyr Phe Ser Leu Trp Lys
        355                 360                 365
Gly Val Lys Thr Ser Gly Lys Val Val Trp Ile Thr Ala Thr Met Pro
370                 375                 380
Tyr Val Val Leu Thr Ala Leu Leu Leu Arg Gly Val Thr Leu Pro Gly
385                 390                 395                 400
Ala Ile Asp Gly Ile Arg Ala Tyr Leu Ser Val Asp Phe Tyr Arg Leu
                405                 410                 415
Cys Glu Ala Ser Val Trp Ile Asp Ala Ala Thr Gln Val Cys Phe Ser
            420                 425                 430
Leu Gly Val Gly Phe Gly Val Leu Ile Ala Phe Ser Ser Tyr Asn Lys
        435                 440                 445
Phe Thr Asn Asn Cys Tyr Arg Asp Ala Ile Val Thr Thr Ser Ile Asn
450                 455                 460
Ser Leu Thr Ser Phe Ser Ser Gly Phe Val Val Phe Ser Phe Leu Gly
465                 470                 475                 480
Tyr Met Ala Gln Lys His Ser Val Pro Ile Gly Asp Val Ala Lys Asp
                485                 490                 495
Gly Pro Gly Leu Ile Phe Ile Ile Tyr Pro Glu Ala Ile Ala Thr Leu
            500                 505                 510
Pro Leu Ser Ser Ala Trp Ala Val Val Phe Phe Ile Met Leu Leu Thr
        515                 520                 525
Leu Gly Ile Asp Ser Ala Met Gly Gly Met Glu Ser Val Ile Thr Gly
530                 535                 540
Leu Ile Asp Glu Phe Gln Leu Leu His Arg His Arg Glu Leu Phe Thr
545                 550                 555                 560
Leu Phe Ile Val Leu Ala Thr Phe Leu Leu Ser Leu Phe Cys Val Thr
                565                 570                 575
Asn Gly Gly Ile Tyr Val Phe Thr Leu Leu Asp His Phe Ala Ala Gly
            580                 585                 590
Thr Ser Ile Leu Phe Gly Val Leu Ile Glu Ala Ile Gly Val Ala Trp
        595                 600                 605
Phe Tyr Gly Val Gly Gln Phe Ser Asp Asp Ile Gln Gln Met Thr Gly
610                 615                 620
```

```
Gln Arg Pro Ser Leu Tyr Trp Arg Leu Cys Trp Lys Leu Val Ser Pro
625                 630                 635                 640

Cys Phe Leu Leu Phe Val Val Val Ser Ile Val Thr Phe Arg Pro
            645                 650                 655

Pro His Tyr Gly Ala Tyr Ile Phe Pro Asp Trp Ala Asn Ala Leu Gly
            660                 665                 670

Trp Val Ile Ala Thr Ser Ser Met Ala Met Val Pro Ile Tyr Ala Ala
            675                 680                 685

Tyr Lys Phe Cys Ser Leu Pro Gly Ser Phe Arg Glu Lys Leu Ala Tyr
            690                 695                 700

Ala Ile Ala Pro Glu Lys Asp Arg Glu Leu Val Asp Arg Gly Glu Val
705                 710                 715                 720

Arg Gln Phe Thr Leu Arg His Trp Leu Lys Val
            725                 730
```

<210> SEQ ID NO 8
<211> LENGTH: 620
<212> TYPE: PRT
<213> ORGANISM: Artificial Sequence
<220> FEATURE:
<223> OTHER INFORMATION: dhDATopt313N protein sequence

<400> SEQUENCE: 8

```
Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Thr Leu Thr
            35                  40                  45

Asn Pro Arg Gln Ser Pro Val Glu Ala Gln Asp Arg Glu Thr Trp Gly
50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
            115                 120                 125

Ala Gly Val Trp Lys Ile Cys Pro Ile Leu Lys Gly Val Gly Phe Thr
            130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
            180                 185                 190

His Pro Gly Asp Ser Ser Gly Asp Ser Ser Gly Leu Asn Asp Thr Phe
            195                 200                 205

Gly Thr Thr Pro Ala Ala Glu Tyr Phe Glu Arg Gly Val Leu His Leu
            210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255
```

Lys Gly Val Lys Thr Ser Gly Lys Val Val Trp Ile Thr Ala Thr Met
        260                 265                 270

Pro Tyr Val Val Leu Thr Ala Leu Leu Leu Arg Gly Val Thr Leu Pro
            275                 280                 285

Gly Ala Ile Asp Gly Ile Arg Ala Tyr Leu Ser Val Asp Phe Tyr Arg
        290                 295                 300

Leu Cys Glu Ala Ser Val Trp Ile Asn Ala Ala Thr Gln Val Cys Phe
305                 310                 315                 320

Ser Leu Gly Val Gly Phe Gly Val Leu Ile Ala Phe Ser Ser Tyr Asn
            325                 330                 335

Lys Phe Thr Asn Asn Cys Tyr Arg Asp Ala Ile Val Thr Thr Ser Ile
            340                 345                 350

Asn Ser Leu Thr Ser Phe Ser Ser Gly Phe Val Val Phe Ser Phe Leu
            355                 360                 365

Gly Tyr Met Ala Gln Lys His Ser Val Pro Ile Gly Asp Val Ala Lys
        370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
            405                 410                 415

Thr Leu Gly Ile Asp Ser Ala Met Gly Gly Met Glu Ser Val Ile Thr
            420                 425                 430

Gly Leu Ile Asp Glu Phe Gln Leu Leu His Arg His Arg Glu Leu Phe
        435                 440                 445

Thr Leu Phe Ile Val Leu Ala Thr Phe Leu Leu Ser Leu Phe Cys Val
450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
            485                 490                 495

Trp Phe Tyr Gly Val Gly Gln Phe Ser Asp Asp Ile Gln Gln Met Thr
        500                 505                 510

Gly Gln Arg Pro Ser Leu Tyr Trp Arg Leu Cys Trp Lys Leu Val Ser
        515                 520                 525

Pro Cys Phe Leu Leu Phe Val Val Val Ser Ile Val Thr Phe Arg
530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
            565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
        595                 600                 605

Val Arg Gln Phe Thr Leu Arg His Trp Leu Lys Val
        610                 615                 620

<210> SEQ ID NO 9
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 9

```
Phe Trp Val Leu Val Val Gly Gly Val Leu Ala Cys Tyr Ser Leu
1               5                   10                  15

Leu Val Thr Val Ala Phe Ile Ile Phe Trp Val
                20                  25
```

<210> SEQ ID NO 10
<211> LENGTH: 39
<212> TYPE: PRT
<213> ORGANISM: Artificial Sequence
<220> FEATURE:
<223> OTHER INFORMATION: CD28 endodomain

<400> SEQUENCE: 10

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr
            35
```

<210> SEQ ID NO 11
<211> LENGTH: 38
<212> TYPE: PRT
<213> ORGANISM: Artificial Sequence
<220> FEATURE:
<223> OTHER INFORMATION: OX40 endodomain

<400> SEQUENCE: 11

```
Arg Ser Arg Asp Gln Arg Leu Pro Pro Asp Ala His Lys Pro Pro Gly
1               5                   10                  15

Gly Gly Ser Phe Arg Thr Pro Ile Gln Glu Glu Gln Ala Asp Ala His
                20                  25                  30

Ser Thr Leu Ala Lys Ile
            35
```

<210> SEQ ID NO 12
<211> LENGTH: 114
<212> TYPE: PRT
<213> ORGANISM: Artificial Sequence
<220> FEATURE:
<223> OTHER INFORMATION: CD3 zeta endodomain

<400> SEQUENCE: 12

```
Arg Ser Arg Val Lys Phe Ser Arg Ser Ala Asp Ala Pro Ala Tyr Gln
1               5                   10                  15

Gln Gly Gln Asn Gln Leu Tyr Asn Glu Leu Asn Leu Gly Arg Arg Glu
                20                  25                  30

Glu Tyr Asp Val Leu Asp Lys Arg Arg Gly Arg Asp Pro Glu Met Gly
            35                  40                  45

Gly Lys Pro Arg Arg Lys Asn Pro Gln Glu Gly Leu Tyr Asn Glu Leu
        50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg
```

<210> SEQ ID NO 13

```
<211> LENGTH: 153
<212> TYPE: PRT
<213> ORGANISM: Artificial Sequence
<220> FEATURE:
<223> OTHER INFORMATION: CD28Z

<400> SEQUENCE: 13
```

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Val Lys Phe Ser Arg Ser
        35                  40                  45

Ala Asp Ala Pro Ala Tyr Gln Gln Gly Gln Asn Gln Leu Tyr Asn Glu
50                  55                  60

Leu Asn Leu Gly Arg Arg Glu Glu Tyr Asp Val Leu Asp Lys Arg Arg
65                  70                  75                  80

Gly Arg Asp Pro Glu Met Gly Gly Lys Pro Arg Arg Lys Asn Pro Gln
                85                  90                  95

Glu Gly Leu Tyr Asn Glu Leu Gln Lys Asp Lys Met Ala Glu Ala Tyr
            100                 105                 110

Ser Glu Ile Gly Met Lys Gly Glu Arg Arg Arg Gly Lys Gly His Asp
        115                 120                 125

Gly Leu Tyr Gln Gly Leu Ser Thr Ala Thr Lys Asp Thr Tyr Asp Ala
130                 135                 140

Leu His Met Gln Ala Leu Pro Pro Arg
145                 150

```
<210> SEQ ID NO 14
<211> LENGTH: 189
<212> TYPE: PRT
<213> ORGANISM: Artificial Sequence
<220> FEATURE:
<223> OTHER INFORMATION: CD28OXZ

<400> SEQUENCE: 14
```

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Asp Gln Arg Leu Pro Pro
        35                  40                  45

Asp Ala His Lys Pro Pro Gly Gly Gly Ser Phe Arg Thr Pro Ile Gln
50                  55                  60

Glu Glu Gln Ala Asp Ala His Ser Thr Leu Ala Lys Ile Arg Val Lys
65                  70                  75                  80

Phe Ser Arg Ser Ala Asp Ala Pro Ala Tyr Gln Gln Gly Gln Asn Gln
                85                  90                  95

Leu Tyr Asn Glu Leu Asn Leu Gly Arg Arg Glu Glu Tyr Asp Val Leu
            100                 105                 110

Asp Lys Arg Arg Gly Arg Asp Pro Glu Met Gly Gly Lys Pro Arg Arg
        115                 120                 125

Lys Asn Pro Gln Glu Gly Leu Tyr Asn Glu Leu Gln Lys Asp Lys Met
130                 135                 140

Ala Glu Ala Tyr Ser Glu Ile Gly Met Lys Gly Glu Arg Arg Arg Gly
145                 150                 155                 160

Lys Gly His Asp Gly Leu Tyr Gln Gly Leu Ser Thr Ala Thr Lys Asp

```
                165                 170                 175
Thr Tyr Asp Ala Leu His Met Gln Ala Leu Pro Pro Arg
            180                 185

<210> SEQ ID NO 15
<211> LENGTH: 234
<212> TYPE: PRT
<213> ORGANISM: Artificial Sequence
<220> FEATURE:
<223> OTHER INFORMATION: Spacer (hinge-CH2CH3 of human IgG1)

<400> SEQUENCE: 15

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 16
<211> LENGTH: 46
<212> TYPE: PRT
<213> ORGANISM: Artificial Sequence
<220> FEATURE:
<223> OTHER INFORMATION: Spacer (human CD8 stalk)

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45
```

<210> SEQ ID NO 17
<211> LENGTH: 20
<212> TYPE: PRT
<213> ORGANISM: Artificial Sequence
<220> FEATURE:
<223> OTHER INFORMATION: Spacer (human IgG1 hinge)

<400> SEQUENCE: 17

Ala Glu Pro Lys Ser Pro Asp Lys Thr His Thr Cys Pro Pro Cys Pro
1               5                   10                  15

Lys Asp Pro Lys
            20

<210> SEQ ID NO 18
<211> LENGTH: 237
<212> TYPE: PRT
<213> ORGANISM: Artificial Sequence
<220> FEATURE:
<223> OTHER INFORMATION: Spacer (IgG1 Hinge-Fc)

<400> SEQUENCE: 18

Ala Glu Pro Lys Ser Pro Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235

<210> SEQ ID NO 19
<211> LENGTH: 236
<212> TYPE: PRT
<213> ORGANISM: Artificial Sequence
<220> FEATURE:
<223> OTHER INFORMATION: Spacer (IgG1 Hinge - Fc modified to remove Fc
      receptor recognition motifs)

<400> SEQUENCE: 19

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Lys Asp Pro Lys
225                 230                 235

<210> SEQ ID NO 20
<211> LENGTH: 20
<212> TYPE: PRT
<213> ORGANISM: Thosea asigna virus

<400> SEQUENCE: 20

Arg Ala Glu Gly Arg Gly Ser Leu Leu Thr Cys Gly Asp Val Glu Glu
1               5                   10                  15

Asn Pro Gly Pro
            20

<210> SEQ ID NO 21
<211> LENGTH: 402
<212> TYPE: PRT
<213> ORGANISM: Artificial Sequence
<220> FEATURE:
<223> OTHER INFORMATION: iCasp9 suicide gene

<400> SEQUENCE: 21

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
                20                  25                  30

Leu Glu Asp Gly Lys Lys Val Asp Ser Ser Arg Asp Arg Asn Lys Pro

```
            35                  40                  45
Phe Lys Phe Met Leu Gly Lys Gln Glu Val Ile Arg Gly Trp Glu Glu
 50                  55                  60
Gly Val Ala Gln Met Ser Val Gly Gln Arg Ala Lys Leu Thr Ile Ser
 65                  70                  75                  80
Pro Asp Tyr Ala Tyr Gly Ala Thr Gly His Pro Gly Ile Ile Pro Pro
                 85                  90                  95
His Ala Thr Leu Val Phe Asp Val Glu Leu Leu Lys Leu Glu Ser Gly
                100                 105                 110
Gly Gly Ser Gly Val Asp Gly Phe Gly Asp Val Gly Ala Leu Glu Ser
            115                 120                 125
Leu Arg Gly Asn Ala Asp Leu Ala Tyr Ile Leu Ser Met Glu Pro Cys
130                 135                 140
Gly His Cys Leu Ile Ile Asn Asn Val Asn Phe Cys Arg Glu Ser Gly
145                 150                 155                 160
Leu Arg Thr Arg Thr Gly Ser Asn Ile Asp Cys Glu Lys Leu Arg Arg
                165                 170                 175
Arg Phe Ser Ser Leu His Phe Met Val Glu Val Lys Gly Asp Leu Thr
            180                 185                 190
Ala Lys Lys Met Val Leu Ala Leu Leu Glu Leu Ala Gln Gln Asp His
        195                 200                 205
Gly Ala Leu Asp Cys Cys Val Val Val Ile Leu Ser His Gly Cys Gln
210                 215                 220
Ala Ser His Leu Gln Phe Pro Gly Ala Val Tyr Gly Thr Asp Gly Cys
225                 230                 235                 240
Pro Val Ser Val Glu Lys Ile Val Asn Ile Phe Asn Gly Thr Ser Cys
                245                 250                 255
Pro Ser Leu Gly Gly Lys Pro Lys Leu Phe Phe Ile Gln Ala Cys Gly
            260                 265                 270
Gly Glu Gln Lys Asp His Gly Phe Glu Val Ala Ser Thr Ser Pro Glu
        275                 280                 285
Asp Glu Ser Pro Gly Ser Asn Pro Glu Pro Asp Ala Thr Pro Phe Gln
290                 295                 300
Glu Gly Leu Arg Thr Phe Asp Gln Leu Asp Ala Ile Ser Ser Leu Pro
305                 310                 315                 320
Thr Pro Ser Asp Ile Phe Val Ser Tyr Ser Thr Phe Pro Gly Phe Val
                325                 330                 335
Ser Trp Arg Asp Pro Lys Ser Gly Ser Trp Tyr Val Glu Thr Leu Asp
            340                 345                 350
Asp Ile Phe Glu Gln Trp Ala His Ser Glu Asp Leu Gln Ser Leu Leu
        355                 360                 365
Leu Arg Val Ala Asn Ala Val Ser Val Lys Gly Ile Tyr Lys Gln Met
370                 375                 380
Pro Gly Cys Phe Asn Phe Leu Arg Lys Lys Leu Phe Phe Lys Thr Ser
385                 390                 395                 400
Ala Ser

<210> SEQ ID NO 22
<211> LENGTH: 157
<212> TYPE: PRT
<213> ORGANISM: Artificial Sequence
<220> FEATURE:
<223> OTHER INFORMATION: RQR8 suicide gene

<400> SEQUENCE: 22
```

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155
```

<210> SEQ ID NO 23
<211> LENGTH: 1558
<212> TYPE: DNA
<213> ORGANISM: Artificial Sequence
<220> FEATURE:
<223> OTHER INFORMATION: hDAT tm11-12 nucleic acid sequence

<400> SEQUENCE: 23

```
gagcaagagc aagtgcagcg tgggcctgat gagcagcgtg gtggcccag ccaaggagcc      60
caacgccgtg ggccctaagg aggtggagct gatcctggtg aaggagcaga acggcgtgca    120
gctgaccagc agcaccctga ccaaccctag acagagcccc gtggaggccc aggaccggga    180
gacctggggc aagaagatcg acttcctgct gagcgtgatc ggcttcgccg tggacctggc    240
caacgtgtgg cggttcccct acctgtgcta caagaacggc ggaggcgcct tcctggtgcc    300
ctacctgctg ttcatggtga tcgccggcat gcctctgttc tacatggagc tggccctggg    360
ccagttcaac cgggagggcg ccgccggcgt gtggaaaatc tgccctatcc tgaagggcgt    420
gggcttcacc gtgatcctga tcagcctgta cgtgggcttc ttctacaacg tgatcatcgc    480
ctgggccctg cactacctgt tcagcagctt caccaccgag ctgccctgga ttcactgcaa    540
caacagctgg aacagcccca actgcagcga cgcccacccc ggcgacagca gcggcgacag    600
cagcggcctg aacgacacct tcggcaccac cccagccgcc gagtacttcg agcgcggcgt    660
gctgcacctg caccagagcc acggcatcga cgacctgggc ccacctcggt ggcagctgac    720
cgcctgcctg gtgctggtga tcgtgctgct gtacttcagc ctgtggaagg gcgtgaagac    780
cagcggcaag gtggtgtgga tcaccgccac catgcctac gtggtgctga ccgccctgct    840
gctgcgcggc gtgaccctgc ccggcgccat cgacggcatc cgggcctacc tgagcgtgga    900
cttctaccgg ctgtgcgagg ccagcgtgtg gatcgacgcc gccacccagg tgtgcttcag    960
cctgggcgtg ggcttcggcg tgctgatcgc cttcagcagc tacaacaagt tcaccaacaa   1020
ctgctaccgg gacgccatcg tgaccaccag catcaacagc ctgaccagct tcagcagcgg   1080
cttcgtggtg ttcagcttcc tgggctacat ggcccagaag cacagcgtgc ccatcggcga   1140
```

| | |
|---|---|
| cgtggccaag gacggtcccg gcctgatctt catcatctac cccgaggcca tcgccaccct | 1200 |
| gcccctgagc agcgcctggg ccgtggtgtt cttcatcatg ctgctgaccc tgggcatcga | 1260 |
| cagcgctatg ggcggcatgg agagcgtgat caccggcctg atcgacgagt ccagctgct | 1320 |
| gcaccggcac cgggagctgt tcaccctgtt catcgtgctg gccaccttcc tgctgagcct | 1380 |
| gttctgcgtg accaacggcg gcatctacgt gttcaccctg ctggaccact cgccgccgg | 1440 |
| caccagcatc ctgttcggcg tgctgatcga ggccatcggc gtggcctggt tctacggcgt | 1500 |
| gggtcagttc agcgacgaca tccagcagat gaccggccag cggcccagcc tgtactga | 1558 |

<210> SEQ ID NO 24
<211> LENGTH: 1573
<212> TYPE: DNA
<213> ORGANISM: Artificial Sequence
<220> FEATURE:
<223> OTHER INFORMATION: dddhDAT nucleic acid sequence

<400> SEQUENCE: 24

| | |
|---|---|
| gagacctctg gcggcagcct accaagaaca actggaccga ccggtggtac ctcacccta | 60 |
| ccgagtcggc gacacagtgt gggtccgccg acaccagact aagaacctag aacctcgctg | 120 |
| gaaaggacct tacacagtcc tgctgaccac ccccaccgcc ctcaaagtag acggcatcgc | 180 |
| agcttggata cacgccgccc acgtgaaggc tgccgacccc ggggtggac catcctctag | 240 |
| actgtcgacg ccaccatgag acagagcccc gtggaggccc aggaccggga gacctggggc | 300 |
| aagaagatcg acttcctgct gagcgtgatc ggcttcgccg tggacctggc caacgtgtgg | 360 |
| cggttcccct acctgtgcta caagaacggc ggaggcgcct cctggtgcc ctacctgctg | 420 |
| ttcatggtga tcgccggcat gctggtccgc aggggcgcgc gcgcagggcc caggatgccg | 480 |
| cggggctgga ccgcgctttg cttgctgagt ttgctgcctt ctgggttcat gagtcttgac | 540 |
| aacaacggta ctgctacccc agagttacct acccagggaa catttcaaa tgtttctaca | 600 |
| aatgtatcct accaagaaac tacaacacct agtaccttg gaagtaccag cctgcaccct | 660 |
| gtgtctcaac atggcaatga ggccacaaca acatcacag aaacgacagt caaattcaca | 720 |
| tctacctctg tgataacctc agtttatgga aacacaaact cttctgtcca gtcacagacc | 780 |
| tctgtaatca gcacagtgtt caccaccca gccaacgttt caactccaga acaaccttg | 840 |
| aagcctagcc tgtcacctgg aaatgtttca gacctttcaa ccactagcac tagccttgca | 900 |
| acatctccca ctaaacccta tacatcatct tctcctatcc taagtgacat caaggcagaa | 960 |
| atcaaatgtt caggcatcag agaagtgaaa ttgactcagg catctgcct ggagcaaaat | 1020 |
| aagacctcca gctgtgcgga gtttaagaag acaggggag agggcctggc ccgagtgctg | 1080 |
| tgtgggagg agcaggctga tgctgatgct ggggcccagg tatgctccct gctccttgcc | 1140 |
| cagtctgagg tgaggcctca gtgtctactg ctggtcttgg ccaacagaac agaaatttcc | 1200 |
| agcaaactcc aacttatgaa aaagcaccaa tctgacctga aaaagctggg gatcctagat | 1260 |
| ttcactgagc aagatgttgc aagccaccag agctattccc aaaagaccct gattgcactg | 1320 |
| gtcacctcgg gagccctgct ggctgtcttg ggcatcactg gctatttcct gatgaatcgc | 1380 |
| cgcagctgga gccccacagg agaaaggctg ggcgaagacc ttattacac ggaaaacggt | 1440 |
| ggataaggcg cgtcatcatc gatccggatt agtccaattt gttaaagaca ggatatcagt | 1500 |
| ggtccaggct ctagttttga ctcaacaata tcaccagctg aagcctatag agtacgagcc | 1560 |
| atagataaaa taa | 1573 |

<210> SEQ ID NO 25
<211> LENGTH: 1714
<212> TYPE: DNA
<213> ORGANISM: Artificial Sequence
<220> FEATURE:
<223> OTHER INFORMATION: dhDAT nucleic acid sequence

<400> SEQUENCE: 25

| | | | | |
|---|---|---|---|---|
| gagacagagc | cccgtggagg | cccaggaccg | ggagacctgg | ggcaagaaga tcgacttcct | 60 |
| gctgagcgtg | atcggcttcg | ccgtggacct | ggccaacgtg | tggcggttcc cctacctgtg | 120 |
| ctacaagaac | ggcggaggcg | ccttcctggt | gccctacctg | ctgttcatgg tgatcgccgg | 180 |
| catgcctctg | ttctacatgg | agctggccct | gggccagttc | aaccgggagg cgccgccgg | 240 |
| cgtgtggaaa | atctgcccta | tcctgaaggg | cgtgggcttc | accgtgatcc tgatcagcct | 300 |
| gtacgtgggc | ttcttctaca | cgtgatcat | cgcctgggcc | ctgcactacc tgttcagcag | 360 |
| cttcaccacc | gagctgccct | ggattcactg | caacaacagc | tggaacagcc ccaactgcag | 420 |
| cgacgcccac | cccggcgaca | gcagcggcga | cagcagcggc | ctgaacgaca ccttcggcac | 480 |
| caccccagcc | gccgagtact | tcgagcgcgg | cgtgctgcac | ctgcaccaga gccacggcat | 540 |
| cgacgacctg | ggcccacctc | ggtggcagct | gaccgcctgc | ctggtgctgg tgatcgtgct | 600 |
| gctgtacttc | agcctgtgga | agggcgtgaa | gaccagcggc | aaggtggtgt ggatcaccgc | 660 |
| caccatgccc | tacgtggtgc | tgaccgcccc | tgctgcgc | ggcgtgaccc tgcccggcgc | 720 |
| catcgacggc | atccgggcct | acctgagcgt | ggacttctac | cggctgtgcg aggccagcgt | 780 |
| gtggatcgac | gccgccaccc | aggtgtgctt | cagcctgggc | gtgggcttcg gcgtgctgat | 840 |
| cgccttcagc | agctacaaca | agttccacca | caactgctac | cgggacgcca tcgtgaccac | 900 |
| cagcatcaac | agcctgacca | gcttcagcag | cggcttcgtg | gtgttcagct tcctgggcta | 960 |
| catggcccag | aagcacagcg | tgcccatcgg | cgacgtggcc | aaggacggtc ccggcctgat | 1020 |
| cttcatcatc | taccccgagg | ccatcgccac | cctgccctg | agcagcgcct gggccgtggt | 1080 |
| gttcttcatc | atgctgctga | ccctgggcat | cgacagcgct | atgggcggca tggagagcgt | 1140 |
| gatcaccggc | ctgatcgacg | agttccagct | gctgcaccgg | caccgggagc tgttcacccct | 1200 |
| gttcatcgtg | ctggccacct | tcctgctgag | cctgttctgc | gtgaccaacg gcggcatcta | 1260 |
| cgtgttcacc | ctgctggacc | acttcgccgc | cggcaccagc | atcctgttcg gcgtgctgat | 1320 |
| cgaggccatc | ggcgtggcct | ggttctacgg | cgtgggtcag | ttcagcgacg acatccagca | 1380 |
| gatgaccggc | cagcggccca | gcctgtactg | gcggctgtgc | tggaagctgg tgagcccttg | 1440 |
| cttcctgctg | ttcgtggtgg | tgtgagcat | cgtgaccttc | cggccacctc actacggcgc | 1500 |
| ctacatcttc | cccgactggg | ccaacgccct | gggctgggtg | atcgccacca gcagcatggc | 1560 |
| tatggtgccc | atctacgccg | cctacaagtt | ctgcagcctg | cccggcagct tccgcgagaa | 1620 |
| gctggcctac | gccatcgccc | cagagaagga | ccgggagctg | gtggaccgcg cgaggtgcg | 1680 |
| gcagttcacc | ctgcggcact | ggctgaaggt | gtga | | 1714 |

<210> SEQ ID NO 26
<211> LENGTH: 1807
<212> TYPE: DNA
<213> ORGANISM: Artificial Sequence
<220> FEATURE:
<223> OTHER INFORMATION: dhDATopt_d nucleic acid sequence

<400> SEQUENCE: 26
gagcaagagc aagtgcagcg tgggcctgat gagcagcgtg gtggcccag ccaaggagcc     60

```
caacgccgtg ggccctaagg aggtggagct gatcctggtg aaggagcaga acggcgtgca    120
gctgaccagc agcaccctga ccaaccctag acagagcccc gtggaggccc aggaccggga    180
gacctggggc aagaagatcg acttcctgct gagcgtgatc ggcttcgccg tggacctggc    240
caacgtgtgg cggttcccct acctgtgcta caagaacggc ggaggcgcct tcctggtgcc    300
ctacctgctg ttcatggtga tcgccggcat gcctctgttc tacatggagc tggccctggg    360
ccagttcaac cggagggcg ccgccggcgt gtggaaaatc tgccctatcc tgaagggcgt    420
gggcttcacc gtgatcctga tcagcctgta cgtgggcttc ttctacaacg tgatcatcgc    480
ctgggccctg cactacctgt tcagcagctt caccaccgag ctgccctgga ttcactgcaa    540
caacagctgg aacagcccca actgcagcga cgcccacccc ggcgacagca gcggcgacag    600
cagcggcctg aacgacacct cggcaccac cccagccgcc gagtacttcg agcgcggcgt    660
gctgcacctg caccagagcc acggcatcga cgacctgggc ccacctcggt ggcagctgac    720
cgcctgcctg gtgctggtga tcgtgctgct gtacttcagc ctgtggaagg gcgtgaagac    780
cagcggcaag gtggtgtgga tcaccgccac catgcctac gtggtgctga ccgccctgct    840
gctgcgcggc gtgaccctgc cggcgccat cgacggcatc cgggcctacc tgagcgtgga    900
cttctaccgg ctgtgcgagg ccagcgtgtg gatcgacgcc gcacccagg tgtgcttcag    960 cctgggcgtg ggcttcggcg tgctgatcgc cttcagcagc tacaacaagt tcaccaacaa   1020
ctgctaccgg gacgccatcg tgaccaccag catcaacagc ctgaccagct tcagcagcgg   1080
cttcgtggtg ttcagcttcc tgggctacat ggccagaaag cacagcgtgc ccatcggcga   1140
cgtggccaag gacggtcccg gcctgatctt catcatctac cccgaggcca tcgccaccct   1200
gcccctgagc agcgcctggg ccgtggtgtt cttcatcatg ctgctgaccc tgggcatcga   1260
cagcgctatg ggcggcatgg agagcgtgat caccggcctg atcgacgagt tccagctgct   1320
gcaccggcac cgggagctgt tcaccctgtt catcgtgctg gccaccttcc tgctgagcct   1380
gttctgcgtg accaacggcg gcatctacgt gttcaccctg ctggaccact cgccgccgg   1440 caccagcatc ctgttcggcg tgctgatcga ggccatcggc gtggcctggt tctacggcgt   1500
gggtcagttc agcgacgaca tccagcagat gaccggccag cggcccagcc tgtactggcg   1560
gctgtgctgg aagctggtga gcccttgctt cctgctgttc gtggtggtgg tgagcatcgt   1620
gaccttccgg ccacctcact acggcgccta catcttcccc gactgggca acgccctggg   1680 ctgggtgatc gccaccagca gcatggctat ggtgcccatc tacgccgcct acaagttctg   1740
cagcctgccc ggcagcttcc gcgagaagct ggcctacgcc atcgccccag agaaggaccg   1800
ggagtga                                                              1807
```

<210> SEQ ID NO 27  
<211> LENGTH: 1861  
<212> TYPE: DNA  
<213> ORGANISM: Artificial Sequence  
<220> FEATURE:  
<223> OTHER INFORMATION: hDAT nucleic acid sequence
<400> SEQUENCE: 27

```
gagcaagtcc aaatgcagcg tgggactgat gtccagcgtg gttgccccg ctaaggagcc     60 caacgccgtg ggccccaagg aggtggaact gattctcgtg aaggagcaga acggcgtgca    120
gctcacctcc agcacactga ccaaccctag gcagagcccc gtggaggccc aggaccggga    180
gacctggggc aagaaaatcg acttcctgct cagcgtgatc ggcttcgccg tcgacctggc    240
taacgtttgg cggttcccct acctgtgcta caagaacggc ggaggcgctt tcctggtgcc    300
```

```
ctacctcctc tttatggtga tcgctggcat gcccctgttc tacatggagc tggccctcgg      360
ccagtttaac cgggagggag ccgcaggtgt gtggaagatt tgccccatcc tcaaaggcgt      420
gggattcacc gtgatcctga tcagcctgta cgtaggcttc ttttacaacg tcatcattgc      480
ctgggctctc cactacctgt tctcgagctt caccacagag ctgccctgga tccactgcaa      540
caatagctgg aacagcccca actgcagcga tgcgcacccc ggcgacagct ccggagacag      600
ctcaggcctg aacgacacct tcggaaccac acccgccgct gaatacttcg aacggggcgt      660
gctgcacctc catcagagcc acggcatcga tgaccttggt cctcccaggt ggcagctgac      720
cgcctgtctg gtgctcgtca tcgtgctgct ctacttcagc ctgtggaagg gcgtgaagac      780
aagcggcaag gtggtctgga tcaccgccac aatgccatat gtggtcctga ccgccctgct      840
cctgcggggg gtgaccctgc ctggggccat cgacggcatt cgggcctacc tgagcgtgga      900
cttctaccgg ctgtgcgagg ctagcgtgtg gatcgacgct gccactcaag tgtgcttcag      960
cctgggcgtg ggattcgggg tcctgatcgc cttcagctcc tacaacaagt tcaccaacaa     1020
ttgctaccgc gacgccatcg tcaccacaag catcaactcc ctgactagtt tttcgagcgg     1080
ctttgtcgtg ttcagctttc tgggatacat ggcccagaag cacagcgtgc ccatcggtga     1140
cgtcgccaag gacggccccg ggctgatctt cattatctac cctgaggcca tcgctaccct     1200
gccccctgagc tccgcctggg ctgtcgtgtt ctttatcatg ctgctcaccc tcggcatcga     1260
cagcgctatg ggaggcatgg agagcgtcat caccggcctg atcgacgaat ccagctcct     1320
gcaccggcat cgcgagctgt tcaccctgtt catcgtgctg ccaccttcc ttctgagcct     1380
gttctgcgtg accaacggcg gaatctacgt gttcaccctc ctggaccact cgctgccgg     1440
cacctcaata ttgttcggcg tgctgatcga ggcgatcggc gtggcctggt tctacggagt     1500
gggccagttc agcgacgata tccagcagat gaccggtcag cggcccagcc tgtactggcg     1560
gctgtgctgg aagctcgtct cccccctgct tctcctgttc gtggtcgttg tgtcaattgt     1620
gaccttccgg cctccccact acggcgccta catcttcccc gactgggcca atgcattggg     1680
ctgggtgatc gcaaccagct ccatggctat ggtgcccatc tacgctgcct acaagttctg     1740
tagcctgccc ggaagcttcc gggagaagct ggcgtacgct atcgccccg agaaggaccg     1800
ggagctggtg accgcggcg aggtgcggca gttcaccctg cggcactggc tgaaggtgtg     1860
a                                                                    1861
```

<210> SEQ ID NO 28
<211> LENGTH: 2204
<212> TYPE: DNA
<213> ORGANISM: Artificial Sequence
<220> FEATURE:
<223> OTHER INFORMATION: hDAT nucleic acid sequence

<400> SEQUENCE: 28

```
tgggcaccag cctgctgtgc tggatggccc tgtgcctgct gggcgccgac cacgccgatg       60
cctgccccta cagcaacccc agcctgtgca gcggaggcgg cggcagcgag ctgcccaccc      120
agggcaccct tccaacgtg tccaccaacg tgagcccagc caagcccacc accaccgcct      180
gtccttattc caatccttcc ctgtgtagcg aggggggagg cagcccagcc cccagacctc     240
ccaccccagc ccccaccatc gccagccagc tctgagcct gagacccgag gcctgccgcc     300
cagccgccgg cggcgccgtg cacaccgagg gcctggattt cgcctgcgat atctacatct     360
gggcccccact ggccggcacc tgtggcgtgc tgctgctgag cctggtgatc accctgtact    420
```

```
gcaaccaccg caaccgcagg cgcgtgtgca agtgccccag gcccgtggtg agcagcaccc      480
tgaccaaccc tagacagagc cccgtggagg cccaggaccg ggagacctgg ggcaagaaga      540
tcgacttcct gctgagcgtg atcggcttcg ccgtggacct ggccaacgtg tggcggttcc      600
cctacctgtg ctacaagaac ggcggaggcg ccttcctggt gccctacctg ctgttcatgg      660
tgatcgccgg catgcctctg ttctacatgg agctggccct gggccagttc aaccgggagg      720 cgccgccgg cgtgtggaaa atctgcccta tcctgaaggg cgtgggcttc accgtgatcc      780
tgatcagcct gtacgtgggc ttcttctaca acgtgatcat cgcctgggcc ctgcactacc      840
tgttcagcag cttcaccacc gagctgccct ggattcactg caacaacagc tggaacagcc      900
ccaactgcag cgacgcccac cccggcgaca gcagcggcga cagcagcggc ctgaacgaca      960
ccttcggcac cacccagcc gccgagtact tcgagcgcgg cgtgctgcac ctgcaccaga     1020
gccacggcat cgacgacctg ggcccacctc ggtggcagct gaccgcctgc ctggtgctgg     1080
tgatcgtgct gctgtacttc agcctgtgga agggcgtgaa gaccagcggc aaggtggtgt     1140
ggatcaccgc caccatgccc tacgtggtgc tgaccgccct gctgctgcgc ggcgtgaccc     1200
tgcccggcgc catcgacggc atccgggcct acctgagcgt ggacttctac cggctgtgcg     1260
aggccagcgt gtggatcgac gccgccaccc aggtgtgctt cagcctgggc gtgggcttcg     1320
gcgtgctgat cgccttcagc agctacaaca agttcaccaa caactgctac cgggacgcca     1380
tcgtgaccac cagcatcaac agcctgacca gcttcagcag cggcttcgtg gtgttcagct     1440
tcctgggcta catggcccag aagcacagcg tgcccatcgg cgacgtggcc aaggacggtc     1500
ccggcctgat cttcatcatc taccccgagg ccatcgccac cctgcccctg agcagcgcct     1560
gggccgtggt gttcttcatc atgctgctga ccctgggcat cgacagcgct atgggcggca     1620
tggagagcgt gatcaccggc ctgatcgacg agttccagct gctgcaccgg caccgggagc     1680
tgttcaccct gttcatcgtg ctggccacct tcctgctgag cctgttctgc gtgaccaacg     1740
gcggcatcta cgtgttcacc ctgctggacc acttcgccgc cggcaccagc atcctgttcg     1800
gcgtgctgat cgaggccatc ggcgtggcct ggttctacgg cgtgggtcag ttcagcgacg     1860
acatccagca gatgaccggc cagcggccca gcctgtactg cggctgtgc tggaagctgg     1920 tgagcccttg cttcctgctg ttcgtggtgg tggtgagcat cgtgaccttc cggccaccctc     1980 actacggcgc ctacatcttc cccgactggg ccaacgccct gggctgggtg atcgccacca     2040
gcagcatggc tatggtgccc atctacgccg cctacaagtt ctgcagcctg cccggcagct     2100
tccgcgagaa gctggcctac gccatcgccc agagaaggga ccgggagctg gtggaccgcg     2160
gcgaggtgcg gcagttcacc ctgcggcact ggctgaaggt gtga                     2204
```

<210> SEQ ID NO 29
<211> LENGTH: 1861
<212> TYPE: DNA
<213> ORGANISM: Artificial Sequence
<220> FEATURE:
<223> OTHER INFORMATION: dhDATopt313N nucleic acid sequence

<400> SEQUENCE: 29

```
gagcaagagc aagtgcagcg tgggcctgat gagcagcgtg gtggcccag ccaaggagcc        60 caacgccgtg ggccctaagg aggtggagct gatcctggtg aaggagcaga acggcgtgca      120
gctgaccagc agcacccctga ccaaccctag acagagcccc gtggaggccc aggaccggga      180
gacctggggc aagaagatcg acttcctgct gagcgtgatc ggcttcgccg tggacctggc      240
caacgtgtgg cggttcccct acctgtgcta caagaacggc ggaggcgcct tcctggtgcc      300
```

-continued

```
ctacctgctg ttcatggtga tcgccggcat gcctctgttc tacatggagc tggccctggg    360
ccagttcaac cgggagggcg ccgccggcgt gtggaaaatc tgccctatcc tgaagggcgt    420
gggcttcacc gtgatcctga tcagcctgta cgtgggcttc ttctacaacg tgatcatcgc    480
ctgggccctg cactacctgt tcagcagctt caccaccgag ctgccctgga ttcactgcaa    540
caacagctgg aacagcccca actgcagcga cgcccacccc ggcgacagca gcggcgacag    600
cagcggcctg aacgacacct tcggcaccac cccagccgcc gagtacttcg agcgcggcgt    660
gctgcacctg caccagagcc acggcatcga cgacctgggc ccacctcggt ggcagctgac    720
cgcctgcctg gtgctggtga tcgtgctgct gtacttcagc ctgtggaagg gcgtgaagac    780
cagcggcaag gtggtgtgga tcaccgccac catgccctac gtggtgctga ccgccctgct    840
gctgcgcggc gtgaccctgc ccggcgccat cgacggcatc cgggcctacc tgagcgtgga    900
cttctaccgg ctgtgcgagg ccagcgtgtg gatcaacgcc gccacccagg tgtgcttcag    960
cctgggcgtg ggcttcggcg tgctgatcgc cttcagcagc tacaacaagt tcaccaacaa   1020
ctgctaccgg gacgccatcg tgaccaccag catcaacagc ctgaccagct tcagcagcgg   1080
cttcgtggtg ttcagcttcc tgggctacat ggcccagaag cacagcgtgc ccatcggcga   1140
cgtggccaag gacggtcccg gcctgatctt catcatctac cccgaggcca tcgccaccct   1200
gcccctgagc agcgcctggg ccgtggtgtt cttcatcatg ctgctgaccc tgggcatcga   1260
cagcgctatg ggcggcatgg agagcgtgat caccggcctg atcgacgagt ccagctgct   1320 gcaccggcac cgggagctgt tcaccctgtt catcgtgctg gccaccttcc tgctgagcct   1380
gttctgcgtg accaacggcg gcatctacgt gttcaccctg ctggaccact tcgccgccgg   1440
caccagcatc ctgttcggcg tgctgatcga ggccatcggc gtggcctggt tctacgcgt   1500 gggtcagttc agcgacgaca tccagcagat gaccggccag cggcccagcc tgtactggcg   1560
gctgtgctgg aagctggtga gcccttgctt cctgctgttc gtggtggtgg tgagcatcgt   1620
gaccttccgg ccacctcact acggcgccta catcttcccc gactgggcca acgccctggg   1680
ctgggtgatc gccaccagca gcatggctat ggtgcccatc tacgccgcct acaagttctg   1740
cagcctgccc ggcagcttcc gcgagaagct ggcctacgcc atcgcccag agaaggaccg   1800 ggagctggtg gaccgcggcg aggtgcggca gttcacctg cggcactggc tgaaggtgtg   1860
a                                                                  1861
```